US009132217B2

(12) United States Patent
Soykan et al.

(10) Patent No.: US 9,132,217 B2
(45) Date of Patent: Sep. 15, 2015

(54) MULTIMODAL DIALYSIS SYSTEM

(71) Applicant: Medtronic, Inc., Minneapolis, MN (US)

(72) Inventors: Orhan Soykan, Shoreview, MN (US);
Bryant J. Pudil, Plymouth, MN (US);
Thomas E. Meyer, Maple Grove, MN (US); Linda L. Ruetz, New Brighton, MN (US); Carl Schu, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 274 days.

(21) Appl. No.: 13/844,599

(22) Filed: Mar. 15, 2013

(65) Prior Publication Data
US 2013/0274642 A1 Oct. 17, 2013

Related U.S. Application Data

(63) Continuation-in-part of application No. 13/424,454, filed on Mar. 20, 2012, now Pat. No. 8,951,219, and a continuation-in-part of application No. 13/424,467, filed on Mar. 20, 2012, now Pat. No. 8,926,542, and a
(Continued)

(51) Int. Cl.
*A61M 1/14* (2006.01)
*A61B 5/00* (2006.01)
(Continued)

(52) U.S. Cl.
CPC ............... *A61M 1/14* (2013.01); *A61B 5/0452* (2013.01); *A61B 5/0488* (2013.01); *A61B 5/145* (2013.01); *A61B 5/4848* (2013.01);
(Continued)

(58) Field of Classification Search
CPC ...... A61M 1/14; A61M 1/342; A61M 1/3455; A61M 1/3612; A61B 5/02; A61B 5/02108; A61B 5/02116; A61B 5/02125; A61B 5/04012; A61B 5/0402
USPC .................... 604/5.01, 5.04, 6.09, 6.11, 4.01; 210/645, 646, 746
See application file for complete search history.

(56) References Cited

U.S. PATENT DOCUMENTS 4,374,382 A 2/1983 Markowitz
4,556,063 A 12/1985 Thompson et al.
(Continued)

OTHER PUBLICATIONS

Lima, et. al., An electrochemical sensor based on nanostructure hollandite-type manganese oxide for detection of potassium ion, Sensors, 2009, 6613-6625, 9.
(Continued)

*Primary Examiner* — Leslie Deak
(74) *Attorney, Agent, or Firm* — Hahn & Voight PLLC; Roger C. Hahn; Kenneth J. Collier

(57) ABSTRACT

A dialysis device for operation in multiple modes and for maintaining a known gradient of potassium ion or other electrolyte between the blood of a patient and a dialysate fluid is described. The dialysis device is capable of being used for hemodialysis or peritoneal dialysis, and the dialysis device is capable of operation with a dialysate purification unit outside of a clinical setting or with a supply of water that can be supplied in a clinical setting. The dialysis device has a composition sensor containing a potassium-sensitive electrode for measuring a potassium ion concentration in one or more of the patient's blood and the dialysate fluid and an infusate pump operated to adjust a potassium ion concentration in the dialysate fluid based at least in part on data from the composition sensor.

23 Claims, 52 Drawing Sheets

Related U.S. Application Data continuation-in-part of application No. 13/424,490, filed on Mar. 20, 2012, and a continuation-in-part of application No. 13/424,517, filed on Mar. 20, 2012, and a continuation-in-part of application No. 13/424,479, filed on Mar. 20, 2012, and a continuation-in-part of application No. 13/424,533, filed on Mar. 20, 2012, and a continuation-in-part of application No. 13/451,395, filed on Apr. 19, 2012.

(60) Provisional application No. 61/480,528, filed on Apr. 29, 2011, provisional application No. 61/480,530, filed on Apr. 29, 2011, provisional application No. 61/480,532, filed on Apr. 29, 2011, provisional application No. 61/480,535, filed on Apr. 29, 2011, provisional application No. 61/480,541, filed on Apr. 29, 2011, provisional application No. 61/480,539, filed on Apr. 29, 2011.

(51) Int. Cl.

| | | |
|---|---|---|
| *A61M 1/16* | (2006.01) | |
| *A61M 1/34* | (2006.01) | |
| *A61B 5/145* | (2006.01) | |
| *B01D 61/32* | (2006.01) | |
| *B01D 65/02* | (2006.01) | |
| *B01D 61/24* | (2006.01) | |
| *B01D 61/30* | (2006.01) | |
| *A61B 5/0452* | (2006.01) | |
| *A61B 5/0488* | (2006.01) | |
| *A61M 1/36* | (2006.01) | |
| *A61B 5/026* | (2006.01) | |
| *A61B 5/053* | (2006.01) | |
| *A61B 5/021* | (2006.01) | |

(52) U.S. Cl.
CPC ............... *A61B 5/6866* (2013.01); *A61M 1/16* (2013.01); *A61M 1/1601* (2014.02); *A61M 1/1696* (2013.01); *A61M 1/342* (2013.01); *A61M 1/3609* (2014.02); *B01D 61/243* (2013.01); *B01D 61/30* (2013.01); *B01D 61/32* (2013.01); *B01D 65/02* (2013.01); *A61B 5/0031* (2013.01); *A61B 5/021* (2013.01); *A61B 5/026* (2013.01); *A61B 5/0537* (2013.01); *A61B 2560/0223* (2013.01); *A61M 2205/18* (2013.01); *A61M 2205/3334* (2013.01); *A61M 2205/3553* (2013.01); *A61M 2205/3584* (2013.01); *A61M 2205/3592* (2013.01); *A61M 2205/52* (2013.01); *A61M 2205/70* (2013.01); *A61M 2230/005* (2013.01); *A61M 2230/04* (2013.01); *A61M 2230/208* (2013.01); *A61M 2230/60* (2013.01); *B01D 2311/246* (2013.01); *B01D 2321/12* (2013.01); *B01D 2321/40* (2013.01)

(56) References Cited

U.S. PATENT DOCUMENTS

| | | | |
|---|---|---|---|
| 5,127,404 | A | 7/1992 | Wyborny et al. |
| 5,305,745 | A * | 4/1994 | Zacouto ........................ 600/324 |
| 5,683,432 | A | 11/1997 | Goedeke et al. |
| 7,674,231 | B2 | 3/2010 | McCombie et al. |
| 2011/0066043 | A1 * | 3/2011 | Banet et al. .................... 600/485 |
| 2012/0273415 | A1 | 11/2012 | Gerber et al. |
| 2012/0273420 | A1 | 11/2012 | Gerber et al. |
| 2012/0277604 | A1 | 11/2012 | Gerber et al. |
| 2012/0277650 | A1 | 11/2012 | Gerber et al. |
| 2012/0277655 | A1 | 11/2012 | Gerber et al. |
| 2012/0277722 | A1 | 11/2012 | Gerber et al. |
| 2015/0080682 | A1 | 3/2015 | Gerber et al. |
| 2015/0088047 | A1 | 3/2015 | Gerber et al. |
| 2015/0151033 | A1 | 6/2015 | Gerber et al. |

OTHER PUBLICATIONS

Hemametrics, Crit-Line Hematocrit Accuracy, 2003, 1-5, vol. 1, Tech Note No. 11 (Rev. D).

Siegenthalar, et al., Pulmonary fluid status monitoring with intrathoracic impedance, Journal of Clinical Monitoring and Computing, 2010, 449-451:24.

Wang, Fundamentals of intrathoracic monitoring in heart failure, Am. J. Cardiology, 2007, 3G-310:Suppl.

Zhong, et. al., Miniature urea sensor based on H(+)-ion sensitive field effect transistor and its application in clinical analysis, Chin. J. Biotechnol., 1992, 57-65, 8(1).

Brynda, et. al., The detection of human β2-microglobulin by grating coupler immunosensor with three dimensional antibody networks, Biosensors & Bioelectronics, 1999, 363-368, 14(4).

Nedelkov, et. al., Design of buffer exchange surfaces and sensor chips for biosensor chip mass spectrometry, Proteomics, 2002, 441-446, 2(4).

* cited by examiner

MULTIMODAL DIALYSIS SYSTEM

FIELD OF THE INVENTION

The invention relates to medical devices and systems that can provide dialysis treatment for a mammal as a stand-alone system or as part of a medical facility. The devices and systems can perform hemodialysis, hemofiltration, hemodiafiltration or peritoneal dialysis. The devices and systems include an electrodialyzer, chemical sorbents, electronic sensors, an electronic controller and a flow control apparatus. The invention further relates to methods for performing dialysis using the described devices and systems to remove toxins from body fluids.

BACKGROUND

During operation of typical dialysis machines performing hemodialysis, blood is passed through a dialysis chamber on one side of a dialysis membrane and a dialysate is passed on the other side of the dialysis membrane. In addition to diffusion of solutes across the dialysis membrane, a difference in pressure between the blood-side and the dialysate-side of the dialysis membrane drives the bulk movement of water from higher pressure to lower pressure. The pressure generated on a particular side of the dialysis membrane depends on several factors including flow rate, viscosity of the fluid, geometry of the dialyzer and physiological condition of the patient. The diffusion of impurities from the blood, across the dialysis membrane and into the dialysate is thermodynamically driven by the concentration gradient difference between the concentration of impurities in the blood and the concentration of those species in the dialysate. In most dialysis systems, large volumes of water are required to form the dialysate thereby requiring patients to regularly travel to a dialysis center to receive treatment for a chronic disease. In effect, dialysis patients are tethered to their dialysis center.

Moreover, dialysis treatments performed at dialysis centers are administered intermittently and fail to replicate the continuous waste removal aspect of a natural and functioning kidney. Once a dialysis session is completed, fluid and other substances such as sodium and potassium salts immediately begin to accumulate in the tissues of the patient. Notwithstanding the benefits of dialysis, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles continuous kidney function. However, the requirement for patients to travel to the dialysis centers and the costs associated with the hemodialysis procedure itself pose an upper limit on the frequency of dialysis procedures.

Known attempts to make portable dialysis systems usually rely upon the regeneration of spent dialysate (i.e. dialysate having urea and/or other impurities therein) to form refreshed dialysate that can be reused to perform dialysis. However, large quantities of water are required to reuse spent dialysate thereby limiting portability. Accumulated waste products and impurities must be removed from the spent dialysate, and the composition and pH of the regenerated dialysate must be regulated for physiological compatibility. Generally, regeneration of spent dialysate requires use of a sorbent cartridge through which spent dialysate is recirculated and regenerated. However, regenerated dialysate produced by known systems is subject to variations in pH and sodium concentrations non-conducive to physiological norms. Further, zirconium-based exchange materials used in many known sorbent systems are expensive and can release ions into the dialysate that affect conductivity and/or the pH of the dialysate, which necessitates the addition of further reagents to the dialysate to maintain the composition of the dialysate.

Hence, there is a need for a convenient dialysis system that can regenerate dialysate in a cost-effective manner. The system should remove impurities from spent dialysate solution. The system should have a weight and volume that is sufficiently light and small to be practicably carried by the patient while ambulatory. There is a need for a system that would allow a patient to travel wherein the system is no larger than about the size of luggage suitable for storage in an overhead bin of an airplane. Further, to facilitate regular usage, the system should be conducive to operation by a patient without the assistance of a medical professional.

There is also a need for a system that can be quickly set up in a new location without requiring specific sources of water or new water lines or pipes. The system must be patient-friendly and capable of operating on a small volume of dialysate and suitable for daily use, continuous use, short-term use, or use in a home-setting. There is also a need for a modular system that can provide any one or combination of hemodialysis, hemofiltration, hemodiafiltration and peritoneal dialysis.

SUMMARY OF THE INVENTION

The invention is directed to a semi-portable, multimodal medical device/apparatus for dialysis. Related medical systems and methods for dialysate regeneration are provided herein.

In one or more embodiments, a multimodal dialysis apparatus is provided for non-invasively monitoring serum potassium concentration in a subject undergoing a dialysis treatment. In any embodiment, the multimodal dialysis apparatus includes an extracorporeal flow path for transporting blood of a subject to a hemodialysis unit; at least one of an electrocardiogram sensor and an electromyogram sensor for detecting a change in muscle activity or nerve activity of the subject and for producing at least one electrical signal based on the change in muscle activity or nerve as detected, the electrical signal being indicative of a serum potassium concentration; a dialysate flow path for transporting a dialysate fluid to the hemodialysis unit; and an infusate pump in potassium communication with the dialysate flow path such that the infusate pump is controlled to adjust a potassium concentration in the dialysate flow path based at least in part on the serum potassium concentration obtained via the at least one of the electromyogram sensor and the electrocardiogram sensor.

In any embodiment, the multimodal dialysis apparatus may further include a pulse generator for producing one or more pulse sets; and one or more detectors or pulse-sensing electrodes for sensing the response of the subject to the pulse generator, wherein the one or more detectors include at least one of a nerve electrogram amplifier, an accelerometer, a strain gauge, and a pressure gauge for detecting the change in muscle activity. The one or more detectors may mediate communication between the pulse generator and the subject, such that the change of muscle activity in the subject is initiated by the one or more pulse sets and mediated by the one or more detectors.

In any embodiment, the medical device of the multimodal dialysis apparatus may be externally applicable to or implantable in the subject.

In any embodiment, the pulse generator of the multimodal dialysis apparatus may be provided with a pulsing schedule such that the one or more pulse sets include a first pulse set and a second pulse set, the first and second pulse sets are produced according to one or more of the following pulsing rules: i) the first and second pulse sets are separated in time by 0.5 to 5 seconds; ii) the first and second pulse sets each independently include 3 to 10 pulses; and iii) the first and second pulse sets each independently having a frequency of 2 to 50 Hz.

In any embodiment, the pulsing schedule of the pulse generator of the multimodal dialysis apparatus may be provided such that the first and second pulse sets are produced according to two or more of the following pulsing rules: i) the first and second pulse sets are separated in time by 1.5 to 2.5 seconds; ii) the first and second pulse sets each independently include 4 to 6 pulses; and iii) the first and second pulse sets each independently having a In any embodiment, the of 2 to 10 Hz.

In any embodiment, the multimodal dialysis apparatus may further include an amplifier mediating communication between the pulse generator and the one or more pulse-sensitive electrodes.

In any embodiment, the electromyogram sensor of the multimodal dialysis apparatus may include a skeletal muscle strain sensor and/or a blood pressure sensor.

In any embodiment, the electromyogram sensor can be a nerve electrogram sensor.

In any embodiment, the electrocardiogram sensor of the multimodal dialysis apparatus may include one or more electrocardiogram electrodes for receiving one or more electrocardiogram features from the subject, the one or more electrocardiogram features including T-wave amplitude, R-wave amplitude, T-slope, ratio of T-wave amplitude to R-wave amplitude (T/R ratio), and T-wave flatness.

In any embodiment, the multimodal dialysis apparatus may further include an electrocardiogram algorithm for producing an output on serum potassium concentration in the subject based on a value of the one or more electrocardiogram features, wherein the electrocardiogram algorithm includes one or more of the following operational rules: i) the output on the serum potassium concentration being a function of the R-wave amplitude; ii) the output on the serum potassium concentration being a function of the T-wave amplitude; iii) the output on the serum potassium concentration being a function of the T/R ratio; and iv) the output on the serum potassium concentration being a function of the T-wave flatness.

In any embodiment, the output on the serum potassium concentration provided via the ECG algorithm of the multimodal dialysis apparatus may be a difference between a serum potassium concentration at time $t_1$ of the subject and a baseline potassium concentration at time $t_0$ of the subject, time $t_1$ being at least 10 minutes apart from $t_0$. The baseline serum potassium concentration may be a value selected from the group consisting of a baseline serum potassium concentration of the subject obtained at a periodic blood draw, a baseline serum potassium concentration of the subject obtained at the onset of a dialysis session, and a baseline serum potassium concentration of the subject at the end of a dialysis session.

In any embodiment, the baseline potassium concentration of the subject may be 3.0 to 5.5 mM at time $t_0$.

In any embodiment, the R-wave amplitude of operational rule i) as provided via the ECG algorithm of the multimodal dialysis apparatus may be a difference between an R-wave amplitude at time $t_1$ of the subject and a baseline R-wave amplitude at time $t_0$ of the subject, the T-wave amplitude of operational rule ii) as provided via the ECG algorithm of the multimodal dialysis apparatus may be a difference between a T-wave amplitude at time $t_1$ of the subject and a baseline T-wave amplitude at time $t_0$ of the subject, the T/R ratio of operational rule iii) as provided via the ECG algorithm of the multimodal dialysis apparatus may be a difference between a T/R ratio at time $t_1$ of the subject and a baseline T/R ratio at time $t_0$ of the subject, and the T-wave flatness of operational rule iv) as provided via the ECG algorithm of the multimodal dialysis apparatus may be a difference between an T-wave flatness at time $t_1$ of the subject and a baseline T-wave flatness at time $t_0$ of the subject.

In any embodiment, the one or more electrocardiogram electrodes as non-limiting examples of the electrocardiogram sensors may include one or more of lead II, lead V2, lead V3 and lead V4.

In any embodiment, the one or more electrocardiogram electrodes as non-limiting examples of the electrocardiogram sensors may consist of lead II only.

In any embodiment, the electrocardiogram algorithm may include only one or more of the operational rules i), iii) and iv).

In any embodiment, the output on the serum potassium concentration as provided via the ECG algorithm of the multimodal dialysis apparatus may be in positive correlation with the R-wave amplitude.

In any embodiment, the output on the serum potassium concentration as provided via the ECG algorithm of the multimodal dialysis apparatus may be in negative correlation with the T-wave amplitude.

In any embodiment, the output on the serum potassium concentration as provided via the ECG algorithm of the multimodal dialysis apparatus may be in negative correlation with the T-slope.

In any embodiment, the output on the serum potassium concentration as provided via the ECG algorithm of the multimodal dialysis apparatus may be in positive correlation with the T-wave flatness.

In any embodiment, the one or more electrocardiogram electrodes may include a first set of electrodes consisting of lead II, lead V2, lead V3 and lead V4, and a second set of electrodes consisting of lead II only, wherein the electrocardiogram algorithm further includes a calibration rule that the multimodal dialysis apparatus is operationally calibrated if one or more of the following is met: v) a difference between the outputs according to rule ii) from the first set of electrodes and the second set of electrodes is no greater than 20%; vi) a difference between the outputs according to rule iii) from the first set of electrodes and the second set of electrodes is no greater than 20%; and vii) a difference between the outputs according to rule iv) from the first set of electrodes and the second set of electrodes is no greater than 20%.

In any embodiment, the one or more electrocardiogram electrodes may include a first set of electrodes consisting of lead II, lead V2, lead V3 and lead V4, and a second set of electrodes consisting of lead II only, wherein the electrocardiogram algorithm further includes a calibration rule that the multimodal dialysis apparatus is operationally calibrated if one or more of the following is met: v) a difference between the outputs according to rule ii) from the first set of electrodes and the second set of electrodes is no greater than 10%; vi) a difference between the outputs according to rule iii) from the first set of electrodes and the second set of electrodes is no greater than 10%; and vii) a difference between the outputs according to rule iv) from the first set of electrodes and the second set of electrodes is no greater than 10%.

In any embodiment, the multimodal dialysis apparatus may further include one or more potassium-sensitive electrodes for measuring a potassium ion concentration in the dialysate flow path.

In any embodiment, the present invention in one or more embodiments further provides a method for conducting a dialysis treatment in a subject while the serum potassium concentration of the subject may be non-invasively monitored. According to the method, the dialysis treatment may be conducted with an extracorporeal flow path for transporting blood of the subject to a hemodialysis unit, a dialysate flow path for transporting a dialysate fluid to the hemodialysis unit, and an infusate pump in potassium communication with the dialysate flow path.

In any embodiment, the method includes: applying to the subject one or more pulse sets generated by a pulse generator; connecting at least one electromyogram sensor to the subject to receive at least one electrical signal from the subject in response to the one or more pulse sets; and generating an output from the at least one electromyogram sensor in response to the at least one electrical signal, the output being indicative of a level of serum potassium concentration of the subject; and adding an amount of potassium via the infusate pump into the dialysate flow path, wherein the amount of potassium is determined based at least in part on the serum potassium concentration obtained via the at least one of the electromyogram sensor and the electrocardiogram sensor. The one or more pulse set may be generated as detailed herein elsewhere.

In any embodiment, the method includes: connecting at least one electrocardiogram sensor to a subject to receive one or more electrocardiogram features; applying an electrocardiogram algorithm to the one or more electrocardiogram features to obtain an indicator for serum potassium concentration of the subject, wherein the electrocardiogram algorithm includes one or more of the following operational rules: i) the output on the serum potassium concentration being a function of the R-wave amplitude; ii) the output on the serum potassium concentration being a function of the T-wave amplitude; iii) the output on the serum potassium concentration being a function of the T/R ratio; and iv) the output on the serum potassium concentration being a function of the T-wave flatness; and adding an amount of potassium via the infusate pump into the dialysate flow path, wherein the amount of potassium is determined based at least in part on the serum potassium concentration obtained via the at least one of the electromyogram sensor and the electrocardiogram sensor.

Figure 1:
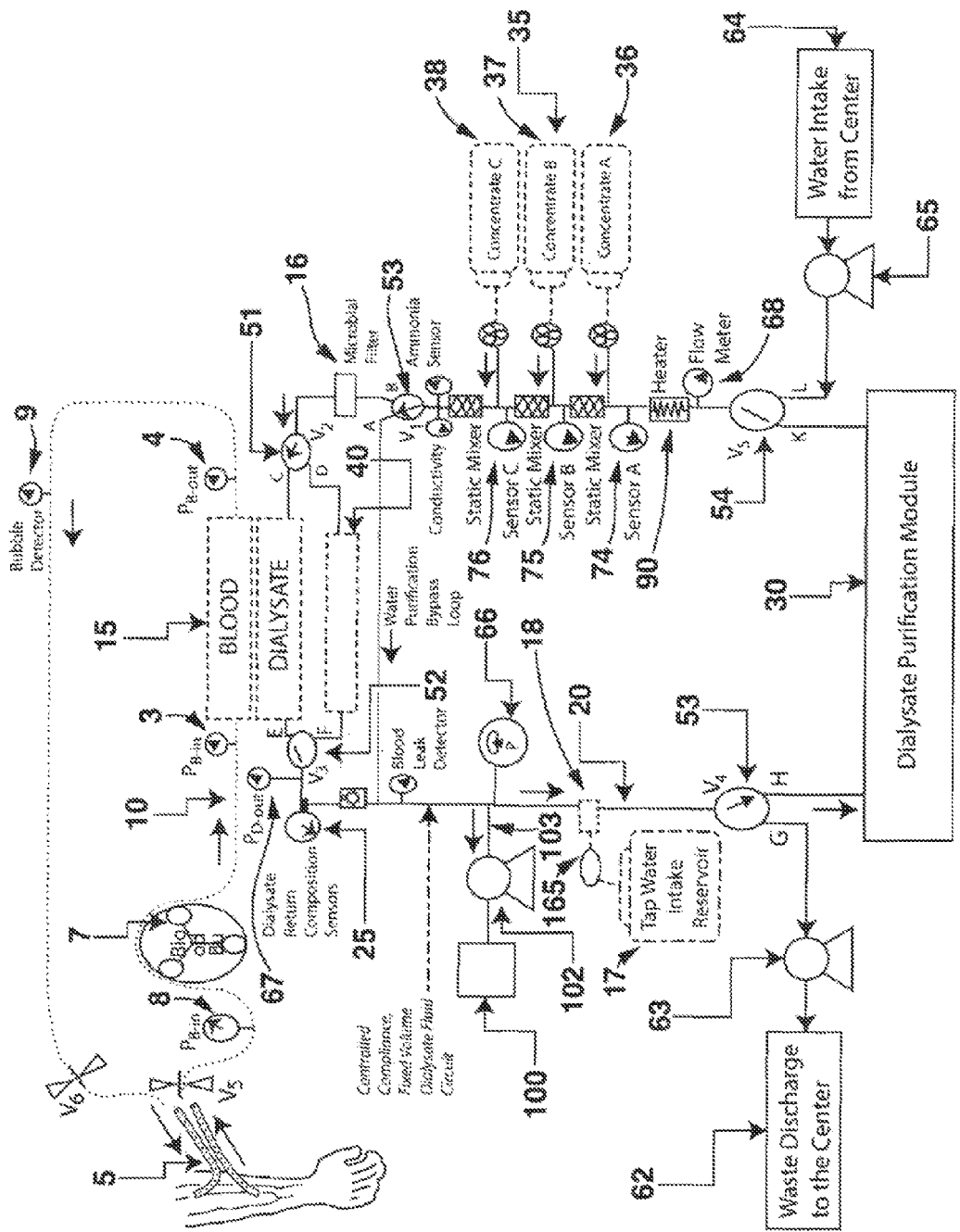
FIG. 1 shows an exemplary embodiment of the invention employed for hemodialysis treatment.

Like reference numbering between FIG.'S represents like features and elements.

DETAILED DESCRIPTION OF THE INVENTION

Unless defined otherwise, all technical and scientific terms used herein generally have the same meaning as commonly understood by one of ordinary skill in the relevant art. The definitions provided herein should not be rigidly construed without taking into account the context and other ascribed meanings provided, or by their use, in other parts of the specification, claims, and drawings.

The articles "a" and "an" are used herein to refer to one or to more than one (i.e., to at least one) of the grammatical object of the article. By way of example, "an element" means one element or more than one element.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail completely.

The terms "communicate" and "communication" include but are not limited to, the connection of system electrical elements, either directly or remotely, for data transmission among and between said elements. The terms also include, but are not limited to, the connection of system fluid elements enabling fluid interface among and between said elements.

The term "anode" refers to the positively charged electrode.

The term "cathode" refers to the negatively charged electrode.

The term "anion" refers to negatively charged particles that are attracted toward the positive electrode, i.e. anode.

The term "cation" refers to positively charged particles that are attracted toward the negatively charged electrode, i.e. cathode.

The term "electrodialysis" refers to the process of selectively moving electrically charged particles in a solution using externally applied electrical fields and ion selective membranes.

The term "reverse osmosis" refers to the process of selective removal of solutes from a solution with the application of external forces and the use of special membranes.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

A "control system" consists of combinations of components that act together to maintain a system to a desired set of performance specifications. The performance specifications can include sensors and monitoring components, processors, memory and computer components configured to interoperate.

A "controller" or "control unit" is a device which monitors and affects the operational conditions of a given system. The operational conditions are typically referred to as output variables of the system, which can be affected by adjusting certain input variables.

The term "dialysate" describes a fluid into which solutes from a fluid to be dialyzed diffuse through a membrane.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed.

A "dialysis chamber," "hemodialyzer" and "hemodialysis chamber" as used herein is a chamber in which hemodialysis is performed. If no dialysate is present, the dialysis chamber can be used for the bulk transfer of water using a pressure gradient. In that case, the chamber can function as a "hemofiltration chamber." Similarly, if both hemodialysis and hemofiltration, the chamber can function as a "hemodiafiltration chamber."

An "electrodialysis unit" as used herein is a fluid processing unit that removes waste components from effluent dialysate by altering the ionic composition of a fluid. Such units may include electrically conductive plates separated by ion-exchange membranes. Fluid flowing between the plates is exposed to an electrical field. The electrical field induces a rate of ion movement within the fluid corresponding to the magnitude of the voltage potential formed between the electrically conductive plates.

A "dialysate cleansing unit" as used herein is a fluid processing unit that removes waste components from effluent dialysate via sorbent adsorption, electrodialysis, reverse osmosis or similar techniques.

The term "hyperosmotic" pertains to a solution that has a higher solute concentration than another solution. In the human body, a hyperosmotic state refers to a condition caused by the accumulation in the body of significant quantities of osmotically active solutes.

The term "hypoosmotic" pertains to a solution containing a lower concentration of osmotically active components than a standard solution. In the human body, a hypoosmotic state describes a cell that has a lower concentration of solutes than its surroundings.

Osmolarity is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

A "subject" or "patient" is a member of any animal species, preferably a mammalian species, optionally a human. The subject can be an apparently healthy individual, an individual suffering from a disease, or an individual being treated for a disease.

The term "programmable" as used herein refers to a device using computer hardware architecture and being capable of carrying out a set of commands, automatically.

The term "sensory unit" refers to an electronic component capable of measuring a property of interest.

The terms "treating" and "treatment" refer to the management and care of a patient having a pathology or condition. Treating includes administering one or more embodiments of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "dialyzer" or "hemodialysis unit" refers to a cartridge or container with two flow paths separated by semipermeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

The terms "dialysate flow loop", "dialysate flow path", and "dialysate conduit flow path" refers, in context, to a fluid pathway that conveys a dialysate and is configured to form at least part of a fluid circuit for hemodialysis, hemofiltration, hemodiafiltration or ultrafiltration.

The term "extracorporeal," as used herein generally means situated or occurring outside the body.

The term "extracorporeal circuit" refers to a fluid pathway incorporating one or more components such as, but not limited to, conduits, valves, pumps, fluid connection ports or sensing devices configured therein such that the pathway conveys blood from a subject to an apparatus for hemodialysis, hemofiltration, hemodiafiltration or ultrafiltration and back to the subject.

The term "flow path" refers to a route or a collection of routes for a fluid to move within. Within a flow path there may be more than one route that a fluid can follow to move from a first position to a second position. A fluid may move through a flow path such that it recirculates, or passes the same position more than once as it moves through a flow path. A flow path may be a single element such as a tube, or a flow path may be a grouping of components of any type that guide the movement of a fluid. The term "flow loop" and "flow path" often may be used interchangeably. Further types of flow paths may be further defined; for example, (1) a recirculation flow path, would be a flow path whose function is in whole or part is to recirculate fluid through the defined flow path; (2) a dialyzer recirculation flow path would be a flow path whose function is in whole or part is to recirculate fluid through the defined flow path having a dialyzer' (3) a controlled compliant flow path would be a flow path would be a flow path that is controlled compliant as defined herein. Any of the defined flow paths may be referred to numerically, as a first flow path, second, third flow path, or fourth flow path, and the like flow paths.

Electrocardiogram or ECG is a time varying waveform, produced by the electrical activity of the cardiac muscle and the associated electrical network within the myocardium. Term is used interchangeably for the tracing that is available from the surface of the subject, or from an implantable or external device.

The term "P-R interval" refers to the length of time from the beginning of the P wave to the beginning of the QRS complex.

The term "QRS width" refers to the length of time of the QRS complex.

The term "Q-T interval" refers to the length of time from the beginning of the QRS complex to the end of the T-wave.

The term "Q-T dispersion" refers to the difference between the maximum and minimum QT intervals measured in a time period.

The term "P-wave amplitude" refers to the maximum potential reached by the P-wave.

The term "T-wave amplitude" refers to a numerical measurement of the magnitude of the portion of the electrocardiographic representation of the repolarization of the ventricles of the heart.

The term "R-wave amplitude" refers to a numerical measurement of the magnitude of the portion of the electrocardiographic signal corresponding to the depolarization of the ventricles of the heart.

The term "T-slope" refers to a numerical measurement corresponding to the slope of the line drawn from the peak of the T-wave to the end of the T-wave. The end of the T wave is defined as the intercept between the isoelectric line with the tangent drawn through the maximum down slope of the T wave.

The term "ratio of T-wave amplitude to R-wave amplitude (T/R ratio)" refers to the numerical ratio of the T-wave amplitude to the R-wave amplitude.

The term "T-wave flatness" refers to a numerical representation of the degree that an electrocardiographic T-wave has a low amplitude and is more spread out and less peaked.

The term "P-wave peak" refers to the rate of change in the P wave in units of potential change per unit time.

The term "S-T segment" refers to the interval between the QRS complex and the beginning of the T wave. S-T segment is depressed if it has a downward concavity.

The term "T wave" refers to the wave after the QRS complex and the S-T segment. An inverted T wave has a negative amplitude.

The term "U wave amplitude" refers to the maximum potential of a wave that follows the T wave. The U wave is not always observed in a cardiac cycle.

The term "hypokalemia" refers to a physiological state wherein the concentration of potassium ions in the blood serum or interstitial fluid is less than the normal physiological range of 3.5 to 5 mEq/L.

The term "hyperkalemia" refers to a physiological state wherein the concentration of potassium ions in the blood serum or interstitial fluid is more than the normal physiological range of 3.5 to 5 mEq/L.

The term "electromyogram sensor" refers to a device for sensing the electrical or mechanical activity produced as a result of the voluntary or stimulated contraction of skeletal muscles of the body.

The term "electrocardiogram sensor" refers to a device for sensing of the electrical activity of the heart. It typically consists of a set of electrodes along with associated electronics. Electrodes may be applied directly to the skin or can be part of an implanted device.

The term "serum potassium concentration" in certain instances refers to "blood potassium concentration".

The term "pulse generator" refers to an electronic circuit which generates electrical pulses in accordance with a predetermined sequence, to be delivered through electrodes to an external load, typically an organ such as a skeletal muscle, heart or nerve tissue. In certain instances, a pulse generator is or includes an electrical pulse generator.

The term "pulse-sensing electrodes" refers to devices which can detect the presence of electrical or mechanical activity of the tissue, such as the skeletal muscle or nerves, and convert them into electrical signals.

The term "pulsing schedule" refers to a particular scheme of delivering electrical pulses at specified times, frequencies, and amplitudes.

The term "amplifier" refers to an electronic device that increases the power of a signal and provides impedance matching. It can be used to increase the voltage and/or current produced by the pulse generator, which in turn is delivered to the tissue.

The term "skeletal muscle strain sensor" refers to a device which detects the changes in the strain of an artificial device as a result of changes in the contractile tone of a skeletal muscle. Output of this transducer is usually an electrical voltage or a current that is proportional to either the absolute value of the strain or to the changes in the strain.

The term "blood pressure sensor" refers to a sensor designed to detect the pressure changes within a pressure cuff worn around an extremity, such as an arm or a leg. Analysis of the pressure waveform produces the signals correlating to the changes in the contractile tone of a skeletal muscle as well as the information relating to the blood pressure such as the diastolic and systolic blood pressure and heart rate.

The term "lead II" refers to the electrocardiographic voltage signal between the left leg electrode and the right arm electrode.

The term "lead V2" refers to the electrocardiographic voltage signal between an electrode located in the fourth intercostal space (between ribs 4 and 5) just to the left of the sternum, and Wilson's central terminal, which is the average of the three limb leads (I, II, and III). Leads I, II and III are the voltages between the left arm and right arm electrode, between the left leg and right arm, and between the left leg and left arm electrode, respectively.

The term "lead V3" refers to the electrocardiographic voltage signal between an electrode located centrally between the V2 and V4 electrodes, and Wilson's central terminal, which is the average of the three limb leads (I, II, and III). Leads I, II, and III are the voltages between the left arm and right arm electrode, between the left leg and right arm, and between the left leg and left arm electrode, respectively.

The term "lead V4" refers to the electrocardiographic voltage signal between an electrode located in the fifth intercostal space (between ribs 5 and 6) in the mid-clavicle line, and Wilson's central terminal, which is the average of the three limb leads (I, II, and III). Leads I, II and III are the voltages between the left arm and right arm electrode, between the left leg and right arm, and between the left leg and left arm electrode, respectively.

The term "waste components" as used herein describe waste organic and inorganic components, such as urea, uric acid, creatinine, chlorides, inorganic sulfate and phosphate. Specific "waste components" can vary between individual depending on diet and environmental factors. Hence, the term is intended to encompass any waste component that is normally removed by a kidney or by dialysis without restriction on the specific type of waste substance.

A "portable dialyzer" is a portable artificial dialysis device through which blood is circulated, the dialyzing fluid being regenerated by a system of filters and make-up solids continuously fed to the dialysis fluid. The device may be a continuously operable and externally regenerable dialysis device that is capable of concurrently dialyzing the bodily fluids and regenerating the dialysis fluid outside the body.

Dialysate Regeneration

Dialysate fluid used for hemodialysis contains many of the solutes that are found in body fluids as shown in Table 1. Dialysate fluid used for peritoneal dialysis is similar except $HCO_3^-$ is replaced with lactate at similar concentrations and dextrose is used at much higher concentrations around 2000 mg/dl.

TABLE 1

Typical solute concentrations in dialysate for hemodialysis

| Solute | Concentration |
| --- | --- |
| Na | 137 mEq/L |
| Cl | 105 mEq/L |
| Ca | 3.0 mEq/L |
| Acetate | 4.0 mEq/L |
| K | 2.0 mEq/L |
| HCO3 | 33 mEq/L |
| Mg | 0.75 mEq/L |
| Dextrose | 200 mg/dl |

The concentrations of the solutes to be removed from the body are lower in the dialysate than in the bodily fluid. For example, the concentration of potassium ion ($K^+$) is typically about 2 mM in the dialysate, while the concentration in the bodily fluid, such as blood, is usually higher, perhaps at about 5 mM. Hence, the mass transfer from the body fluids to the dialysate causes the concentrations of these molecules to increase in the dialysate during a treatment session. The present system removes impurities from dialysate.

Impurities in the fluid dialysate come in two forms: ionic substances and non-charged substances. Ions readily dissolve in water due to the polar nature of water wherein the separation of the ions from the water requires special processes. In particular, removal of ions in the present invention may be accomplished by ion exchange columns, sorbents, electrodialysis, distillation, reverse-osmosis as well as other means known to those of ordinary skill. In particular, electrodialysis and sorbents can be used for the removal of charged ions from the used dialysate in the present invention. However, non-charged or neutral molecules such as urea are generally ineffectively removed from water using electrodialysis unless such non-charged substances are first converted into a charged ionic substance. In certain embodiments, the systems and devices of the present invention remove at least a portion of the daily build-up of 20 grams of urea, 2 grams of creatinine, 4 grams of sodium, 2 grams of potassium and 1 gram of phosphorus, in addition to a few liters of water due to fluid build-up caused by CKD.

In certain embodiments, the present invention employs an electrodialysis unit to remove waste species from the dialysate after treatment. After initial contact between the dialysate and the patient to remove one or more waste species from the patient, the generated spent dialysate is regenerated to remove waste species and/or rebalance dialysate to maintain a composition to allow for proper mass transfer between the patient and the dialysate. In particular, the electrodialysis unit is used as part of a system in certain embodiments to regenerate dialysate for reuse without the primary use of sorbent materials for absorbing urea, ammonia or ammonium ions, such as zirconium phosphate and other zirconium-containing sorbents. In some embodiments, a sorbent material containing zirconium or zirconium can be present, however the use and/or amount of the consumable sorbent material is substantially reduced due to the presence of the electrodialysis unit. The fluid generated by the electrodialysis unit or a purification unit is substantially free from ionic material wherein a dialysate can be regenerated through the addition of buffers, salts and osmotic agents. An activated carbon sorbent can optionally be used to remove common non-ionic waste species such as creatinine. A urease-containing material can be used to convert neutral urea to ammonium ions that are removed by the electrodialysis unit.

The electrodialysis unit can be used in a multimodal fashion for hemodialysis, hemodiafiltration, or peritoneal dialysis. In some embodiments, an extracorporeal or blood circuit passes blood from a patient through a hemodialyzer while a dialysis circuit passes a dialysate through the same hemodialyzer such that waste species pass from the blood to the dialysate to generate spent dialysate. The spent dialysate can then be regenerated for reuse and reentry into the dialysate circuit after treatment with the electrodialysis unit for use in hemodialysis. In other embodiments, a spent dialysate that has been contacted with the peritoneal membrane of a patient is regenerated though use of the electrodialysis unit to remove waste components from the dialysate. Then, the regenerated dialysate can be re-contacted with the peritoneal membrane of the patient to continue peritoneal dialysis.

The invention also provides for an easily portable dialysis system that can be transported to a clinical dialysis center, herein referred to as in-center use or mode. The embodiments of the invention are adaptable to operate with a substantially fixed volume of dialysate wherein the dialysate is continually cleaned by a purification unit and reconstituted to form dialysate and can also operate in a mode wherein dialysate can be generated from purified water provided from a clinical dialysis center (in-clinic mode) without the need for a purification module to clean the dialysate.

Hemodialysis

FIG. 1 shows an exemplary embodiment employing the electrodialysis unit 30 of the invention. A vascular access 5 provides an access to the blood of a patient for extracorporeal processing and return to the patient. The vascular access 5 can be a fistula, a shunt, a catheter or any device or method that allows the transfer of blood between the patient and an extracorporeal system.

The extracorporeal system has a blood loop or circuit 10 consisting of tubing, a blood pump 7 as well as connectors to connect the tubing to the vascular access 5 and to a dialyzer 15. Dialyzer 15 is generally an exchange chamber where fluids and solutes can readily cross a membrane separating the extracorporeal blood and the dialysate. During hemofiltration operation, dialysate is not present on the dialysate side wherein bulk transfer of water takes place under a pressure gradient across a membrane. In certain embodiments, the membrane of dialyzer 15 can be any of a number of hollow fiber-type structures known in the art.

Blood pump 7 can be a peristaltic pump or any other suitable pump known to those of ordinary skill. Sensors in the blood loop or circuit 10 can be used to measure the blood flow rate and the pressure of the blood at various points along the blood loop or circuit 10. One or more pressure sensors can be present to ascertain the pressure within the tubing at different points. In particular, pressure sensors can be present near the vascular access 5 and at the inlet 3 and outlet 4 of the dialyzer 15.

A dialysate loop 20 consists of tubing to carry the dialysate, and valves 51, 52, 53 and 54 direct the dialysate flow. Connectors to water intake 64 and connectors to a waste discharge 62 direct flow via pumps 63 and 65. Connections to a dialysate purification module 30 can also be present along with connectors to the dialyzer 15 and to a flow balance module 40 for diverting dialysate flow away from the dialyzer 15. One or more reservoirs containing an infusate concentrate as well as mixers and sensors 35 (collectively, infusion set) mixes an infusate concentrate with fluid present in the dialysate loop 20.

During hemodialysis operation, dialysate having a physiological compatible composition enters the dialyzer 15 wherein at least one waste component transfers from the blood in the blood circuit 10 to the dialysate circuit 20. The direction of dialysate flow through dialysate circuit 20 is indicated by arrows and the locomotive force for directing the dialysate is provided by pumps present in the electrodialysis unit 30. Valves 51, 52 and 53, located pre- and post-dialyzer 15 can control flow balance through the dialyzer 15. For example, if directing all of the circulation of the dialysis circuit 20 creates an undesirably large pressure within the dialyzer 15, part of the dialysate flow can be diverted through a flow balance unit 40 or a bypass loop 54. One or more sensors can be present along the dialysate circuit 20 to measure pressure and flow rates. FIG. 1 shows pressure sensors 66 and 67 for measuring pressure in the dialysate circuit 20 and flow meter 68 for measuring flow through the dialysate circuit 20.

The dialysate exiting the dialysis unit 15 contains at least one waste species and can be referred to as spent dialysate. The spent dialysate requires purification before being returned to the dialyzer 15. The dialysate purification module 30, which contains an electrodialysis unit, removes ionic species, urea and other uremeic impurities from the dialysate. The fluid emerging from the purification module 30 is substantially deionized and debuffered. Before returning to the dialyzer 15, the fluid is treated by infusion set 35 to add necessary buffer, salts and osmotic control solutes to regenerate a physiologically compatible dialysate. Part of the fluid from the dialysis circuit 20 entering the purification module 30 can be used for the purpose of removing ionic waste species from the purification module 30 and is not returned to the dialysis circuit 20. Water intake 64 and water intake pump 65 can replenish the volume within the dialysis circuit as required. However, a substantial amount of the fluid entering the purification module 30 is returned to the dialysis circuit 20.

In some embodiments, at least about 50% of the fluid entering the purification module 30 is purified for regeneration as dialysate. In other embodiments, at least about 55%, about 58%, about 60%, about 67%, about 70% about 75%, about 77%, about 83%, about 85%, about 89%, or about 95% of the fluid entering the purification module 30 is purified for regeneration as dialysate. In still other embodiments, at least about 97% of the fluid entering the purification module 30 is purified for regeneration as dialysate. In additional embodiments, at least about 99% of the fluid entering the purification module 30 is purified for regeneration as dialysate.

The infusate set 35 can regenerate an appropriate dialysate having a physiologically acceptable concentration of ionic solutes, buffering species as osmolarity. Infusate concentrate reservoirs 36, 37, and 38 can contain solutions for cation salts of $Ca^{2+}$, $Mg^{2+}$ and $K^+$ (typically chloride salts), a biocarbonate buffer and dextrose or other osmotic agent. In certain embodiments, a mixture of cation salts, buffer solution and dextrose are maintained in separate reservoirs, although in other embodiments the concentrates can be combined into fewer reservoirs. As will be further explained below, in some embodiments one of infusate concentrate reservoirs contains a potassium salt in one of reservoirs 37, 37 and 38 not combined with other salts or solutes. The rate of addition of concentrate from reservoirs 36, 37 and 38 can be controlled by pumps 71, 72 and 73. Since the fluid entering the dialysis circuit 20 is substantially solute-free water, in certain embodiments the concentrate solutions are added at a rate that depends upon the concentration of the infusate concentrates and the rate of flow of fluid through the dialysis circuit 20. In certain embodiments, the rate of addition of a potassium salt to the dialysis circuit 20 is adjusted to maintain a constant concentration gradient or rate of mass transfer from the extracorporeal circuit 10 to the dialysis circuit during treatment. Sensors, such as pH, conductivity and ion-selective sensors can be placed along the dialysate circuit 20 to verify that the dialysate has the proper final concentration. Static mixers 74, 75 and 76 can be present to ensure complete mixing of the infusate concentrates.

In certain embodiments, the dialysis circuit 20 can be a controlled compliance dialysis circuit. In addition to diffusion of solutes across the dialysis membrane, a difference in pressure between the blood-side and the dialysate-side of the dialyzer 15 can drive the bulk movement of water from higher pressure to lower pressure. The pressure generated on a particular side of the hemodialyzer depends on several factors including flow rate, viscosity of the fluid, geometry of the dialyzer and the physiological condition of the patient. Control of pressure and the subsequent net movement of water across the dialyzer 15, in general, requires large and expensive equipment to control with a high degree of accuracy. The controlled compliance dialysis circuit embodiment of the present invention provides a means to control the movement of water between the patient and the dialysis circuit 20 and vice versa. In particular, the total void volume of the conduits forming the dialysis circuit have a substantially inflexible volume that prevents the passive inflow and outflow of fluid volume due to pressure changes in the dialyzer 15 that can occur over the course of treatment. This results in a benefit because not all of the pressure changes during treatment are under precise control by a user or operator. That is, under conditions where there is higher pressure on the blood-side of the dialyzer 15, fluid is prevented from uncontrollably migrating into the dialysis circuit due to the controlled compliance volume of the dialysis circuit and water's nature as an uncompressible fluid. Likewise, under conditions where there is a higher pressure on the dialysis circuit 20 side of the dialyzer 15, water cannot uncontrollably migrate to the blood circuit 10 due to the vacuum within the dialysis circuit 20 that would otherwise be created.

Using the controlled compliance dialysis circuit 20 described herein, net movement of water across the dialyzer 15 occurs under active control rather than passively due to pressure differences that develop across the dialysis membrane due to normal operations. In the embodiment shown in FIG. 1, water supplied from intake 64 and pump 65 can be provided to maintain the primed state of the dialysis circuit 20 in the event that less than 100% of the fluid volume exits the purification unit 30 as compared to the fluid entering the purification unit 30. A control pump 102 can be present to access the controlled compliance dialysis circuit 20 through a conduit 103. The control pump 102 can be operated in a manner for controlling the compliance of the dialysis circuit for volume entering the dialysis circuit from the dialyzer 15, where such volume originates from the patient's blood and bodily fluids. The control pump 102 can be operated in an efflux direction that moves fluid from blood side of the dialyzer 15 to the dialysis circuit. That is, operation of the control pump 102 increases the compliance of the dialysis circuit to receive an influx of fluid volume that is moved to a reservoir or drain 100. Through such controlled compliance by control pump 102, net fluid can be removed from the patient to affect ultrafiltration. Due to fluid build-up that occurs in patients having KD, net removal of fluid by ultrafiltration is often desirable.

Similarly, a water intake pump 160 can be operated at a rate to provide an amount of fluid from a water intake 165 that replaces any loss of fluid occurring in the purification module 30. Any additional fluid beyond replacement added to the dialysis circuit 20 can cause a net movement of fluid volume from the control circuit 20 into the blood circuit 10 through the dialyzer 15. As such, the patient can be infused with fluid as need to address hypovolemia or other conditions.

In certain other embodiments, the control pump 102 can be operated at a rate from 0 to about 100 mL/min or 0 to 50 mL/min. Any range from about 0 to about 200 mL/min is contemplated by the invention such as about 15 to about 185 mL/min, about 25 to about 175 mL/min, about 5 to about 75 mL/min, about 61 to about 183 mL/min, about 156 to about 193 mL/min, about 32 to about 63 mL/min, about 145 to about 199 mL/min, about 16 to about 93 mL/min or, about 29 to about 124 mL/min.

All pumps and valves of the system can be under the control of an electronic controller to accurately control the net movement of fluids into and out of the dialysis circuit 20. For example, the electronic controller can control and monitor any pumping rate difference between the control pump 102 and the water intake pump 165 to calculate the net flow of fluid from the blood circuit 10 to the dialysis circuit 20 or from the dialysis circuit 20 to the blood circuit 10 via the dialyzer 15. The electronic controller can also exploit the controlled compliance properties of the dialysis circuit 20 to calculate the amount of fluid removed from the patient by ultrafiltration or infused into the patient during a treatment session. In this light, the electronic controller can also account for the volume added by the infusate set 35 or from the operation of pumps 63 and 65 when the system is operated without the benefit of the purification unit 30, as described herein.

Stand Alone Operation

For stand-alone operation outside of a clinical facility, dialysate flows through the dialysate purification unit 30 using the valves V4 (53) and V5 (54) because large volumes of fresh water or dialysate may not be available outside a clinical facility. In other embodiments, the dialysis circuit 20 can be used at a clinical facility where a supply of fresh dialysate or purified water is available. In such settings, water or dialysate can be introduced through valve 54 through use of pump 65, and after passing through the dialysis unit 15, the dialysate can be discarded at discharge 62 through the operation of pump 63. Furthermore, since the total dialysate volume is fixed during a stand-alone operation, flow balance unit 40 is not needed for standalone operation as may be needed for operation at a clinical center. Therefore, valves V2 [51] and V3 [52] are used to continuously force the dialysate flow over the dialysis unit 15. Table 2 below shows the settings of the valves for the stand-alone operation.

TABLE 2

Positions of valves for stand-alone operation

| Valve | Position |
|---|---|
| V2 | C |
| V3 | E |
| V4 | H |
| V5 | K |

In stand-alone operation, valves 51 and 52 are used to direct the dialysate flow through the dialysis unit 15. As explained in more detail below, during stand alone operation the control pump 102 and the drain/reservoir 100 may be located within the purification module 30 as shown in FIGS. 5-8.

Stand alone operation can also be performed for peritoneal dialysis, wherein the dialysis circuit 20 transports dialysate to and from the peritoneal cavity of a patient rather than a hemodialyzer. That is, the operative set-up for use in peritoneal dialysis mode is substantially the same as in FIG. 1, except the peritoneal cavity of the patient replaces the dialyzer 15 and the blood circuit 10 is not required.

Operation at a Dialysis Center

For operation at a dialysis center, water intake (or dialysate) from the clinical center 64, water intake pump 65, water discharge to the center 62 and the water discharge pump 63 can be present. Hence, there is no requirement for dialysate flow to go through the purification module 30 wherein valves V4 [63] and V5 [54] can be set to bypass the purification module 30.

Once the dialysate is pumped through one circuit of the dialysate circuit 20 by the pumps 63 and 65, there is a possibility that the total volume of dialysate may not be fixed due to a differential in flow rate between pumps 63 and 65. Specifically, any difference in the flow rates of the pumps 63 and 65 can result in the changes in the dialysate volume. Due to the controlled compliance properties of the dialysate circuit 20 described above for some embodiments, a change in dialysate volume will cause a net flow from the blood circuit 10, and hence fluid removal from the patient across the dialyzer 15 or vice versa. For example, if the pump 65 has a slightly higher rate of flow than the pump 63, then there will be surplus of fluid in the dialysate loop 20. This fluid will flow into the patient across the dialyzer 15 increasing the fluid content in the body of the patient. As such, hypovolemia of the patient can be directly addressed; however, fluid infusion of the patient is an undesirable in many scenarios since patients with kidney failure cannot effectively eliminate fluid. When the pump 65 has a flow rate lower than the pump 63, ultrafiltration and fluid removal from the patient can be achieved. However, care must be taken to avoid the removal of too much fluid from the patient.

In lieu of modification of the pump rates of pumps 65 and 63 to address fluid movement across the dialyzer 15, the above-described problem can be addressed using a flow balance module, where the dialysate flow is periodically shunted away from the hemodialysis unit 15 and instead forced to flow over a flow balance unit 40. With valves 51 and 52 actuated to allow access to the flow balance unit 40, no net flow from the dialysate loop 20 to blood loop 10 or vice versa occurs.

In particular, any difference in the flow rates of the pumps 63 and pump 65 would manifest itself as a change in the pressure as a function of time, which can be detected by the pressure sensor 66 when dialysate is flowing through flow balance unit 40. Dialysate can periodically be diverted through the flow balance unit 40 to verify that no difference in flow rates between pumps 63 and 65 is present and/or to make adjustments to the flow rates of pumps 63 and 65. In response to a measured change in pressure at pressure sensor 66, the electronic controller can adjust the power to the motors driving the pumps 63 and 65 to rectify any flow mismatch. For example, if the pressure measured by the pressure sensor 66 shows a trend upwards during the period when the dialysate is flowing over the flow balance unit 40, electronic controller can either reduce the power to the motor driving the pump 65 or increase the power to the motor driving the pump 63. Similarly, if a negative pressure trend is observed during the period when the dialysate is flowing over the flow balance unit 40, the electronic controller can be adjusted by either increasing the power to the motor driving the pump 65 or by decreasing the power to the motor driving the pump 63. In either case, the dialysate flow can be returned back to the dialyzer 15 from the flow balance unit 40 after periodic adjustment. Control pump 102 and drain/reservoir 100 can be present to perform ultrafiltration and fluid removal from the patient in the state where no flow rate difference exists between pump 63 and 65.

Therefore, valves V2 [51] and V3 [52] can be used to switch the dialysate flow between the dialyzer 15 and the flow balance unit 40, while valves V4 [53] and V5 [54] can maintain the dialysate flow bypassing the purification unit 30 for in-clinic operation. Furthermore, since the purification module 30 is not utilized, the control pump 100 and the reservoir/drain 102 can be employed as depicted in FIG. 1. Table 3 below shows the settings of the valves during in-clinic operation.

TABLE 3

Positions of valves for operation at a clinical center

| Valve | Position for dialysis | Position for flow balance |
|---|---|---|
| V2 | C | D |
| V3 | E | F |
| V4 | G | G |
| V5 | L | L |

Potassium Control

In certain embodiments, the concentration of potassium ions is actively controlled to maintain a steady gradient between the serum potassium concentration of the patient's blood and the potassium concentration of the dialysate introduced to the dialyzer 15. Due to the action of the sodium-potassium pump, the vast majority of potassium in the body is present intracellularly. However, dialysis, whether hemodialysis or peritoneal dialysis, can only access or remove potassium that is located extracellularly in the interstitial fluid between cells, which equilibrates with the blood serum. As dialysis functions to remove potassium ions from the blood serum as a result of a concentration gradient between the patient's blood serum and the dialysate, additional potassium ions are drawn out from cells into the intracellular fluids to provide for further removal of potassium ions.

Since potassium ion can readily diffuse across a dialysis membrane, the removal of potassium that occurs during a dialysis session is dependent upon the movement of potassium ions from the intracellular space to extracellular fluids. However, the movement of potassium ions from inside cells to the extracellular fluids is not consistent in all patients. In particular, acid-base balance can affect the influx and efflux of potassium ions from cells. Tonicity, glucose and insulin concentrations and catecholamine activity also affect the balance of potassium between cells and the extracellular fluid.

Figure 2:
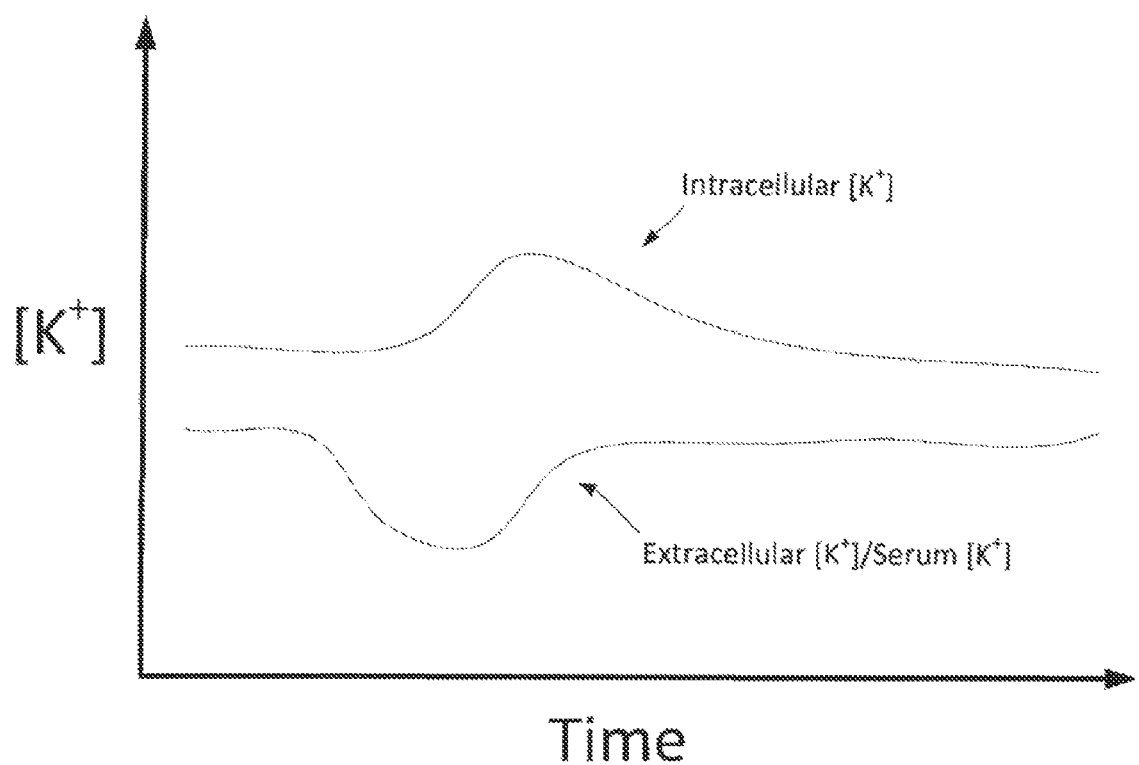
FIG. 2 shows a shift in intracellular and extracellular potassium ion concentrations at the beginning of a dialysis treatment.

Patients can experience slight alkalosis during the beginning of dialysis treatment, which can persist during a multi-hour dialysis treatment. Alkalosis is caused by bicarbonate present in the dialysate to act as a pH buffer. As shown in FIG. 2, a typical patient can experience a drop in serum potassium ion concentration at the beginning of dialysis due to a shift of potassium ions into the cells. Serum potassium ion concentration decreases readily at the beginning of dialysis during typical treatment regimens where the potassium ion concentration in the dialysate remains constant during treatment. After the conclusion of a dialysis treatment, potassium ions can efflux from the cells into the extracellular fluid. The changes that can occur in serum potassium concentrations during and after dialysis treatment can contribute to arrhythmias and other undesirable outcomes.

The rate of potassium removal is not uniform during dialysis wherein a constant concentration of sodium ion in the dialysate is maintained during treatment. Rather, the rate of potassium removal is dependent upon bicarbonate uptake of the patient, the particular time-point during treatment, and several other factors that make the removal of potassium ion unpredictable. As such, the amount of potassium ion removed during dialysis is often limited, which can affect the treatment of hyperkalemia by dialysis. As described herein, in some embodiments the concentration of potassium ion in the dialysate is modified during treatment to maintain one or more of: 1) a substantially constant concentration gradient during dialysis between the patient's blood and the dialysate, and 2) a substantially constant rate of mass transfer of potassium ions between the patient's blood and the dialysate during treatment. As such, the rate of potassium removal will become predictable based upon the length of dialysis regardless of carbonate uptake or other parameters that can affect the distribution of potassium ions between the extracellular space and intracellular cellular space.

In some embodiments, an electronic controller can calculate the amount of potassium ions removed from a patient during treatment. The concentration of potassium ions in the dialysate can be adjusted during treatment to slow or stop the removal of potassium ions during treatment if desired.

With reference to FIG. 1, fluid entering the dialysate loop 20 from the purification unit 30 or the water intake 64 is substantially free from dissolved ions and has a low conductivity. As such, the reconstitution of the dialysate by infusion set 35 can be readily controlled by the electronic controller. In some embodiments, the rate of addition of a potassium-containing salt can be controlled separately from other components of the dialysate such as sodium ions, calcium ions or bicarbonate buffer. As such, in one embodiment, a potassium salt, such as potassium chloride, can be present in concentrate infusion reservoir 36 and added to the dialysate circuit 20 through use of infusion pump 31, which is controlled by the electronic controller.

A property of the fluid entering dialysis circuit 20 can be measured by a sensor 74. The sensor 74 can be a conductivity sensor or a potassium-sensitive electrode. The structure of a potassium-sensitive membrane is not particularly limited; however, in some embodiments the potassium-sensitive electrode contains an ion-exchange polymer membrane impregnated with valinomycin or another macrocylic compound selective for transporting potassium ions. Sensor 76 further can be a conductivity or a potassium-sensitive electrode and can measure the dialysate after addition of a potassium salt. Suitable potassium-sensitive electrodes include model 9319BN (Thermo Scientific Inc.) and amperometric sensors described in A. S. Lima et al, "An Electrochemical Sensor Based on Nanostructure Hollandite-type Manganese Oxide for Detection of Potassium Ion," Sensors 9:6613-25 (2009), which is incorporated herein by reference. Where sensors 74 and 75 are conductivity sensors, the difference in conductivity measured between sensors 75 and 74 can be used by the electronic controller to calculate the potassium ion concentration added by infusion set 35 given the known molar conductivity of the potassium-containing salt and temperature of the dialysate. Similarly, where sensors 75 and 74 are potassium-sensitive electrodes, the change in concentration of potassium ion can be directly calculated by the electronic controller.

In some embodiments, the amount of potassium added by infusion set 35 is not determined and none of sensors 74, 75 and 76 are employed to determine a potassium ion concentration of the dialysate prior to contact with the dialyzer 15 or the patient in the case of peritoneal dialysis. Rather, a low conductivity of the fluid entering the dialysis loop 20 provides a determination that no significant amount of potassium ion concentration is entering the dialysis loop 20. As such, the concentration of potassium ions in the dialysate traveling to dialyzer 15 and/or the patient is determinable from known concentration of potassium salt in one or more of concentration reservoirs 36, 37 and 38 and the pumping rate of one or more of infusate pumps 74, 75 and 76.

In one embodiment, the amount of potassium ion added by the infusion set 35 is calculated by the electronic controller such that the concentration of potassium ion in the dialysate is known and the concentration of potassium ions in the spent dialysate after contact with the dialysis chamber 15 and/or the patient is measured by a return dialysate sensor 25. As such, the amount of potassium ions passing from the blood of a patient to the dialysate in the dialysis loop 20 can be calculated by the electronic controller.

In certain embodiments, the return dialysate sensor 25 is a potassium-sensitive electrode and the concentration of potassium ions in the spent dialysate can be directly calculated by a potential measured by the potassium-sensitive electrode. The difference between the known concentration of potassium ions in the dialysate prior to contact with the dialyzer 15 and/or the patient and the concentration in the spent dialysate measured by return dialysate sensor 25 allows for a direct calculation of mass transfer of potassium ions between the patient and the dialysate. As described, the mass transfer of potassium ions can be calculated based upon the measurement of the return dialysate sensor 25 wherein the potassium concentration of the dialysate used for dialysis is controlled by electronic controller providing for the infusion of a potassium salt infusate at a known rate.

In certain embodiments, the system can be used to perform ultrafiltration through the use of control pump 102. During the performance of ultrafiltration, the flow rate of dialysate traveling toward the dialysis chamber 15 and/or patient is slower than the amount of dialysate traveling past the return dialysate sensor 25. The difference in flow rates represents the rate of ultrafiltration or fluid removal from the patient. The electronic controller can account for the dilution of potassium ion concentration caused by bulk fluid transfer between the patient and the dialysis circuit 20. That is, the electronic controller can calculate mass transfer based upon the potential sensed by the return dialysate sensor 25 combined with the flow rate of the dialysate pre- and post-contact with the hemodialysis unit 15 and/or the patient. As such, the equivalents of potassium ion removed from the patient per unit of time can be readily calculated by the electronic controller. As described above, the controlled compliance properties of the dialysate circuit 20 allow for the control of dialysate flow rates in the dialysis circuit 20, and hence allow for the mass transfer of potassium ions to be calculated.

Figure 3:
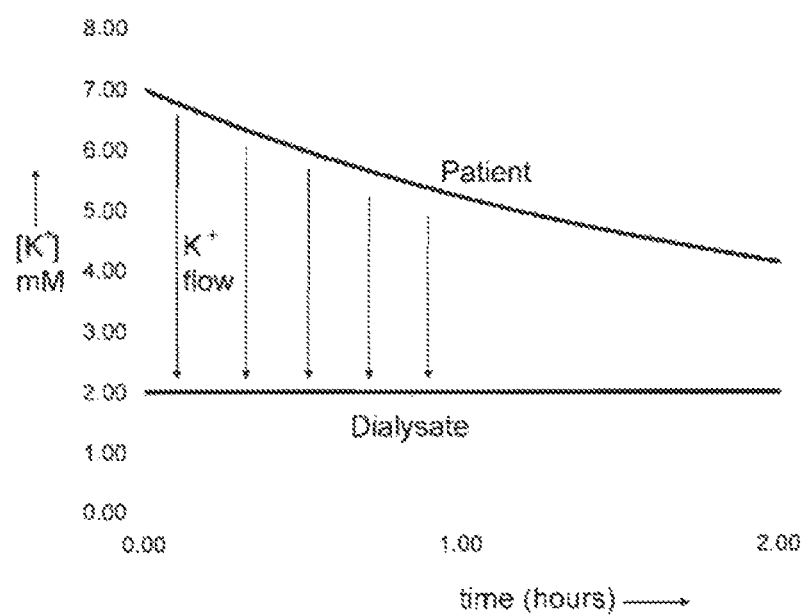
FIG. 3 shows an exemplary change in potassium ion concentration during an exemplary dialysis treatment with a constant dialysate concentration.

The electronic controller can adjust the potassium ion concentration of the dialysate to maintain a constant mass transfer of potassium over the course of treatment. As such, the rate of change in serum potassium ion concentration over time can be substantially equalized over the course of treatment. FIG. 3 shows an exemplary change in serum potassium concentration during dialysis (dashed line) with a dialysate having a constant concentration of potassium over time. As can be seen in FIG. 3, the gradient between the blood serum and the dialysate is largest at the beginning of dialysis that leads to a larger rate of potassium decline in the blood serum at the beginning of dialysis compared toward the end of a typical 4-hour dialysis session.

As shown in FIG. 3, a patient with a serum potassium concentration of 7 mM at the beginning of treatment has a serum potassium concentration that is decreased to about 4.2 mM at the end of the dialysis session. The rate of flow of potassium ions (mass transfer rate) is a function of the ion concentration gradient across the dialyzer membrane, which varies from 5 mM at the onset of the dialysis session to 2.2 mM at the end of the session. Consequently, there is a high rate of removal of potassium (high mass transfer rate) at the beginning of the session, while the rate of removal is about half of the initial value at the end of the two hour period illustrated in FIG. 3. The high rate of potassium removal at the beginning of treatment can cause complications for the patient, since rapid change in serum potassium levels can be compounded by an increase in the uptake of potassium ions by the cells as the serum bicarbonate levels increase. Toward the end of the dialysis session, there is a lower differential between the serum and the dialysate potassium concentrations resulting in a slow rate of potassium ion removal.

The amount of decline in blood serum potassium concentration is directly related to the mass transfer of potassium ions from the blood to the dialysate. As such, control of the mass transfer of potassium ions can be used to modify the rate of potassium concentration decline in the patient's blood. As such, the risk of arrhythmias due to rapid changes in serum potassium can be minimized. The systems described herein allow for the mass transfer of potassium to be calculated without knowing factors such as the actual potassium serum level of the patient, the diffusive permeability of the dialysis membrane or the intracellular/extracellular balance of potassium within the patient.

Figure 4:
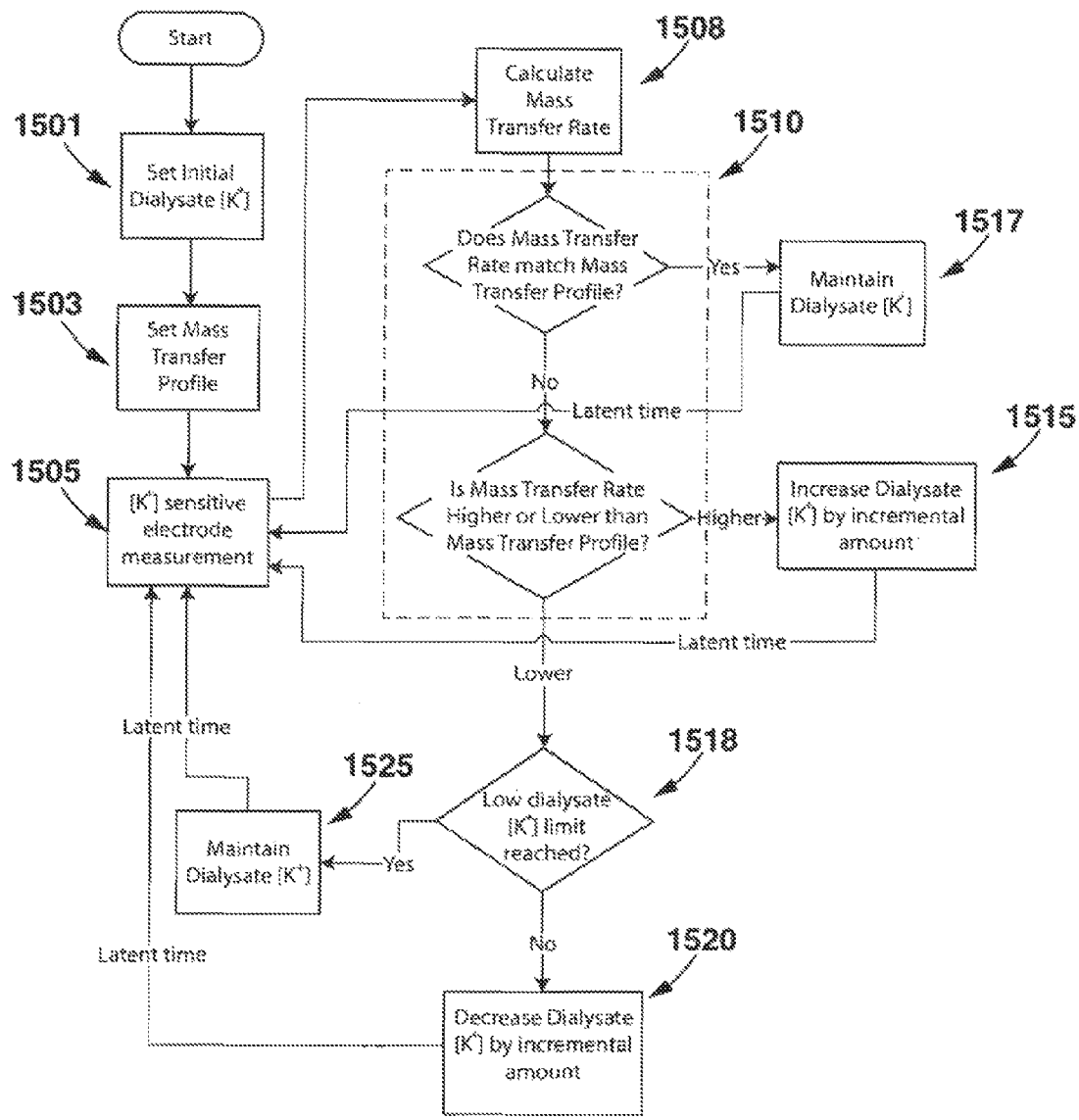
FIG. 4 shows an exemplary methodology for adjusting dialysate composition during treatment in accordance with some embodiments.

As shown in FIG. 4, an initial dialysate potassium concentration can be programmed in set 1501. The initial dialysate potassium concentration can be set based upon the expected potassium state of the patient. However, it should be noted that the initial dialysate potassium concentration can generally be higher than the level used for constant dialysate applications as exemplified in Table 1. In step 1503, a potassium mass transfer profile can be programmed into the electronic controller. In some embodiments, the mass transfer profile can be a constant rate of mass transfer throughout a period of dialysis treatment. In other embodiments, the mass transfer profile can vary the rate of mass transfer over a dialysis time period, or the dialysate potassium concentration can be set to not go below a preset limit. In some embodiments, the mass transfer profile can be set to zero where the dialysate potassium ion concentration can be set to match the blood serum concentration to effect zero net removal.

In step 1505, the potassium-sensitive electrode in the dialysate return sensor 25 measures an electrical signal dependent upon potassium concentration in the spent dialysate. In step 1508, the rate of mass transfer of potassium ions per unit time is calculated. In step 1510, the calculated rate of mass transfer of potassium ions is compared to the mass transfer profile, as shown within the dashed box shown in FIG. 4. If the mass transfer rate matches the mass transfer profile in step 1510, then the dialysate potassium concentration is maintained in step 1517 and after a latency time the composition of the spent dialysate is continually monitored in step 1505. If the mass transfer rate in step 1510 is higher than the mass transfer profile, then in step 1515 the potassium concentration of the dialysate is increased by increasing the rate of potassium salt addition by the infusion set 35 by an incremental amount to reduce the concentration gradient of potassium ions between the patient and the dialysate. If the mass transfer rate in step 1510 is lower than the mass transfer profile, then in step 1518 the current potassium concentration of the dialysate is compared against a lower limit. The concentration of the patient's blood serum cannot decrease to be less than the potassium ion concentration of the dialysate. As such, step 1518 can be used as a check to ensure that the blood serum is not brought to a potassium concentration below a preset limit. If the limit has been reached in step 1518, then the potassium concentration of the dialysate is maintained in step 1525. If the limit has not been reached in step 1518, then the rate of potassium salt infusion by infusion set 35 is decreased by an incremental amount to increase the potassium concentration gradient between the patient and the dialysate.

After the dialysate potassium concentration is appropriately maintained or adjusted, a latency time is elapsed prior to continuing to monitor the potassium concentration in the spent dialysate in step 1505. Due to the rapid circulation of the dialysate through the dialysis circuit 20, the latency period can be short. As such, the rate of potassium salt addition to the dialysate can be quickly adjusted to match the mass transfer profile programmed in step 1503. In some embodiments, the latency period is from about 15 seconds to about 3 minutes. In other embodiments, the latency period is form about 30 seconds to about 5 minutes.

Figure 5:
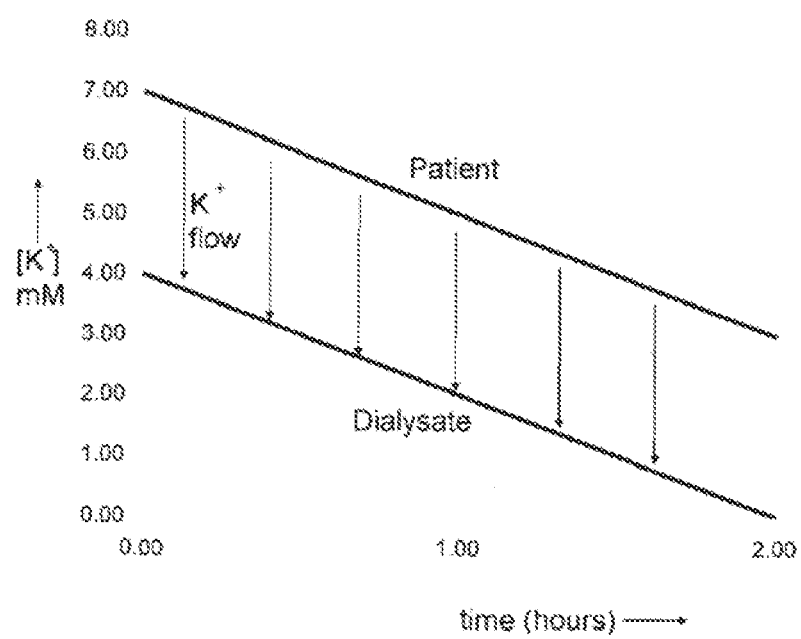
FIG. 5 shows an exemplary change in potassium ion concentration during a dialysis treatment with an adjustable dialysate concentration.

FIG. 5 shows a hypothetical dialysis treatment wherein the potassium ion concentration of the dialysate is varied in the manner outlined in FIG. 4. FIG. 5 shows a mass transfer profile that is constant throughout the treatment. The potassium ion concentration gradient between the plasma and the dialysate ($\Delta C$) is proportional to the rate of mass transfer of potassium ions. The process of FIG. 5 allows for the dialysate potassium concentration to be iteratively adjusted to maintain a $\Delta C$ that provides the desired rate of mass transfer. However, it should be noted that the proportionality between $\Delta C$ and the rate of mass transfer is not necessarily constant over all concentration ranges.

As shown in FIG. 5, a constant gradient, for example, of about 3 mM can be maintained between the potassium levels in the serum and in the dialysate. At the beginning of the dialysis treatment, the dialysate potassium level can be high, for example, 4 mM. At the end of the two-hour period illustrated, the dialysate concentration of potassium can be brought to zero while the serum level for potassium ions is decreased to about 3 mM. As such, the following benefits can be obtained: (a) by prevention of the rapid decrease of potassium ion concentration, cellular uptake of potassium can be reduced; (b) as a consequence of (a) more potassium can be removed during a treatment session; and (c) the amount of potassium infusate used during treatment can be reduced as a consequence of low potassium ion dialysate levels at the end of treatment.

In another embodiment, the dialysate composition return sensor 25 can be removed from the system and an optional blood composition sensor 26 can be present in the blood circuit 10 as shown in FIG. 1. The blood composition sensor 26 preferably measures the potassium ion concentration in the blood prior to dialysis in dialyzer 15. The blood composition sensor 26 can have the same structure and components as the dialysate return composition sensor 25. In some embodiments, the dialysate return sensor 25 and the blood composition sensor 26 can both be present.

As described above, the use of the dialysate return composition sensor 25 can be used to accurately control potassium mass transfer. The amount of mass transfer observed and the current potassium ion concentration of the dialysate can be used by the electronic controller to estimate the potassium ion concentration in the blood. However, the blood potassium ion composition can be directly measured by the blood composition sensor 26 wherein the dialysate potassium concentration is iteratively modified to adjust the rate of the decrease in blood potassium concentration over time. That is, the rate of potassium salt infusion into the dialysate can be adjusted based upon the measurement made by the blood composition sensor 26 in an iterative fashion, as described above, to reach a desired rate of serum potassium ion concentration change.

The present invention in one or more embodiments provides a multimodal dialysis apparatus for non-invasively monitoring serum potassium concentration in a subject undergoing a dialysis treatment. The multimodal dialysis apparatus may include an extracorporeal flow path, such as the blood loop or circuit 10 referenced in FIG. 1, for transporting blood of a subject to a hemodialysis unit, such as the dialyzer 15 referenced in FIG. 1; at least one of an electromyogram sensor and an electrocardiogram sensor receiving at least one electrical signal and for detecting a change in muscle activity of a subject based on the received electrical signal and for producing at least one output electrical signal based on the change in muscle activity as detected, the electrical signal being indicative of a serum potassium concentration in the blood being transported from the extracorporeal flow path to the hemodialysis unit; a dialysate flow path, such as dialysate loop 20 referenced in FIG. 1, for transporting a dialysate fluid to the hemodialysis unit; and an infusate pump, such as the infusate pump 74, 75 or 76 referenced in FIG. 1, in potassium communication with the dialysate flow path such that the infusate pump is controlled to adjust a potassium concentration in the dialysate flow path based at least in part on the serum potassium concentration obtained via the at least one of the electromyogram sensor and the electrocardiogram sensor.

The one or more of these ECG features can be significant non-invasive markers or indicators for monitoring corresponding serum potassium concentration. Without wanting to be limited to any particular theory, it is believed, and at least with the T-wave measurements, the T-wave measurement can be specific in determining the details of repolarization once it begins, which is potassium sensitive. For instance also, the R-wave is believed to be sensitive to the difference between intracellular and extracellular potassium. In this connection, and at least in certain particular instances, the T-wave amplitude, the R-wave amplitude, and/or the T/R amplitude ratio may be more sensitive than other ECG features such as the P-R interval and the QT interval as markers or indicators for monitoring serum potassium concentration. This may be because the P-R interval and the QT interval reflect more on the effects of autonomic nervous system rather than on potassium concentration variations.

The at least one electromyogram sensor and/or the at least one electrocardiogram sensor may be positioned within the medical device in any suitable way or at any suitable position. In certain instances, the at least one electromyogram sensor and/or the at least one electrocardiogram sensor may be positioned on or within the subject at any suitable locations. In certain instances, the at least one electromyogram sensor and/or the at least one electrocardiogram sensor may be located external to or internally underneath the skin around the chest of the subject.

The at least one electromyogram sensor and/or the at least one electrocardiogram sensor also be contained within a medical device to provide greater ease in handling. For instance, and as illustratively depicted in FIG. 47, a medical device generally shown at 4714 may include the at least one electromyogram sensor (not shown).

Referring back to FIG. 47, and in accordance with certain instances, the medical device 5714 may be employed in connection with a pulse generator 4711 for producing one or more pulse sets; one or more detectors or pulse-sensitive electrodes 4712 for mediating communication between the pulse generator 4711 and a subject 4720, wherein the medical device 4714 helps generate and/or receive a signal indicating an extent of muscle strain of the subject 4720 upon a contact with the one or more pulse sets. Optionally, a processor 4716 may be included for receiving the signal from the medical device 4714 and producing an output on serum potassium concentration based on the signal. For illustration purposes, the components referenced in FIG. 47 may collectively be grouped as a medical system generally shown at 4710.

In certain instances, the at least one electromyogram sensor of the medical device 4714 may be a pressure sensor or a blood pressure cuff.

Referring back to FIG. 47, the pulse generator 4711 may be an electronic circuit producing a digital signal having only two levels corresponding to 0 and 1 levels, or OFF and ON. Duration of each interval and number of times to repeat them are predetermined by an algorithm and can be changed if necessary. Such a pattern can be generated using a logic gates, timer circuits or programmable devices such as a computer or a microprocessor. A non-limiting example of the pulse generator 4711 may be an Arduino microprocessor.

The pulse generator may be provided with a pulsing schedule such that the one or more pulse sets include a first pulse set and a second pulse set, the first and second pulse sets are produced according to one or more of the following algorithm rules: i) the first and second pulse sets are separated in time by 0.5 to 5 seconds; ii) the first and second pulse sets each independently include 3 to 10 pulses; and iii) the first and second pulse sets each independently having a frequency of 2 to 50.

The present invention in one or more embodiments is unique in using burst stimulation to generate and monitor the ripples on the muscle response and the subsequent interpretation of these ripples to derive the relation to the serum potassium concentration are unique properties of the algorithm. In doing so, the number of pulses and the frequency of the pulses may need to be chosen carefully. For example, if there are too few pulses, then the measured muscle response is the transient one, not the steady state one. If there are too many pulses, one may risk that the muscle will fatigue, giving an erroneous response. Similarly, the frequency of the stimulation must be low enough to prevent immediate formation of tetnus which eliminates the ripples on the contraction. At the same time, stimulus that is delivered at too low frequencies do not result in the fusion of the contraction, hence would not allow the analysis of the ripples. Even though the present algorithm suggests the use of N=5 pulses delivered at f=5 Hz, deviations from those numbers are within the scope of the present invention.

The operation of the pulse generator may be triggered by on its own using a self-timer, by the monitor, or by the medical care provider. It may also be triggered when there is blood draw for analysis, which can be used for the calibration of the sensory.

The pulsing schedule of the pulse generator may be provided such that the first and second pulse sets are produced according to two or more of the following pulsing rules: i) the first and second pulse sets are separated in time by 1.5 to 2.5 seconds; ii) the first and second pulse sets each independently include 4 to 6 pulses; and iii) the first and second pulse sets each independently having a frequency of 2 to 10 Hz.

The first and second pulse sets are only illustrative of the pulsing schedule in that the pulsing schedule may include more than two pulse sets. In particular, the pulsing schedule may include three, four, five or more pulse sets with each of them independently including feature(s) described in relation to the first or second pulse set.

Regarding the pulsing rule i), the first and second pulse sets may be separated in time by 0.5 to 5 seconds, 0.75 to 4.25 seconds, 1.0 to 3.5 second, or 1.5 to 2.75 seconds. The separation in time between the first and second pulse sets may be measured by the distance in time between the first peak of the first pulse set and the first peak of the second pulse set. The separation in time between two adjacent pulse sets may be adjusted accordingly based on the specifics of a project at hand. However, these separation in time values may be particularly useful for carrying out the serum potassium concentration monitoring intended by the present invention in one or more embodiments Regarding the pulsing rule ii), the first and second pulse sets may each independently include 3 to 10 pulses, with each pulse observable with the presence of a peak, or 3 to 8 pulses, or 4 to 6 pulses. The total number of pulses or peaks contained within each of the pulse sets may be adjusted accordingly based on the specifics of a project at hand. However, these pulse numbers may be particularly useful for carrying out the serum potassium concentration monitoring intended by the present invention in one or more embodiments.

Regarding the pulsing rule iii), the first and second pulse sets may each independently be of a frequency of 2 to 50 Hz, 2 to 40 Hz, 2 to 30 Hz, 2 to 20 Hz, or 2 to 10 Hz. The pulsing frequency may be adjusted accordingly based on the specifics of a project at hand. However, these frequency ranges may be particularly useful for carrying out the serum potassium concentration monitoring intended by the present invention in one or more embodiments.

Referring back to FIG. 47, optionally an amplifier 4718 may be used to mediate communication between the pulse generator 4711 and the one or more pulse-sensing electrodes 4712.

In certain instances, the amplifier 4718 may be capable of amplifying and delivering the pulses to tissues with unknown load impedance. It is possible that the load impedance of the tissue can be as low as 20 Ohms, and as high as 50 kilo-ohms. Similarly, the output voltage of the amplifier is adjustable from 1 Volt to 10 Volts, preferably at 8 Volts. In order to minimize the patient discomfort, the pulsing schedule may need to be kept at least initially at a relatively low value in voltage, such as 2 Volts. If there is no response from the tissue, then the output voltage is increased until an evoked response is observed. Furthermore, the amplifier may also need to have a broad frequency response, from 0.1 Hz to 1 kHz to minimize the distortion of the delivered pulses. In addition, and in certain instances, the amplifier may need to provide the required electrical isolation necessary for all patient connected electrical medical devices to reduce the risk accidental electrocution of the subject.

Figure 48:
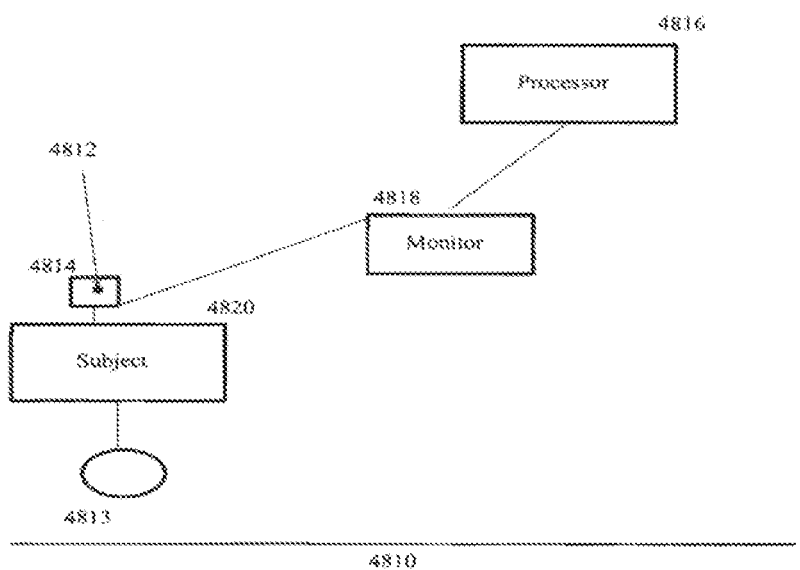

In certain embodiments, and as depicted in FIG. 48, a medical device 4814 may include one or more electrocardiogram (ECG) electrodes 4812 for receiving one or more electrocardiogram features from the subject 4820, the one or more electrocardiogram features including T-wave amplitude, R-wave amplitude, T-slope, ratio of T-wave amplitude to R-wave amplitude (T/R ratio), and T-wave flatness; and an ECG algorithm for producing an output on the serum potassium concentration in the subject 4820, based on an input including the one or more electrocardiogram features, wherein the ECG algorithm includes one or more of the following operational rules: i) the output on the serum potassium concentration being a function of the R-wave amplitude; ii) the output on the serum potassium concentration being a function of the T-wave amplitude; iii) the output on the serum potassium concentration being a function of the T/R ratio; and iv) the output on the serum potassium concentration being a function of the T-wave flatness.

Myocardial cellular action potentials are formed by the flow of positively charged ions such as sodium, potassium, and calcium through the cellular membranes. The ECG is made up of the aggregation of electrical signals from many myocardial cells. Lead II is the voltage between the left leg (LL) electrode and the right arm (RA) electrode. Leads V1 through V6 are termed the "precordial" leads, and the negative electrode thereto is the average of the three limb leads (I, II, and III). Leads I and III are the voltage between the left arm and right arm electrode and between the left leg and left arm electrode, respectively. The ECG features may be detected according to the schedules tabulated in Table 7.

TABLE 7

Schedules for Detecting ECG Features

| Feature | ECG Feature Identification Schedule |
| --- | --- |
| R-wave identification | Find maximum amplitude (either positive or negative) of segment in R-wave template. Store the polarity of this segment. Find threshold points in the data stream that exceed 70% of the template maximum amplitude. Look at the data segment from the first threshold point encountered looking out for the width of the R-wave template. If the detection is not too wide or flat, it is considered a valid R-wave. This is done by checking if the slopes at half of the template width on either side of the candidate R-wave peak are at least 60% of the corresponding slopes on the template signal. Skip ahead (blank) for 1.5 * template width before searching for the next R wave. Store the intervals between R waves also (RR intervals). |
| P-wave start | Starting 20 ms before the Q time, store all the samples for the previus 0.25 * RR interval. Sort the samples in ascending order. Store the times of the largest 10% of samples, and then start at the initial time of this P-wave segment. Looking back for 30 ms, find the maximum slope over a 20 ms interval. Then find the earliest point where the upslope of the p-wave exceeds ½ of the maximum slope. |

TABLE 7-continued

Schedules for Detecting ECG Features

| Feature | ECG Feature Identification Schedule |
| --- | --- |
| P-wave peak | Find the width of the p-wave segment with the largest 10% of samples, as described above.<br>Set the P-peak time to the middle of this segment. |
| R-wave start (Q time) | Look back from the peak of the R wave for 100 ms.<br>The Q point is detected when the slope decreases to the point that the difference in signal amplitude over 18 ms is less than 1/50 of the R-wave amplitude for several samples. |
| R-wave peak | Point of maximum amplitude away from 0, either in positive or negative direction, within template width after the R-wave detection point. |
| R-wave end | Find minimum amplitude within 46 ms after R wave peak.<br>Find maximum slope and minimum nonnegative slope within 50 ms after the minimum amplitude. Look out beyond the minimum amplitude point for the point where the slope is 1/10 of the way from the minimum to the maximum slope. |
| T-wave start | End of R-wave |
| T-wave peak | Find maximum positive amplitude during the interval starting 150 ms after the R-wave peak through the point $0.4 * \sqrt{RR\ interval}$ after that.<br>Look through that same window, store all the samples, and sort them in ascending order.<br>Find the times of all the samples in the top 10%. Pick the center of all those times. |
| T-wave end | Find the minimum amplitude between 130 and 180 ms after the T-wave peak. Use this as the isoelectric line.<br>Find the steepest slope over a 15 ms segment between the T-wave peak and 0.2 * RR interval after it.<br>Interpolate the maximum slope from the point where it is measured to the isoelectric line.<br>Store that point as the end of the T-wave. |

The one or more electrocardiogram electrodes may include one or more of lead II, lead V2, lead V3 and lead V4. -The rationale for selecting these leads may be that the ECG change which is usually first observable given abnormal potassium levels is the appearance of peaked, symmetric T-waves. T-waves are largest on the precordial leads, and T-wave changes due to hyperkalemia are most likely seen on V2, V3 and V4.

In certain instances, the one or more electrocardiogram electrodes consist of lead II only. Lead II is examined because it is closest to the Reveal signal which is optionally useful for certain chronic kidney disease monitoring projects.

Figure 47:
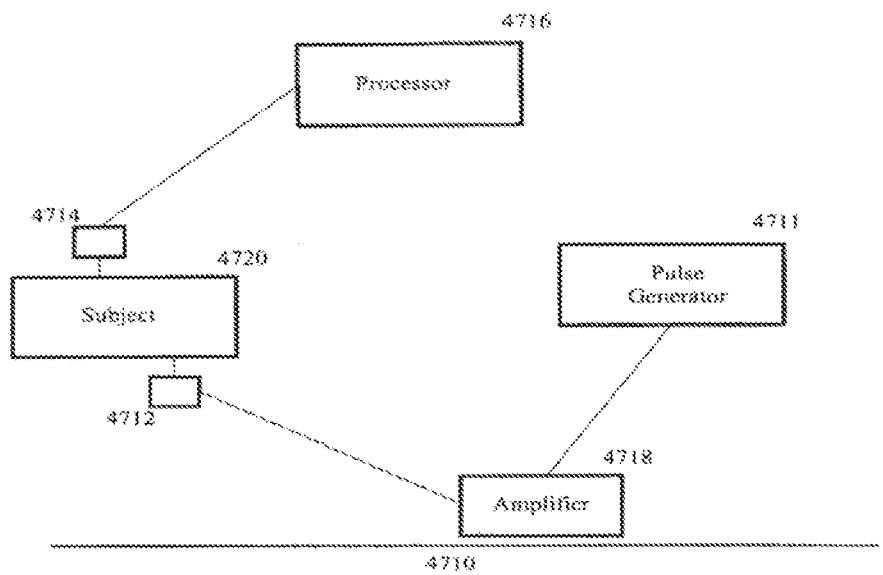
FIGS. 47-48 each show a medical system in accordance with some embodiments.

The output on the serum potassium concentration, as directly or indirectly obtainable from the medical device referenced in FIG. 47 and/or the medical device referenced in FIG. 48 may be a difference between a serum potassium concentration at time $t_1$ of the subject and a baseline potassium concentration at time $t_0$ of the subject, time $t_1$ being at least 10 minutes, 20 minutes, 30 minutes, 40 minutes, 50 minutes, 60 minutes, 120 minutes, 12 hours, 24 hours, 48 hours, or 96 hours apart from $t_0$. The time period between time $t_0$ and time $t_1$ may be a time interval within a medical treatment session such as a dialysis session, during which time $t_0$ represents an earlier time point during the dialysis and time $t_1$ represents a later time point during the dialysis. This is useful as the subject can be monitored in real time for serum potassium concentration via the use of the at least one electromyogram sensor and/or the at least one electrocardiogram sensor contained within or connected to the medical device such that the subject may be spared of the inconvenience and sometimes pain associated with periodic blood draws otherwise needed for conventional potassium concentration monitoring.

The baseline serum potassium concentration may be a value selected from the group consisting of a baseline serum potassium concentration of the subject obtained at a periodic blood draw, a baseline serum potassium concentration of the subject obtained at the onset of a dialysis session, and a baseline serum potassium concentration of the subject at the end of a dialysis session. In this connection, the baseline potassium concentration values can be determined at the time of the weekly, biweekly, monthly, or bi-monthly blood draw when the potassium level can be determined accurately. Baseline can also be defined at the onset of the dialysis session, because that is the onset of the measurement process. It is also possible to define the baseline as the measurements done at the end of the dialysis session, because at that time, the potassium value is likely to be within the normal physiological range, and very close to the dialysate value, which is known.

In certain instances, one or more baselines for each ECG feature may be determined on an individual basis for each subject, for instance, one when [K+]=5 mM and one when [K+]=3.5 mM. If this is not possible, then baseline may be measured at some time when potassium is within these ranges. It should be noted that the response is fairly linear in the clinically significant range of hyperkalemia, i.e. [K+]=5 mM to [K+]=9 mM.

According to the operational rule of the ECG algorithm, the output on the serum potassium concentration may be in a negative correlation with the R-wave amplitude. The negative correlation refers to an observation where the R-wave amplitude increases as the serum potassium concentration decreases in the subject. The negative correlation, however, does not require a straight line correlation with a single slope. Rather, the negative correlation is found when the beginning values of the serum potassium concentration and the R-wave amplitude relative to their corresponding ending values change in the same direction.

According to the operational rule of the ECG algorithm, the output on the serum potassium concentration is in a positive correlation with the T-wave amplitude. The positive correlation refers to an observation where the T-wave amplitude decreases as the serum potassium concentration decreases in the subject. The positive correlation, however, does not require a straight line correlation with a single slope. Rather, the positive correlation is found when the beginning values of the serum potassium concentration and the T-wave amplitude relative to their corresponding ending values change in the same direction.

According to the operational rule of the ECG algorithm, the output on the serum potassium concentration is in a positive correlation with the T-slope. The positive correlation refers to an observation where the T-slope decreases as the serum potassium concentration decreases in the subject. The positive correlation, however, does not require a straight line correlation with a single slope. Rather, the positive correlation is found when the beginning values of the serum potassium concentration and the T-slope relative to their corresponding ending values change in the same direction.

In certain instances, the ECG algorithm of the medical system 12.100 does not include the operational rule i) and includes only one or more of the operational rules ii), iii) and iv). This may be useful as the T-wave amplitude may be subject to certain fluctuation dependent upon the type of the ECG lead or leads used and the individuality of the subject.

The ECG electrodes 4812 of the medical system 4810 may include a first set of electrodes consisting of lead II, lead V2, lead V3 and lead V4, and a second set of electrodes consisting of lead II only, wherein the ECG algorithm further includes a calibration rule which is the medical system is operationally calibrated if one or more of the following is met: v) a difference between the outputs according to rule ii) from the first set of electrodes and the second set of electrodes is no greater than 20%; vi) a difference between the outputs according to rule iii) from the first set of electrodes and the second set of electrodes is no greater than 20%; and vii) a difference between the outputs according to rule iv) from the first set of electrodes and the second set of electrodes is no greater than 20%.

The ECG electrodes 4812 of the medical system 4810 may include a first set of electrodes consisting of lead II, lead V2, lead V3 and lead V4, and a second set of electrodes consisting of lead II only, wherein the ECG algorithm further includes a calibration rule which is the medical system is operationally calibrated if one or more of the following is met: v) a difference between the outputs according to rule ii) from the first set of electrodes and the second set of electrodes is no greater than 10%; vi) a difference between the outputs according to rule iii) from the first set of electrodes and the second set of electrodes is no greater than 10%; and vii) a difference between the outputs according to rule iv) from the first set of electrodes and the second set of electrodes is no greater than 10%.

Referring back to FIG. 48, a dialysis device 4813 such as the dialyzer 15 referenced in FIG. 1 is positioned to show that the subject 4820 is monitored for serum potassium concentration while under a dialysis treatment. This design provides a real-time feedback control of the dialysis operation based upon the output on the serum potassium concentration. If the serum potassium levels are out of normal ranges, this may be detectable via changes in the ECG. Subjects with end-stage renal disease who are on dialysis have large fluctuations in systemic potassium levels between dialysis sessions. They may be hypokalemic at the end of a dialysis session, and as their potassium levels rise between dialysis sessions, they may become hyperkalemic before the next session. Hemodialysis subjects have a high rate of sudden death. Their potassium fluctuations could lead to cardiac arrhythmias. Both hyper- and hypokalemia are well-known risk factors for sudden cardiac death.

Figure 49:
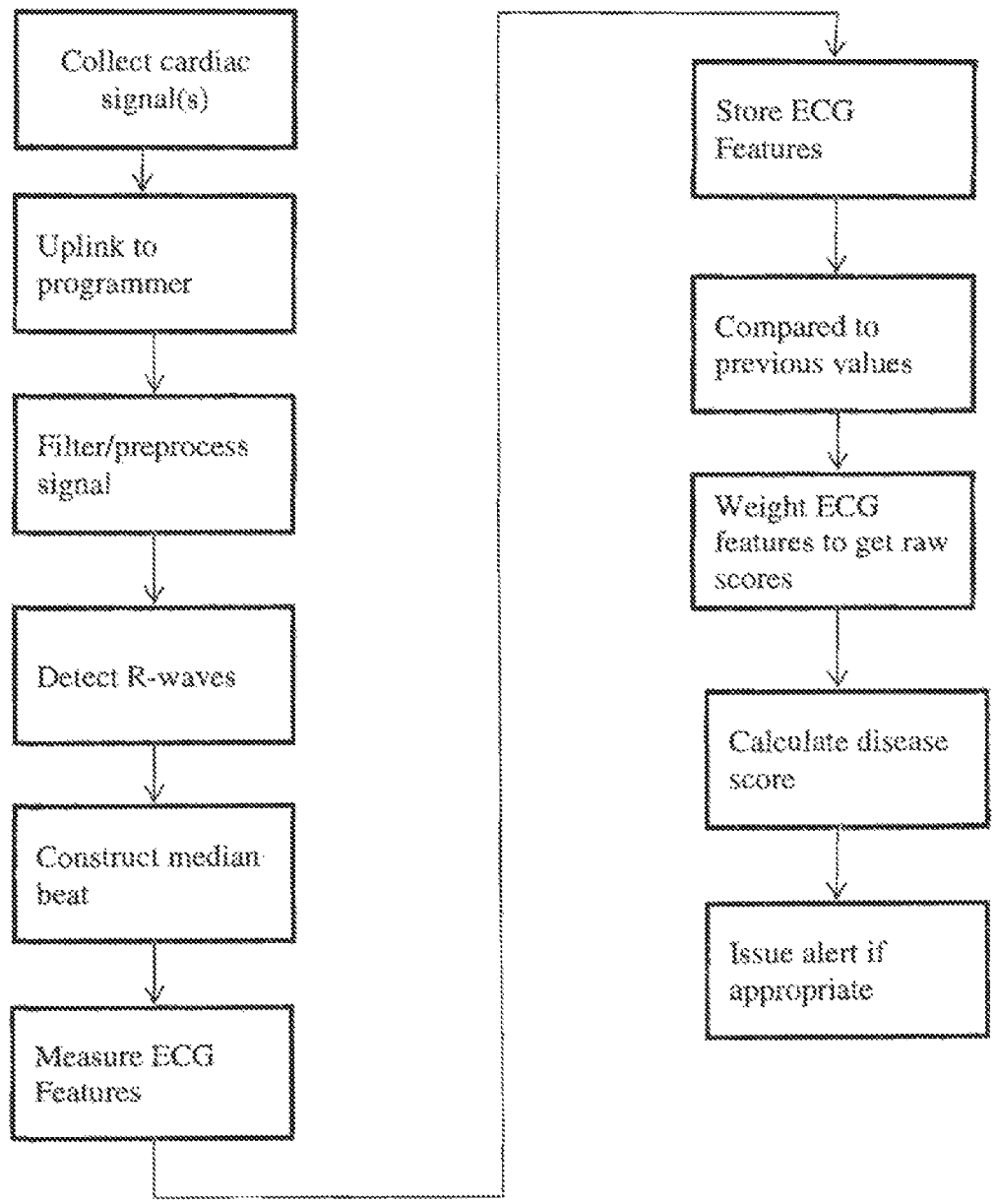
FIG. 49 depicts an exemplified flow chart for the ECG assisted potassium concentration monitoring.

A non-limiting example of a method of monitoring the ECG features and estimating the potassium concentration is provided as follows. A signal from an implanted device is recorded periodically and stored in the device. At specified times, either at the same time each day, or before and after dialysis, stored segments of the signals are uplinked to a programmer device. The segment of data is preprocessed by being high- and low-pass filtered and possibly inverted. The least noisy sections of data may be identified to be used for measurement. An R-wave is detected as the largest amplitude peak within the first few seconds of a data segment. After a blanking period, additional R-waves are identified which are of comparable polarity, magnitude, and QRS width. The R-waves from a segment of data, nominally 1 minute, may be used to construct a median beat representing the signal. The R-waves in the measurement window following the selected template time are detected by the amplitude peaks. They are subsequently sorted by R-R interval, and the longest $\frac{1}{12}$th and shortest $\frac{1}{12}$th of intervals are thrown out. The remaining complexes are time-scaled to the average R-R, and then the median value for each sample in the R-R interval is selected to form the median beat. ECG features are measured either on every beat, as identified by an R-wave, or just on the median beat. ECG features including some of the following are identified: T-wave amplitude, R-wave amplitude, T-wave amplitude/R-wave amplitude ratio, T-slope, T-slope over amplitude, T-wave peak-to-peak amplitude, R-R interval, QRS duration, and T-wave phase type. T-wave phase type is a measure of whether the T-wave is monophasic or biphasic. The maximum positive signal amplitude and maximum negative signal amplitude within a window following the R-wave are identified. They are compared to the baseline amplitude following the T-wave. If either the maximum positive signal amplitude or maximum negative signal amplitude is much farther from baseline than the other, it is a monophasic T-wave. If they are approximately equally far from baseline, it is a biphasic T-wave. The T-wave phase type may change from monophasic to biphasic as potassium levels increase. The programmer device calculates the ECG feature measurements from the signal which has been uplinked and compares to previous measurements in the subject to determine if changes are occurring, or if deviations from normal are occurring. The programmer device combines the ECG feature measurements in a weighted manner to estimate potassium concentration. FIG. 49 depicts an exemplified flow chart for the ECG assisted potassium concentration monitoring.

Referring back to FIG. 48, a monitor 4818 may be included to receive and analyze the ECG signals transmitted from the ECG electrodes 4812. The monitor 4818 may be spaced apart from the ECG electrodes 4812 and may also be co-localized with the ECG electrodes 4812 to form an integral single device. Non-limiting examples of the monitor 4818 with or without being coupled with the ECG electrodes include Electrogram from implanted Reveal device, surface electrocardiogram from external electrodes, signal from electrodes of subcutaneous implantable cardioverter-defibrillator, and ventricular far-field electrogram from implantable cardioverter-defibrillator or cardiac resynchronization defibrillator. The monitor 4818 may further communicate with the processor 4816 for downstream data communication, optionally via wired or wireless connection. In certain instances, the processor 4816 can be functionally equivalent to the work station 1458 referenced in FIG. 14.

Operation of the Dialysate Purification Module

Figure 6:
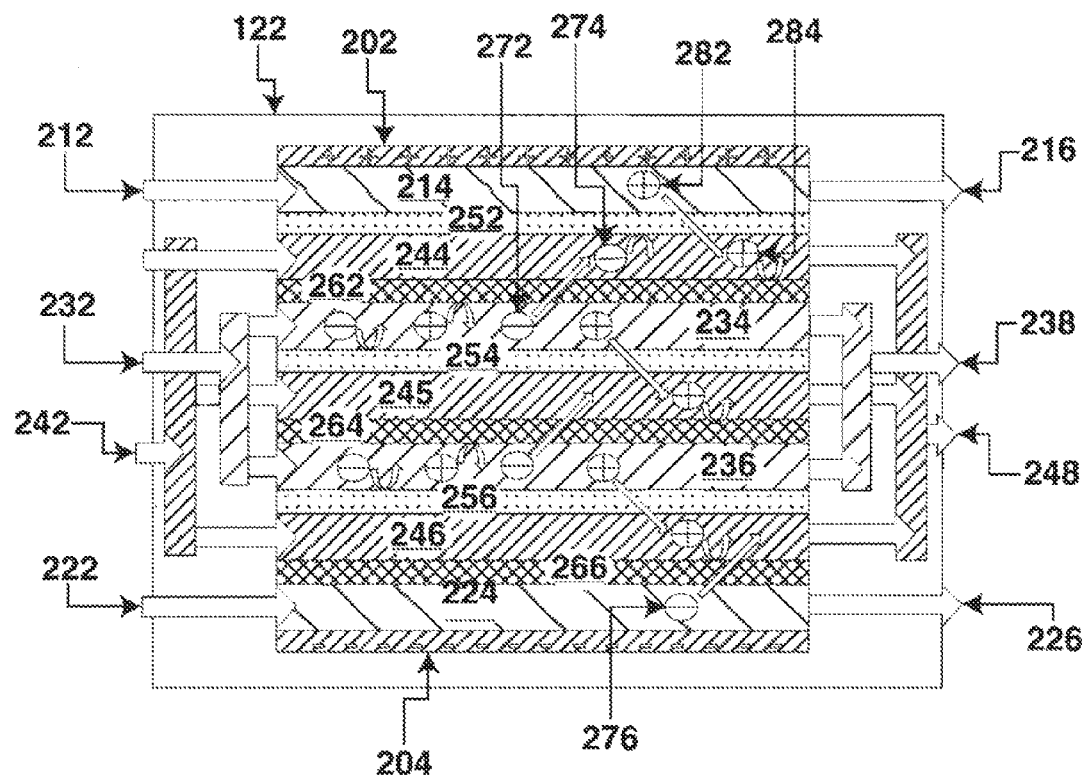
FIG. 6 shows a schematic for an embodiment of an electrodialysis unit.

The purification module 30 purifies the incoming dialysate and readies it to be reconstituted using the concentrate infusion set 35 to form regenerated dialysate, as described above. An exemplary operation of the electrodialysis unit 122 is shown in FIG. 6. Electrodialysis unit 122 is constructed as a multi-chamber flow device where the fluid flow through all chambers is substantially perpendicular to the applied electrical field. An electrical field can be applied using a pair of electrodes, an anode 202 and a cathode 204. Therefore, in FIG. 6, the produced electrical field is oriented in a direction from anode 202 to cathode 204. As a result of the presence of the electrical field, positively charged particles, such as 282 and 284 experience a force toward the cathode 204. Similarly, negatively charged particles, such as 272, 274 and 276 experience a force toward the anode 202.

The function of the electrodialysis unit 122 is to selectively move the charged species, i.e. ions, from one set of chambers to another, thereby reducing the concentration of the ions in a fluid that can be reconstituted and used again as a dialysate. That is, an electrodialysis unit has at least two chambers. A diluate chamber becomes depleted in anions and cations due to operation of the electrodialysis unit 122. The fluid passing through the diluate chamber can then be reconstituted as a dialysate. The remaining chamber is a concentrate chamber that becomes enriched in cations and anions through operation of the electrodialysis unit 122. In certain embodiments, at least two concentrate chambers are present, where one concentrate chamber becomes enriched in cations and the other concentrate chamber becomes enriched in anions.

FIG. 6 presents one embodiment of an electrodialysis unit 122. Movement of the ions in the electrodialysis unit 122 occurs in three set of compartments. The two compartments that are in contact with the anode 202 and cathode 204 are the compartments 214 and 224, respectively. Compartments 214 and 224 are concentrate compartments having a concentrate solution provided therein as described above. However, the solution flowing through compartments 214 and 224 can also be referred to as electrode rinse solutions that enter these two compartments through the ports 212 and 222, respectively. The electrode rinse solutions exit through ports 216 and 226. For charge balance, the electrode rinse solutions can be mixed with each other, or with the solutions in the other chambers.

The dialysate to be regenerated flows into the electrodialysis unit 122 via the intake port 232 and flows into the diluate chambers 234 and 236. Ultimately, the ion concentration in the diluate chambers 234 and 236 is reduced and the ion depleted solution or diluate exits the electrodialysis unit via the port 238. This diluate leaving the electrodialysis via port 238 is used for the regeneration of the dialysate. Ions leaving the diluate are accumulated in the concentrate chambers 244, 245 and 246. The concentrate fluid is circulated using an external pump 112, where the concentrate solution is removed from the electrodialysis unit 122 via the exit port 248 and reintroduced back into the electrodialysis unit via the port 242. That is, at least part of the concentrate solution re-circulates through the electrodialysis unit 122. Although FIG. 6 shows two diluate chambers 234 and 236 and three concentrate chambers 244, 245 and 246, the number of chambers for each can vary from 1 to 100, but not necessarily in equal numbers. Further, the electrode chambers 214 and 224 can serve as concentrate chambers. An increased number of chambers increases the surface area, and therefore the efficiency of the electrodialysis unit 122.

FIG. 6 also shows that the electrode rinse solutions, the diluate solution and the concentrate solution are separated by ion selective membranes. Specifically, the cation-selective membranes 252, 254 and 256 allow the passage of only the positively charged cations. Similarly, the anion-selective membranes 262, 264 and 266 allow the passage of only the negatively charged anions. As shown in FIG. 6, cations, such as 282, move toward the cathode 204 until they encounter an anion-selective membrane such as 262. Similarly, the anions, such as 276, move toward the anode until they encounter a cation membrane such as 256. Ultimately, about 90% of the ionic species are moved from a diluate chamber into a concentrate chamber.

Figure 7:
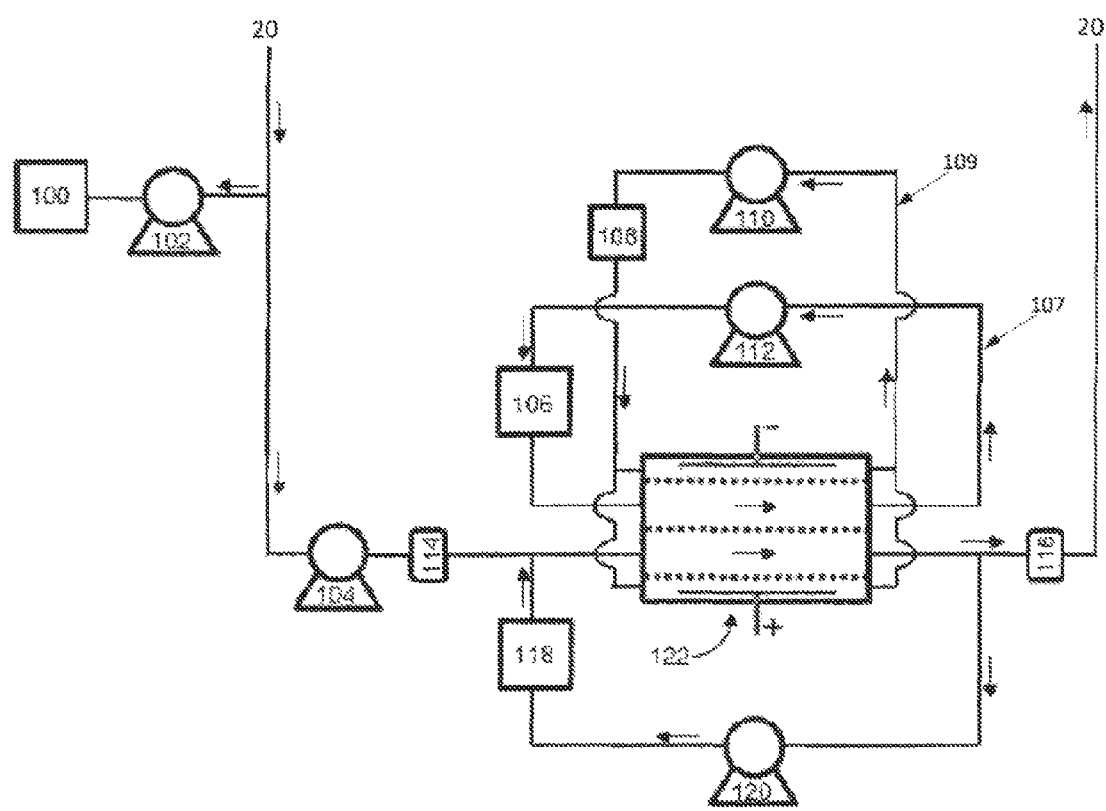
FIG. 7 shows a schematic for an embodiment of a purification module in accordance with some embodiments.

FIG. 7 shows an embodiment of a purification unit 30 for regenerating dialysate. In the embodiment shown in FIG. 7, three separate reservoirs 108, 106 and 118 are used along with pumps 110, 112 and 120 to circulate an electrode rinse solution, a concentrate solution and a diluate solution, respectively. Again, the diluate solution is the solution used for the regeneration of the dialysate. In some embodiments, the diluate solution is re-circulated via the pump 120 to increase the flow rate of the diluate over and beyond the flow rate of the dialysate within the dialysate loop 20, which is circulated via the pump 104 through the dialysate loop 20. Typical ranges for the volumes of the electrode rinse solution and concentrate solutions provided are 100-5,000 mL. Typical ranges of flow rates for the electrode rinse solution, the concentrate and the diluate solutions are 100-10,000 mL/min. In some embodiments, the system contains from about 2 to about 6 L of aqueous-based fluid. In other embodiments, the system contains any of from about 2 to about 10 L, from about 1.5 to about 5 L, from about 2 to about 8 L, or from about 2 to about 5 L of aqueous-based fluid.

A primary conditioning unit 114 is placed before the electrodialysis unit 122 to contact spent dialysate before it enters the electrodialysis unit 122. The primary conditioning unit 114 converts the urea, a neutral molecule, into ammonium ($NH_4^+$), an ionic species. This conversion may take place through various means, including electrical, optical, thermodynamic or chemical processes. For the case of chemical processing of urea, the catalytic enzyme urease can be used to convert urea into ammonium. The ammonium ions then enter into the electrodialysis 122 via the intake portal 232 of the electrodialysis unit 122, as shown in FIG. 6, and removed through the action of the electrical field. The primary conditioning unit 114 can also contain activated carbon for the removal of creatinine and uric acid from the dialysate, which are neutral or substantially neutral species at typical pH values for the dialysate. The primary conditioning unit 114 can also contain ion-exchange resin to remove $Ca^{2+}$ and $Mg^{2+}$, which may minimize membrane fouling due to precipitation and increase the membrane life in the electrodialysis unit.

As shown in FIG. 7, the concentrate solution and electrode solution are recirculated by pumps 110 and 112, respectively. During operation of the electrodialysis unit 122, the concentration of waste species within the recirculating concentrate solution and electrode solution increases with time. When particularly high concentrations of waste species build-up in the concentrate solution and the electrode solution, the operation of the electrodialysis unit 122 can be affected. As such, reservoirs 108 and 106 can contain a volume of concentrate solution and electrode solution, respectively, such that waste impurities will not build up to an inoperable level during a typical treatment session. That is, volumes of concentrate solution and electrode solution are provided such that the transfer of substantially all of the urea, which is the primary waste species, from a patient in one transfer session (approx. 20 grams) will not adversely affect the operation of the electrodialysis unit 122.

An additional conditioning unit 116 can be present at an outlet of the electrodialysis unit 122 that can contain activated carbon or another sorbent to remove non-ionic waste species. Further, the additional conditioning unit 116 can contain a sorbent to absorb ammonium ions, such as zirconium phosphate or another zirconium-containing sorbents. The electrodialysis unit 122, in some instances, may not remove all of the ammonium ions from the diluate solution. As such, residual ammonium ions can be removed by conditioning unit 116. Zirconium phosphate and other zirconium-containing sorbents are expensive consumable materials. As such, the use of electrodialysis unit 122 to remove the large majority of ammonium ions generated from urea in conjunction with conditioning unit 116 consumes less than 10% of the ammonium sorbents compared to systems relying solely upon zirconium phosphate or other zirconium-containing sorbents to remove ammonium ions. In conditioning unit 116, a cation exchange resin or a mixed-bed cation/anion exchange resin can also be present to remove other residual ions and substances (e.g. $Na^+$, $K^+$, $Mg^{2+}$, $Ca^{2+}$).

Although the electrodialysis unit 122 of the purification unit 30 can remove up to 90% of the ions from solution, remaining ions may need to be removed using the sorbents in additional conditioning 116, as explained above. However, there is a possibility of ions to be returned to the dialysate circuit 20. As such, sensors 74, 75 and 76 located in the dialysis circuit 20 and the infusate set 35 can be used to determine the ionic concentration of the fluid reentering the dialysate loop, where the electronic controller can then infuse a reduced amount of infusate solutions into the dialyzer circuit 20 to achieve a desired dialysate composition. In particular, where sensors 74, 75 and 76 include a conductivity sensor and a potassium-sensitive electrode, a proper amount of a potassium salt and other salts can be added in response to ionic substances entering the dialysate loop. Further, an ammonium ion sensor 53 can be present since any ammonium ions reaching the patient or the hemodialysis unit 15 can be dangerous. Dialysate flow to the patient and/or hemodialysis unit 15 can be stopped if the presence of ammonium ions is detected.

For example, at the onset of the dialysis session, the serum potassium level can hypothetically be 7 mM, which can be approximated by the dialysate return composition sensor 25. If the 90% of the potassium ions are removed by the electrodialysis unit 122, then the remaining potassium ion concentration would then be 0.7 mM, which would be detected by the set of sensors 74, 75 and 76 (not all sensors are required in all embodiments). If the desired potassium ion concentration in the dialysate is 4 mM, then the infusate set 35 can add an amount of potassium salt to bring the concentration from 0.7 to 4 mM. Using such a feedback technique, the needed amount of infusate solutions and sorbent materials are reduced.

Figure 8:
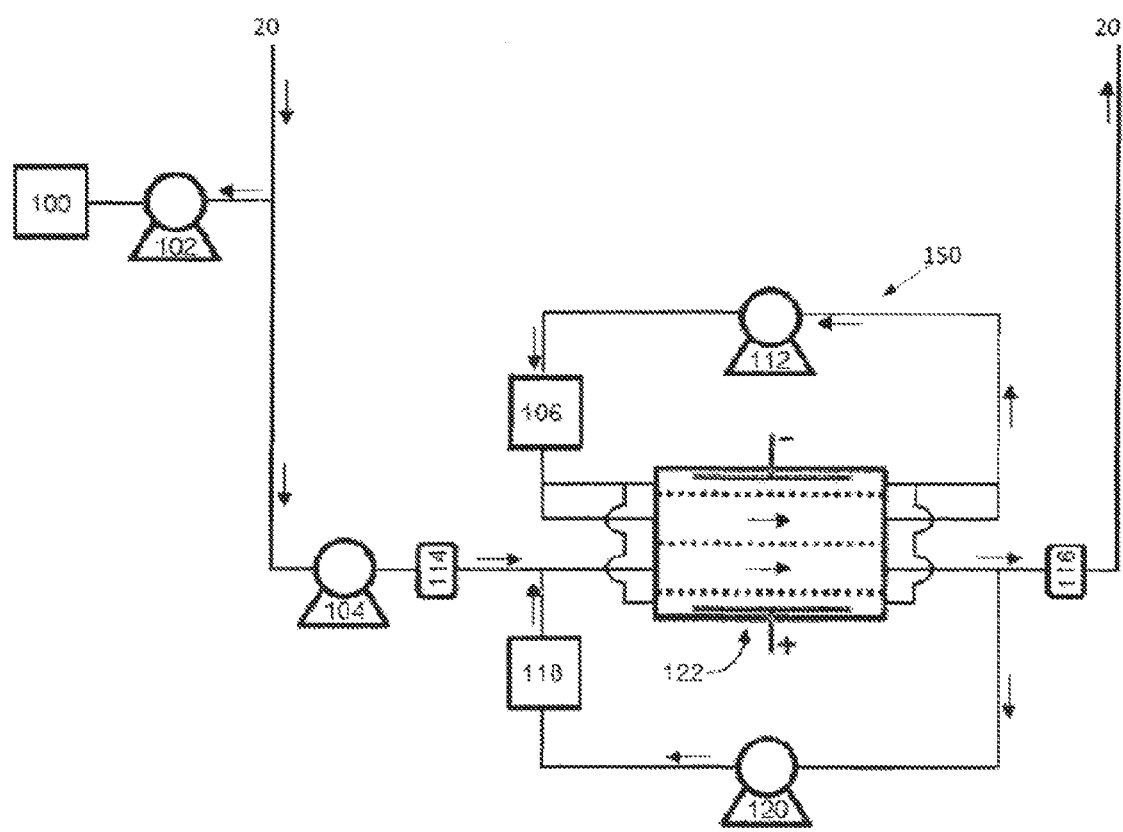
FIG. 8 shows a schematic for an embodiment of a purification module in accordance with some embodiments.

FIG. 8 shows another embodiment of the invention. In this embodiment, the electrode solution and the concentrate solution are mixed through passage of reservoir 106 and the resulting solution circulated using the pump 112. As such, one pump and one reservoir are removed from the purification module 30 when compared to the embodiment as shown in FIG. 7.

Figure 9:
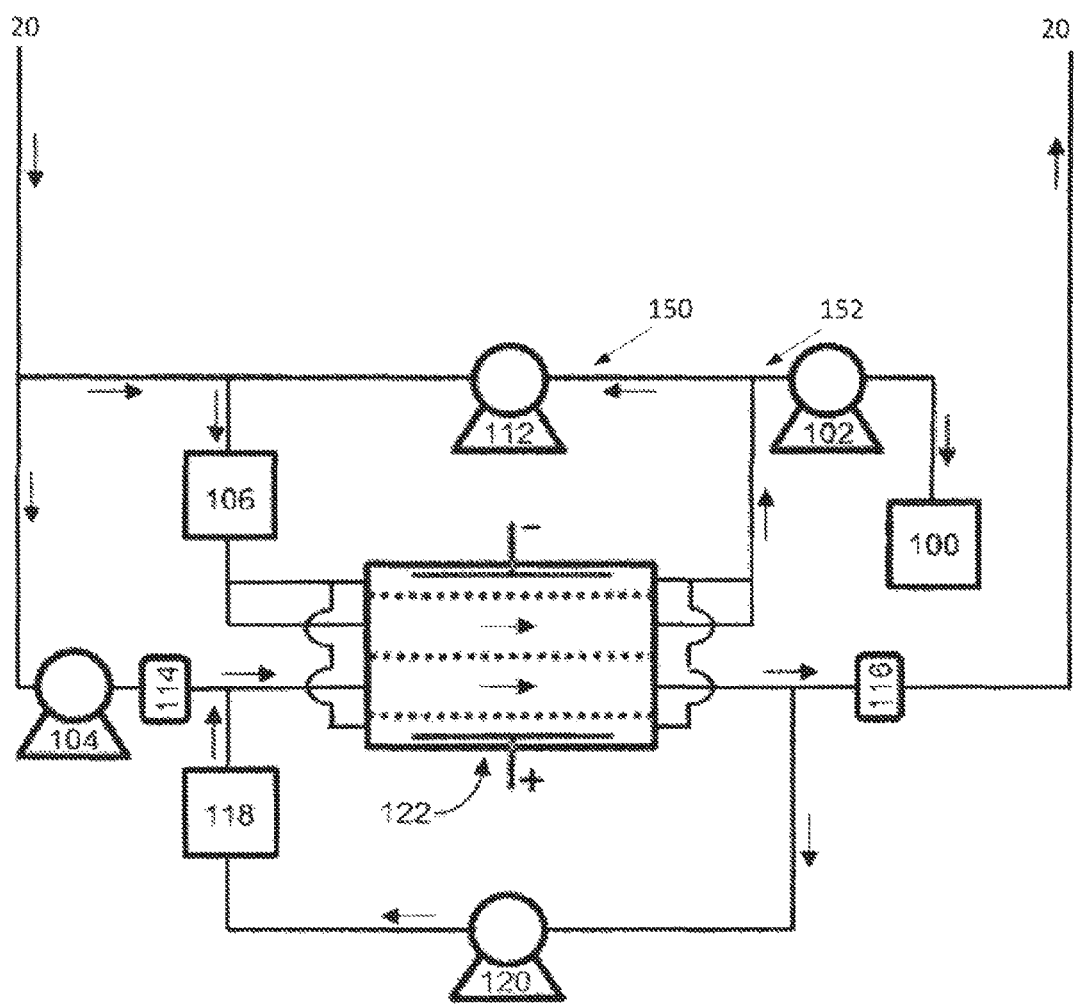
FIG. 9 shows a schematic for an embodiment of a purification module in accordance with some embodiments.

A further embodiment is shown in FIG. 9. The concentrate solution and electrode solution are circulated via pump 112 and stored in a combined reservoir 106. In the embodiment shown in FIG. 9, a means is provided for diluting the concentration of the solution stored in reservoir 106. The control pump 102 and reservoir and drain 100 are attached to the concentrate solution and electrode solution recirculation loop 150 via a conduit 152. As such, operation of the control pump 102 draws fluid from the dialysate loop 20 into reservoir 106. As such, a small amount of fluid is obtained from the dialysate loop 20 and used to reduce the concentration of ions in the concentrate solution stored in reservoir 106. An equal volume of more concentrated concentrate solution is removed to reservoir/drain 100 by the control pump 102. As such, the build-up of ammonia and other waste species in the concentrate solution can be limited.

In the embodiment shown in FIG. 9, operation of the control pump 102 can affect ultrafiltration by drawing fluid from the blood circuit 10 into the dialysate circuit 20. However, operation of the control pump 102 does not necessarily result in an equal migration of fluid into the dialysate circuit 20 from the blood circuit 10, since an amount of water can be added to the control circuit 20 in conjunction with operation of the control pump 102 as discussed above.

Figure 10:
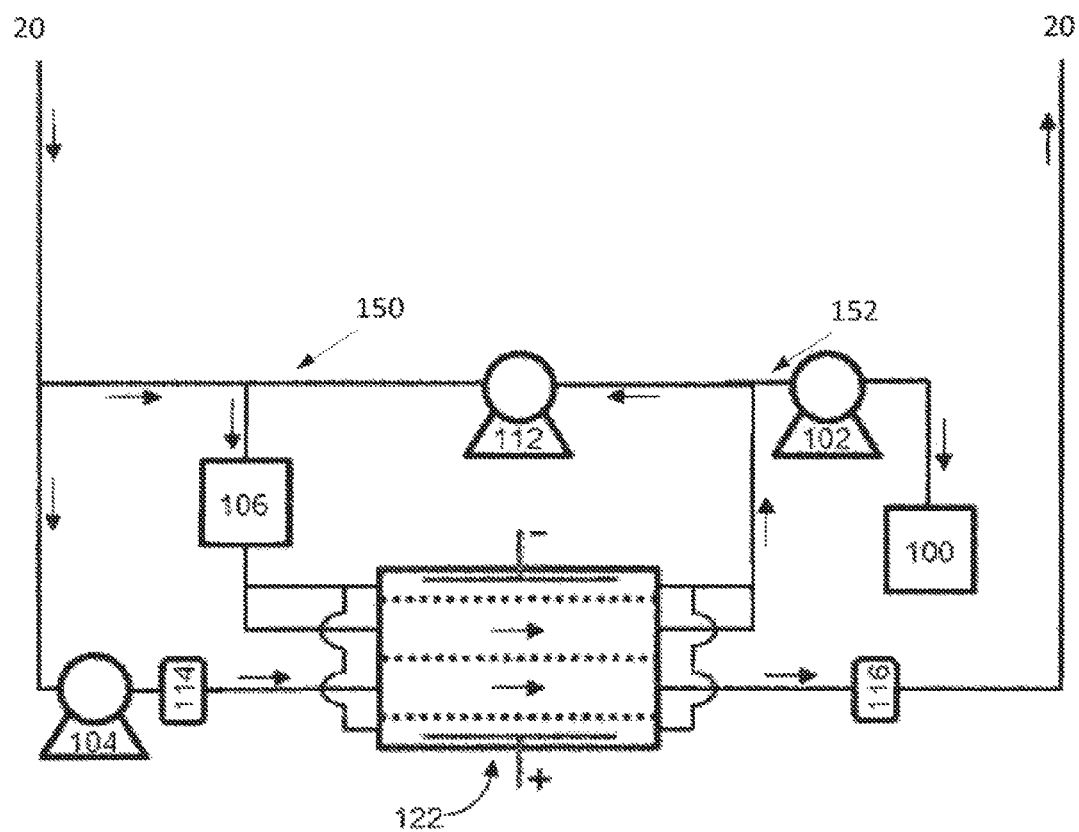
FIG. 10 shows a schematic for an embodiment of a purification module in accordance with some embodiments.

A further embodiment is shown in FIG. 10. The embodiment shown in FIG. 10 is largely parallel to the embodiment shown in FIG. 9. However, the diluate circulation pump 120 and the diluate reservoir 118 are eliminated to save space in the purification unit 30.

Figure 11:
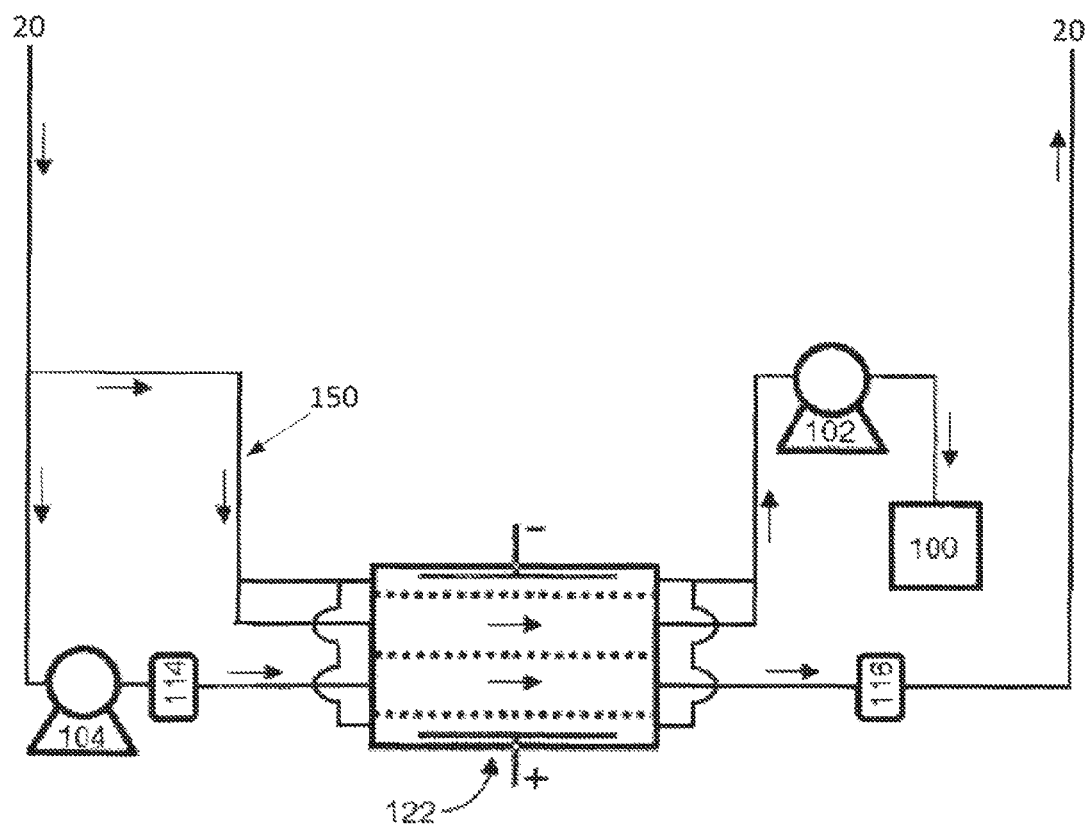
FIG. 11 shows a schematic for an embodiment of a purification module in accordance with some embodiments.

A still further embodiment is shown in FIG. 11 that simplifies operation of the purification unit 30. In this embodiment, the concentrate circulation pump 112 and the concentrate reservoir 106 are in the purification module unit 30. In FIG. 11, the concentrate solution is not re-circulated. Rather, a portion of the dialysate entering the purification unit 30 is diverted through the concentrate and/or electrode chambers of the electrodialysis unit 122 through operation of the control pump 102 to draw dialysate into conduit 150. This amount of diverted dialysate is then discarded into reservoir/drain 100.

Figure 12:
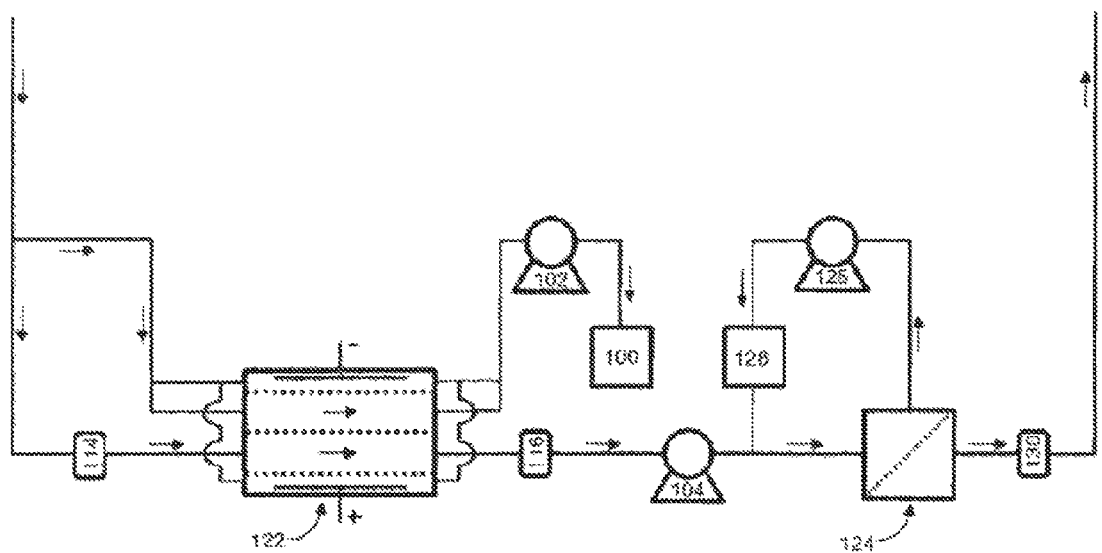
FIG. 12 shows a schematic for an embodiment of a purification module in accordance with some embodiments.

An additional embodiment is shown in FIG. 12. The embodiment shown in FIG. 12 lacks a concentrate circulation pump 112 or concentrate reservoir 106. A reverse osmosis unit 124, a high-pressure pump 104 and a high-flow pump 126 along with a reservoir 128 are added in-line with the electrodialysis unit 122. The reverse osmosis unit 124 allows for a more complete removal of the solutes from the dialysate. Reverse osmosis uses a filter-based technique to remove both ionic and non-ionic species. In reverse osmosis, a hypotonic solution is separated from a hyper tonic solution via a membrane that is permeable to a solvent (e.g. water) but impermeable to solute. A high pressure is applied to the hypertonic solution to counteract osmotic pressure and drive solvent from the hypertonic solution to the hypotonic solution. Here, the hypertonic solution is the diluate solution exiting the electrodialysis unit 122 that can still contain some waste species. Pressure from high-pressure pump 104 drives solvent from the diluate solution into a pure water compartment within the reverse osmosis unit 124. The diluate circuit can be re-circulated by pump 126 to increase the efficiency of reverse osmosis.

Figure 13:
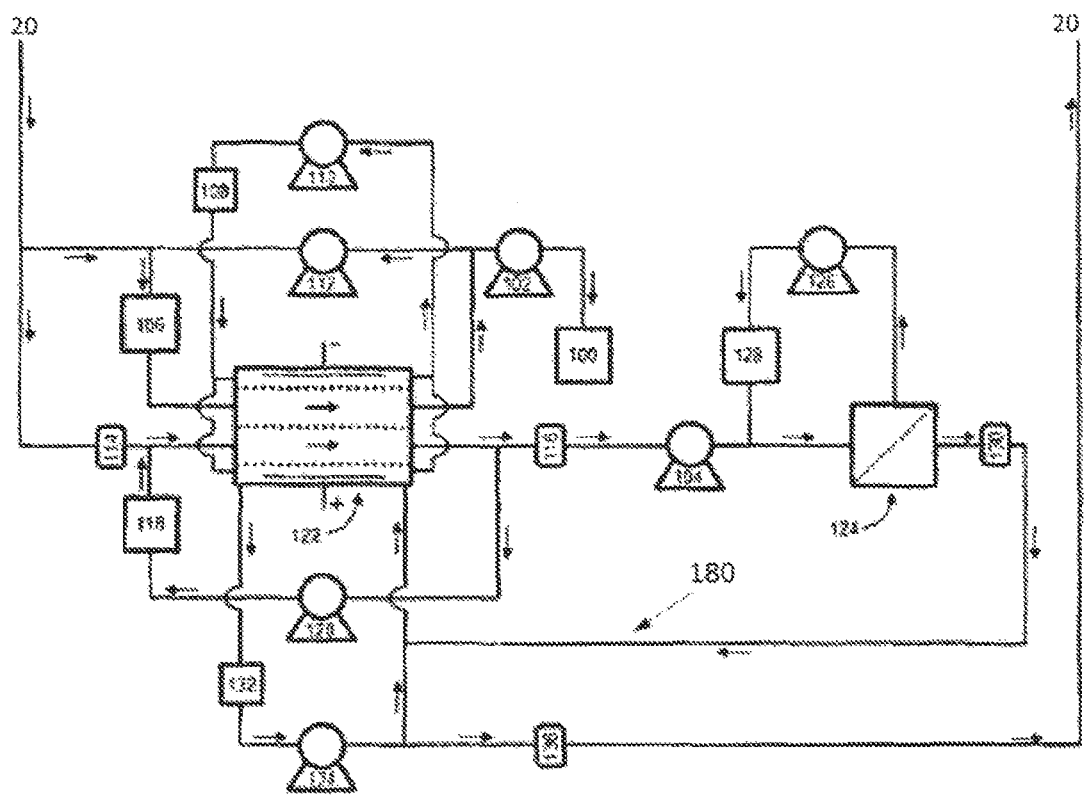
FIG. 13 shows a schematic for an embodiment of a purification module in accordance with some embodiments.

An additional embodiment employing a reverse osmosis unit 124 is shown in FIG. 13. Element numbers in FIG. 13 conserved from FIGS. 7 and 12 refer to like elements. In the embodiment shown in FIG. 13, three separate reservoirs 108, 106 and 118 are used along with pumps 110, 112 and 120 to circulate an electrode rinse solution, a concentrate solution and a diluate solution, respectively. Again, the diluate solution is the solution used for the regeneration of the dialysate. As in FIG. 7, the diluate solution can be re-circulated via the pump 120 to increase the flow rate of the diluate over and beyond the flow rate of the dialysate within the dialysate loop 20, which is circulated via the pump 134 through the dialysate loop 20.

The portion of the diluate exiting the electrodialysis unit 122 not re-circulated by pump 120 is passed through a conditioning unit 116 and a high-pressure pump 104 and a reverse osmosis unit 124. Optionally, the diluate solution can be re-circulated through the reverse osmosis unit 124 using pump 126 and reservoir 128 as shown. After diluate solution passes through the reverse osmosis unit 124, it returns back to the electrodialysis unit 122 through a separate, secondary, diluate feed line 180 as shown. The electrodialysis unit 122 can include a separate set of diluate chambers to accommodate the flow of the secondary diluate through the electrodialysis unit 122. The secondary diluate can also include a secondary diluate reservoir 132 and a secondary diluate pump 134 that both re-circulate part of the secondary diluate as well as provide for circulation through the dialysate loop 20. Also, a final conditioning unit 136 can be included to remove components that were not completely removed by the up-stream components.

For embodiment shown in FIG. 13, the primary conditioning unit 114 can contain activated carbon and/or an ion-exchange resin; however, urease need not be present in primary conditioning unit 114. The secondary conditioning unit 116 can contain an additional ion-exchange resin and/or activated carbon. A tertiary conditioning unit 130 located at the outlet of the reverse osmosis unit 124 can contain urease (typically attached to a resin) to break down urea that has made it through the reverse osmosis unit 124. As described above, the fluid exiting the reverse osmosis unit 124 and tertiary conditioning unit 130 is returned to the electrodialysis unit 122 via the secondary diluate line 180.

That is, FIG. 13 presents an embodiment where the spent dialysate solution from the dialysate circuit 20 passes through the electrodialysis unit 122 without converting urea to a charged species. As such, the electrodialysis unit 122 serves to remove ions from the spent dialysis fluid (e.g. $Na^+$, $K^+$, $Cl^-$, etc.) while urea is not removed. The primary diluate thus formed is then passed to a reverse osmosis unit 124 which can remove charged as well as uncharged species such as urea. As such, the concentration of urea in a diulate is reduced prior to contact with a tertiary conditioning unit 130 containing urease for the generation of ammonium ions. Because the urea concentration is significantly reduced by the reverse osmosis unit 124, potentially up to 80% less urease can be required in tertiary sorbent cartridge 130 compared with other embodiments discussed above. As such, size and overall operating cost can be reduced. The final conditioning unit 136 can contain an ion-exchange resin to remove any remaining dialysate impurities, such as ammonium, phosphate, calcium, potassium, etc. not removed by up-stream components.

System Communication

Figure 14:
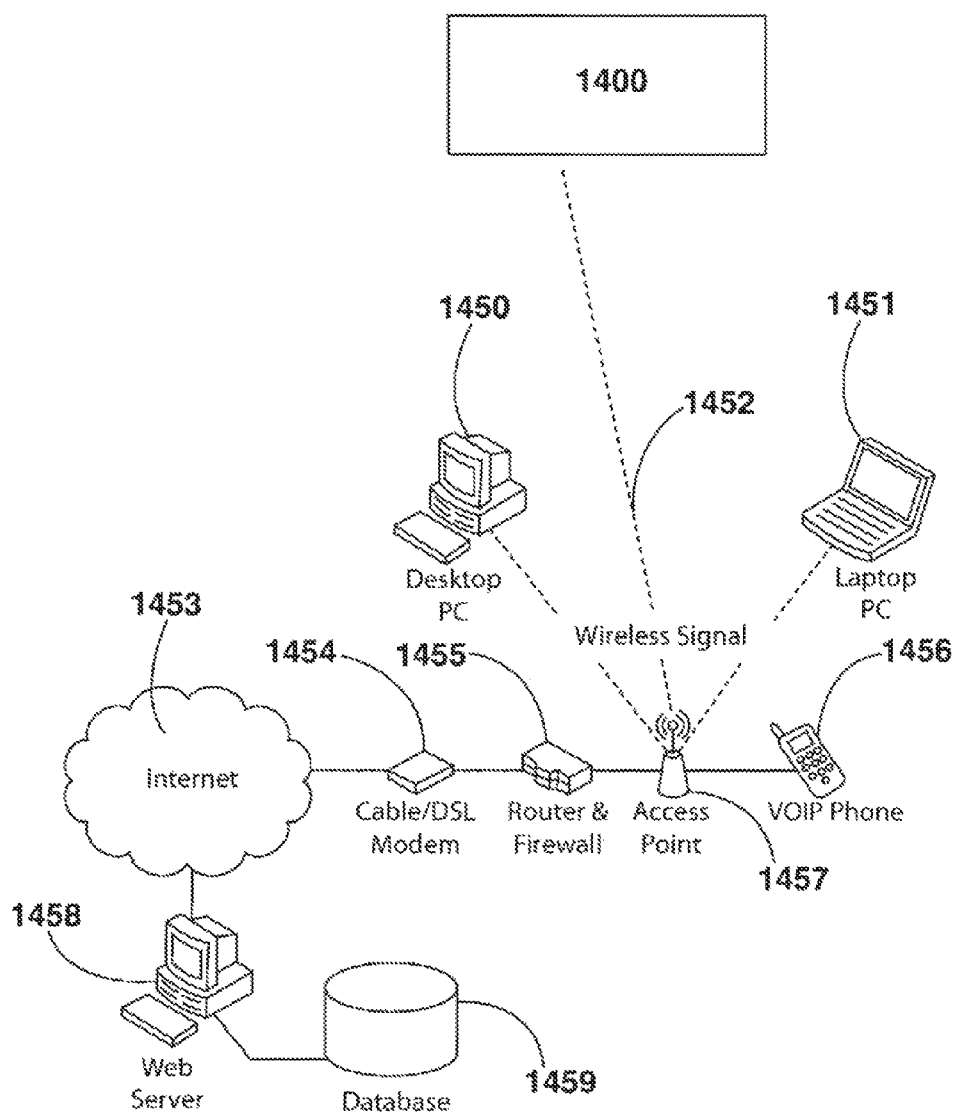
FIG. 14 shows a communication system in accordance with some embodiments.

The electronic controller 1400 of FIG. 14 can monitor pump rates of the system as well as monitor potassium removal and ultrafiltration as described above. For example, the electronic controller 1400 can transmit information based on data from the sensors to a remote device via a computer network, pager network, cellular telecommunication network, and/or satellite communication network, or via an RF link such as Bluetooth, WiFi, or MICS or as described in U.S. Pat. No. 5,683,432 "Adaptive Performance-Optimizing Communication System for Communicating with an Implantable Medical Device" incorporated herein by reference in its entirety, wherein there is no requirement for the electronic controller to be implanted within the patient.

In certain embodiments, the invention includes a telemetry circuit that enables programming by means of a 2-way telemetry link. Uplink telemetry allows device status and diagnostic/event data to be sent a physician or another party for review to track the treatment of a patient. Downlink telemetry allows the programming of device functions of the electronic controller to be performed by parties other than the patient, for example, specific parameters for controlling potassium ion concentration in the dialysate, and the optimization of the therapy for a specific patient. Known telemetry systems suitable for use in the practice of the present invention are contemplated by the invention. Communication with the electronic controller is typically done via a bi-directional radio-frequency telemetry link, such as the CareLink™ system (Medtronic, Inc., Minneapolis, Minn.).

As shown in FIG. 14, in some embodiments, data from the external controller 100 and/or programming of the external controller can be accomplished through a number of different external devices. The external controller can be in communication with an access point 1457, such as a WiFi access point. The patient can use different types of devices, running applications for sending and receiving data from the external controller 1400, such as a desktop 1450 or laptop PC 1451 or a cellular phone or smart phone device 1456. In some embodiments, data can be transmitted over the internet 1453 via a local router 1455 and modem 1454 for placement on a secure web server 1458 and associated database 1459. The web server 1458 can be accessed by the patient and/or a physician or clinician to update programming of the electronic controller 1400 or to monitor the progress of treatment.

Various telemetry systems for providing the necessary communications channels between an electronic controller and a medical device have been developed and are well known in the art, for example, Telemetry systems suitable for the present invention include U.S. Pat. No. 5,127,404, entitled "Telemetry Format for Implanted Medical Device"; U.S. Pat. No. 4,374,382, entitled "Marker Channel Telemetry System for a Medical Device"; and U.S. Pat. No. 4,556,063 entitled "Telemetry System for a Medical Device," which are all incorporated herein by reference.

Operation of System in Electrodialysis Mode and In-Center Mode

Figure 15:
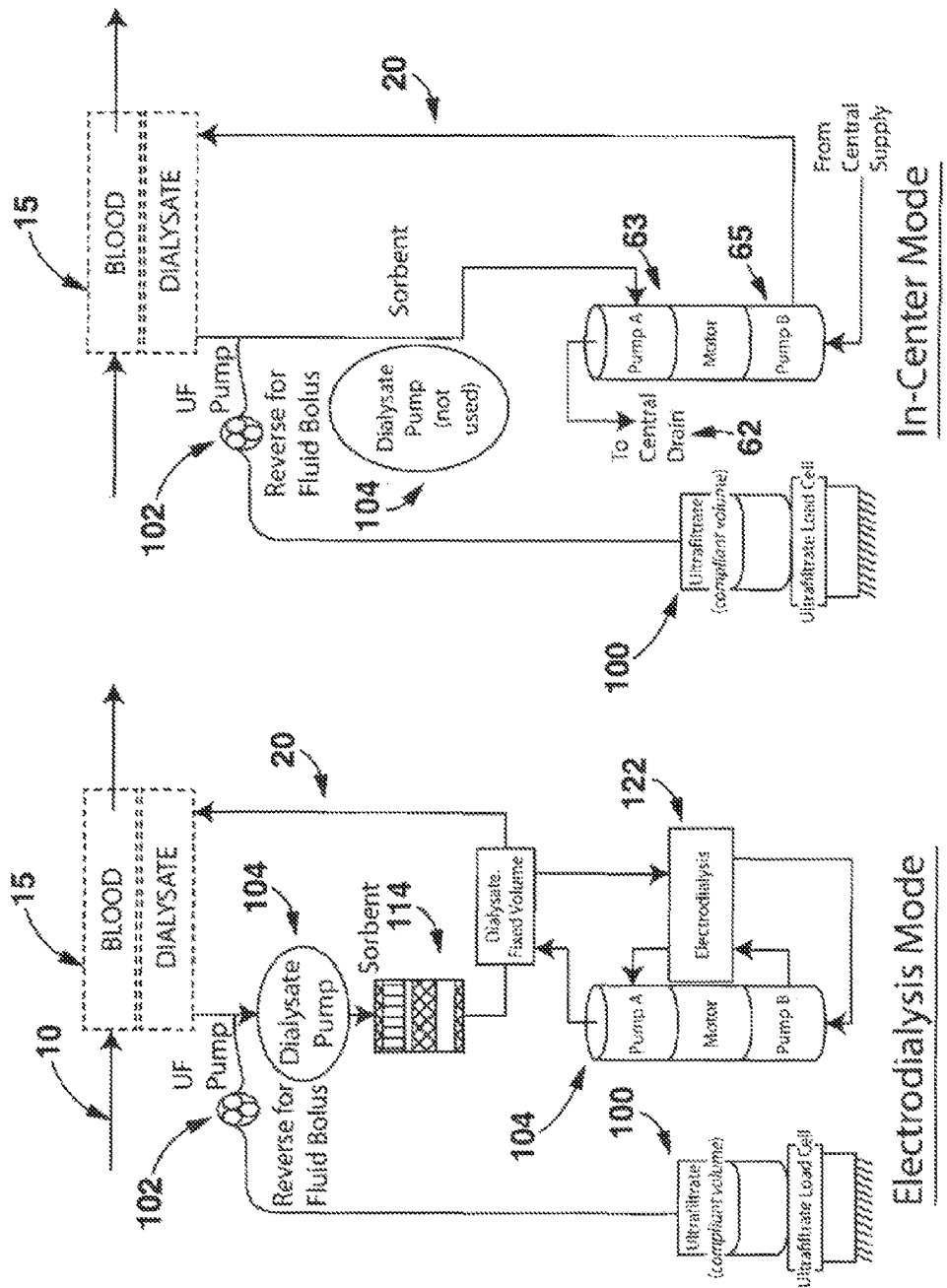
FIG. 15 shows a flow diagram for use of a dual purpose, single-drive reciprocating metering pump in the described systems.

FIG. 15 shows the operation of the device in both modes with electrodialysis regeneration of a fixed volume of dialysate and "in-center" mode with a supply of fresh water. In both modes, dialysate is transported through the dialysis circuit 20 and blood is conveyed through the blood circuit 10, wherein dialysis occurs in the dialyzer 15. Both modes also can make use of a control pump 102 to affect ultrafiltration and bulk removal of fluid from a patient. The two modes differ in that a pump 104 need not be present to drive dialysate flow through dialysis circuit 20 in the "in-center" mode. Rather, dialysate flow is supported by pumps supplying fresh water from the treatment center. Similarly, the electrodialysis unit need not be present nor conditioning unit 114 involved with the regeneration of dialysate.

Cleaning and Disinfection

Figure 16:
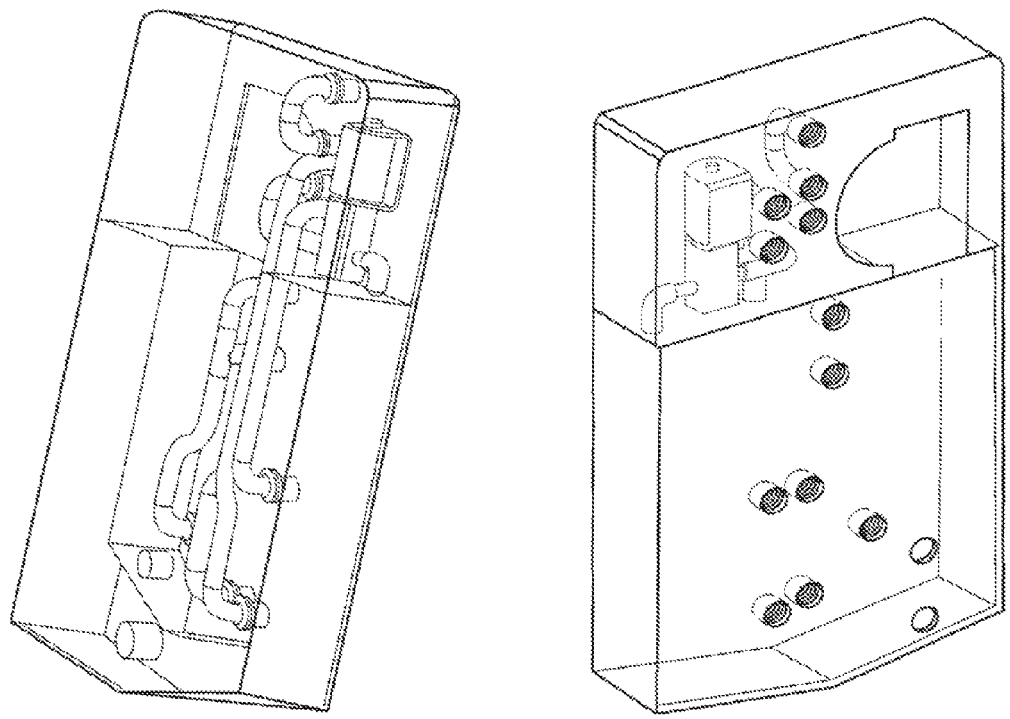
FIG. 16 illustrates the cleaning and disinfection manifold for use in the described systems.

After each use, the system is cleaned and disinfected to prevent the accumulation of biological pathogens, such as bacteria, spores and viruses. This is accomplished by first the removal and disposal of the dialyzer 15, blood circuit 10 and vascular access device 5. Afterwards, a cleaning and disinfection manifold (FIG. 16) is placed in the place of dialyzer 15 and the dialysate loop 20 is flushed with fresh water. If the device was used as a stand-alone unit, then the sorbent cartridges are removed from the primary and secondary conditioning units, 114 and 116 respectively, and replaced with cleaning cartridges containing a cleaning solution, such as citric acid. The built in electrical heater 90 on the dialysate circuit 20 is turned on to bring the temperature of the solution in the dialysate loop to 85 degrees Celsius while the cleaning solution circulates in the dialysate circuit 20 for at least one hour. The system remains idle until the next usage.

Control of Ultrafiltration, Fluid Removal, Fluid Replacement, and Fluid Monitoring As described above, the controlled compliance dialysis circuit can be used to accurately control the bulk movement of fluid across the dialysis membrane in hemodialysis unit 15. The blood circuit 10 functions as an extracorporeal extension of the patient's body. As such, the net movement of fluid from the dialysate circuit 20 to the blood circuit 10 effectively adds fluid to the blood compartment of the patient Likewise, the net movement of fluid form the blood circuit 10 to the dialysate circuit 20, or ultrafiltration, effectively removes fluid from the blood compartment of the patient.

The blood and circulation of a patient is in balance with the interstitial fluids of the patients or body compartment fluids of the patient. That is, as blood volume or fluid is reduces, the removed blood volume or fluid will be replaced by fluid moving into the blood compartment from the body compartment. However, this process of equilibration between the blood compartment and the body compartment takes time and is not instantaneous. In addition to difficulties in removing impurity components such as urea or maintaining electrolyte balance, patients with KD can similarly have problems removing fluid from the body. As such, dialysis treatment can include the removal of fluid from the blood compartment via the blood circuit 10, which has the effect of drawing fluid out of the body compartment or interstitial areas. However, a removal of fluid from the blood compartment that is too rapid can result in hypovolumia or other adverse effects. As such, in some embodiments, the blood compartment and/or the fluid compartment can be monitored during treatment and adjustments made in the amount of fluid being removed or in the addition of replacement fluid to the patient.

As described above, ultrafiltration or fluid removal from the blood compartment can be accomplished through operation of the control pump 102 in an efflux to remove fluid from the dialysate circuit 20. During operation of the control pump 102 in an efflux direction, the flow rate of fluid exiting the hemodialysis unit 15 is faster than the flow rate of fluid entering the hemodialysis unit 15, wherein the additional fluid exiting the hemodialysis unit 15 originates from the blood present in the blood circuit 10. During treatment, adding a replacement fluid to the blood circuit 10 can become necessary. To accomplish the addition of a replacement fluid, water intake pump 165 can be operated to add fluid into the dialysis circuit 20 to cause a net addition of fluid to the blood circuit 10 across the hemodialysis unit 15 when the unit is operated in electrodialysis mode as described above. During operation in in-center mode, the flow balance between pumps 65 and 63 as described above with proper operation of the flow balance unit 40, as described above. The replacement fluid added to the blood circuit 10 has the composition of the dialysate fluid constituted or re-constituted by the infusion set 35, as described above.

If the rate of fluid removal from the blood compartment is too large, the rate of fluid flow from the tissue compartment may not be sufficient to keep up with the rate of fluid loss from the blood compartment, which can result in hypovolemia or low blood volume. A more moderate differential of fluid loss between compartments may be desired from a patient health perspective. In some embodiments, agents that increase the osmolality of dialysate and thus blood can be used to increase the rate at which fluid is transferred from the tissue or body compartment to the blood compartment of the patient. That is, by increasing the concentration of osmolality enhancer in the dialysate, fluid can be removed from blood at a higher rate as a result of an increase in fluid migration from the body compartment. However, the osmolality enhancer can also pass through the dialysis membrane and increase in concentration in the blood and the blood returned to the patient may have a higher osmolality than the blood removed from the patient. Blood having a higher osmolality will tend to result in more rapid fluid removal from the tissue into the blood. The concentration of the osmolality enhancer used in the dialysate can be changed over the course of a dialysis session; e.g., higher concentration at the beginning and lower concentration at the end. Examples of osmolality enhancers that can be employed include sodium and glucose. Other osmolality enhancers can be used. In lieu of adjusting the osmolality of the dialysate fluid, it may be desirable to monitor fluid loss from the tissue compartment, the blood compartment, or both to determine whether the relative losses or volumes are within a safe range. In some embodiments, suitable ratios of tissue fluid volume to blood fluid volume can be determined on a patient-by-patient basis or can be set initially according to population statistics. As a general rule, decreases in blood volume at a rate of 8 to 10% per hour can cause imminent hypovolemia.

Any suitable sensor can be employed to monitor fluid in the blood compartment or the tissue/body compartment. Examples of sensors and systems that may be employed with regard to blood fluid volumes and tissue fluid volumes are discussed in U.S. Provisional Patent Application No. 61/480,528, filed on Apr. 29, 2011, now expired, and U.S. patent application Ser. No. 13/424,454, filed Mar. 20, 2012, now U.S. 2012/0277655A1 published on Nov. 1, 2012, both entitled FLUID VOLUME MONITORING FOR PATIENTS WITH RENAL DISEASE; and U.S. Provisional Patent Application No. 61/480,530, filed on Apr. 29, 2011, now expired, and U.S. patent application Ser. No. 13/424,467 filed Mar. 20, 2012, now U.S. 2012/0277604A1 published on Nov. 1, 2012, both entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well-studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

Control of the rate of fluid removal (i.e. ultrafiltration) and fluid replacement can be adjusted based upon a ratio of fluid measured between the tissue compartment and the blood compartment. In the embodiment shown in FIG. 17, a dialysis session including blood fluid removal is initiated in step 500 and indicators of tissue fluid volume 510 and blood fluid volume 520 are monitored. The blood fluid removal session can be continuously monitored. The ratio of blood fluid volume to tissue fluid volume is compared, and a determination as to whether the ratio is outside of a predetermined acceptable range is made in step 520. If the ratio is determined to not be outside a predetermined range, the blood fluid removal session continues with the previously set parameters with regard to fluid removal from the blood. If the ratio is determined to be outside the predetermined range, then rate of fluid removal from the blood is altered in step 540.

For example, if the ratio of the tissue fluid volume to blood fluid volume is above the predetermined range, the rate of fluid removal can be decreased. That is, if too much fluid is taken out of the blood or if fluid is removed at a rate faster than the rate at which fluid from the tissue compartment may fill the blood volume, the ratio of tissue fluid volume to blood fluid volume will increase. If the ratio increases to an extent beyond the predetermined range, the rate of fluid removal from the blood can be decreased to allow more time for fluid from the tissue compartment to flow into the blood and bring the fluids in the blood compartment and tissue compartment into appropriate balance and avoid an undesired fluid imbalance that can have negative consequences on patient health.

In contrast, if the ratio of tissue fluid volume to blood fluid volume is below the predetermined range, the rate of fluid removal from the blood can be increased. For example, for purposes of efficiency, it may be desirable to keep a slight, but safe fluid imbalance between the blood compartment and the tissue compartment to drive out excess fluid at a safe and efficient rate. While a low ratio of tissue fluid volume to blood fluid volume may not result in a health risk to the patient (provided that a sufficient volume of fluid is eventually removed), the time in which a patient undergoes a blood fluid removal process may be unnecessarily extended. Thus, by monitoring tissue fluid volume and blood fluid volume during a blood fluid removal session, the rate of fluid removal can be finely controlled based on the monitored indicators to enhance patient safety and to enhance efficiency of the blood fluid removal process.

A ratio of tissue fluid volume to blood fluid volume being too low can also be indicative of too much replacement fluid being added to the blood circuit 10. Accordingly, the rate at which replacement fluid is added can be decreased (which effectively increases the rate of fluid removal for purposes of the present disclosure).

An appropriate range of tissue fluid volume to blood fluid volume can be determined in any suitable manner. For example, the ratio at the patient's dry weight can be defined as the reference. In general, blood is about 7% of body weight and total tissue fluid is about 60% of the body weight (including blood, extracellular and intracellular fluid). Thus, the typical tissue to blood fluid volume ratio of a healthy individual is 53/7, or about 7.6 (e.g., in the range of 6 to 9). This can be used as a starting point for an appropriate ratio of tissue fluid volume to blood fluid volume to be achieved. Alternatively or in addition, the reference ratio can be obtained through a learning process over the course of therapy and can be patient-dependent. The pattern of change of the tissue to blood volume ratio (or indicators thereof) can be optimized through the learning process. As an optimized pattern is learned, it can be used to guide personalized therapy to achieve better outcomes on a patient-by-patient basis.

In some embodiments, a learning algorithm or evolving algorithm that looks at the rate of change of both blood and tissue is used. The difference in rate of change can be used to determine the time constant of the fluid exchange between the tissue and blood compartments. This information can then be used to establish a target on hematocrit (or other indicator of blood fluid volume) for a final state, while taking into consideration the slower transfer between tissue and blood compartments. This could be used to dynamically adjust the fluid removal rate. Limits can be established by patient or clinician input. The initial calibration can be learned or can utilize other information such as weight or other external lab input.

Figure 17:
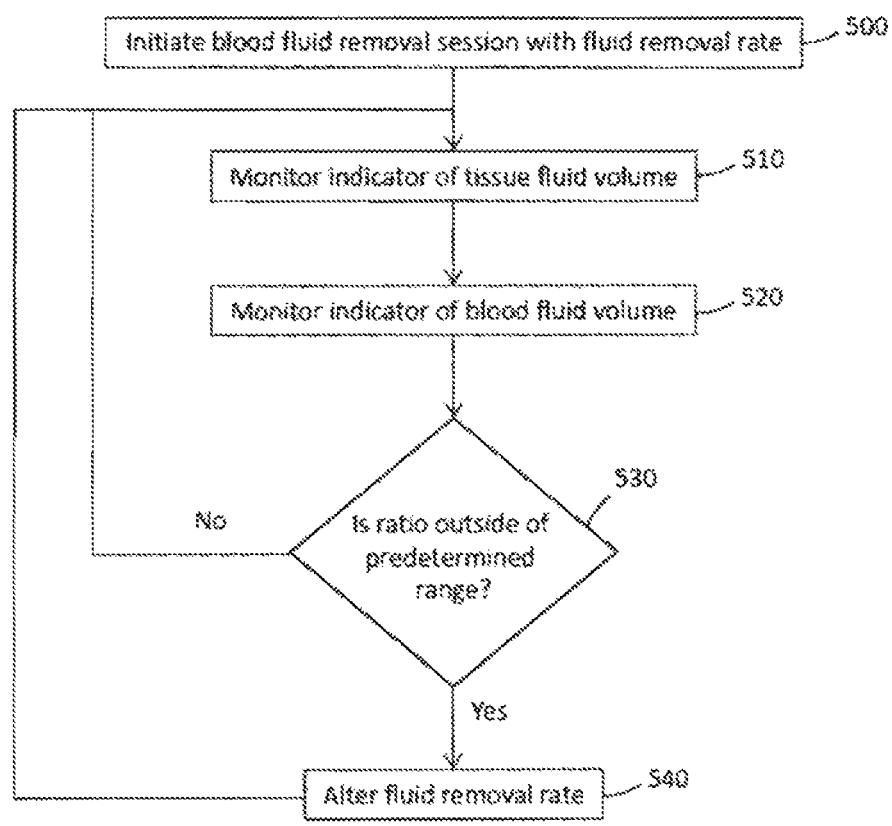
FIGS. 17-21 are flow diagrams depicting overviews of methods in accordance with certain embodiments described herein.
Figure 18:
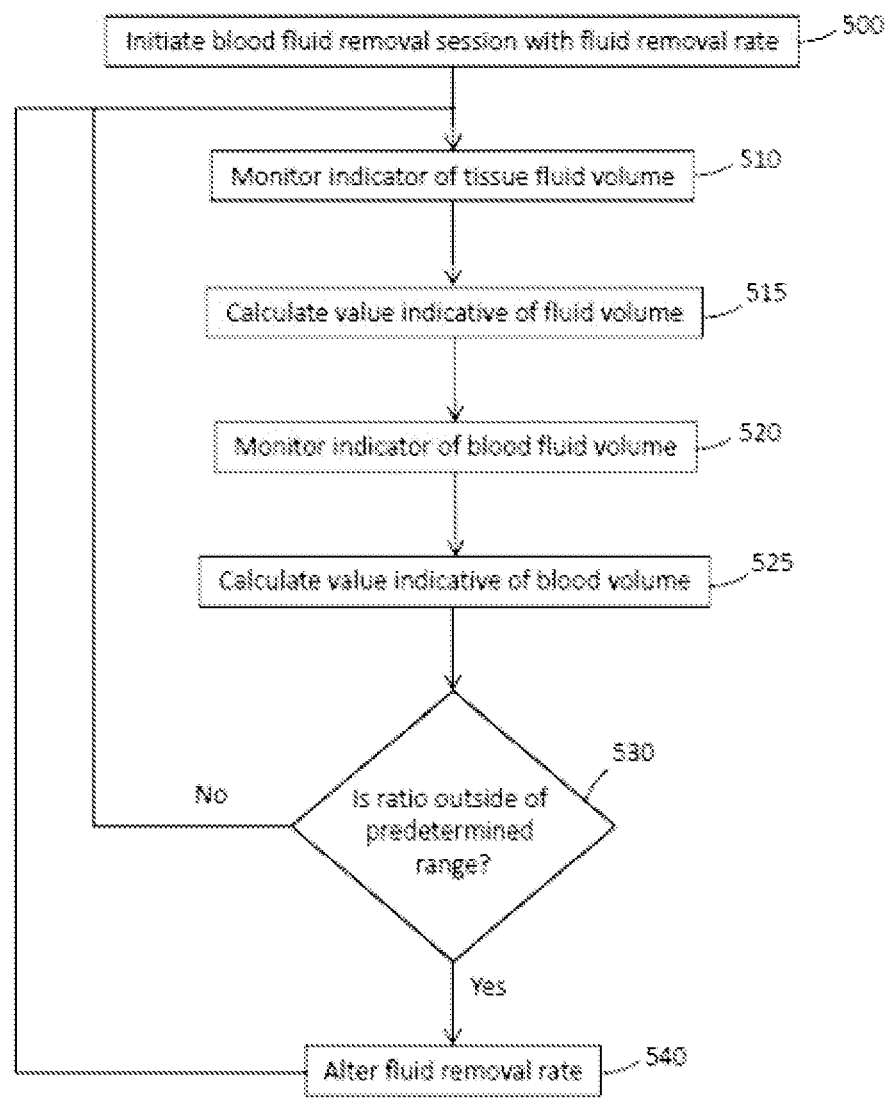

Referring now to FIG. 18, a method shaving details to that depicted in FIG. 17 is shown. In FIG. 18, the method includes calculating a value indicative of tissue fluid volume 515 based on the monitored indicator 510 and calculating a value indicative of blood volume 525 based on the monitored indicator 520. The ratio of tissue fluid volume to blood fluid volume can be determined based on these calculated values 530 rather than on the values obtained with regard to the monitored indicators themselves as depicted in FIG. 17. In either case, the outcome is essentially the same, provided that differences in the way indicators of tissue and blood fluid volume can predict volume are accounted for.

For example, if tissue fluid volume is determined by impedance, an increase in tissue fluid volume would result in an increase in impedance. However, if hematocrit levels were used to determine blood fluid volume, an increase in blood fluid volume would result in a decrease in hematocrit. Accordingly, if the determination regarding the ratios in the embodiment in FIG. 17 took into account that a increase in hematocrit indicates an decrease in blood fluid volume, the end result would be essentially the same as would be obtained in the method of FIG. 18. Put another way, if it was understood and accounted for that the ratio of impedance to the hematocrit changes differently from the ratio of tissue fluid volume to blood fluid volume, the methods of FIG. 17 and FIG. 18 will produce similar results with regard to altering the rate at which fluid is removed from the blood.

Figure 19:
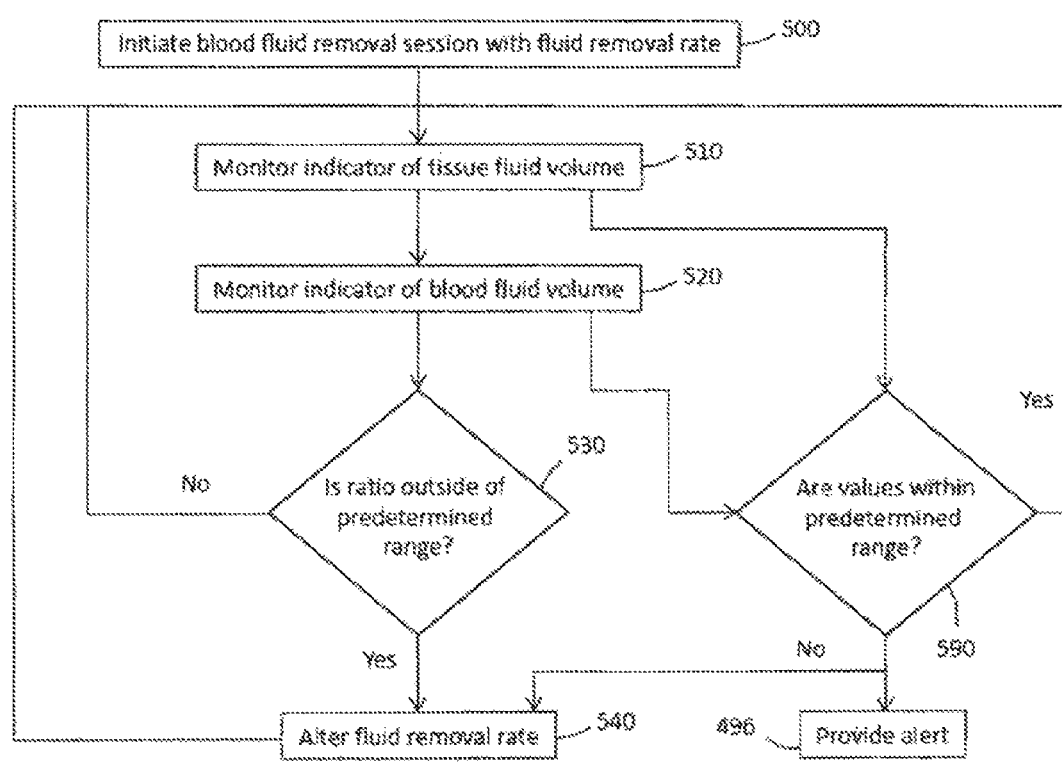

As depicted in FIG. 19, the methods described herein may, in some embodiments, use the monitored indicators of tissue fluid volume 510 or blood fluid volume 520 alone, in addition to the ratio of such values, for purposes of patient safety. As depicted in FIG. 19, it may be determined whether the individually monitored indicator of tissue fluid volume or blood fluid volume is within predetermined acceptable ranges 590. For example, if tissue fluid volume or blood fluid gets unacceptably low (even though the ratio may be within acceptable ranges) or too high, the rate of fluid removal from blood may be altered 540. By way of example, if a value of the indicator of tissue fluid volume is indicative of a near dry weight volume, the rate of fluid removal from blood may be reduced to allow a proper ratio of tissue fluid volume to blood fluid volume to be achieved prior to reaching the dry weight fluid volume. Thus in some embodiments, the threshold for determining whether a value of the monitored indicator of blood of tissue fluid volume is outside of a predetermined range may change based on the ratio of tissue to blood fluid volume. For example, if the ratio of tissue to blood fluid volume is high (indicating a rapid removal of fluid from blood), then the lower threshold for tissue fluid volume (e.g., nearing dry weight) may be higher than if the ratio of tissue to blood fluid volume was low (suggesting less rapid removal of fluid from blood) to avoid overshooting the dry weigh tissue fluid volume.

As also depicted in FIG. 19, an alert such as an audio or visual alarm may be provided 496 to alert the patient or a healthcare provider that a potentially dangerous patient health situation exists with regard to too high or too low fluid volume in the tissue or blood.

Figure 20:
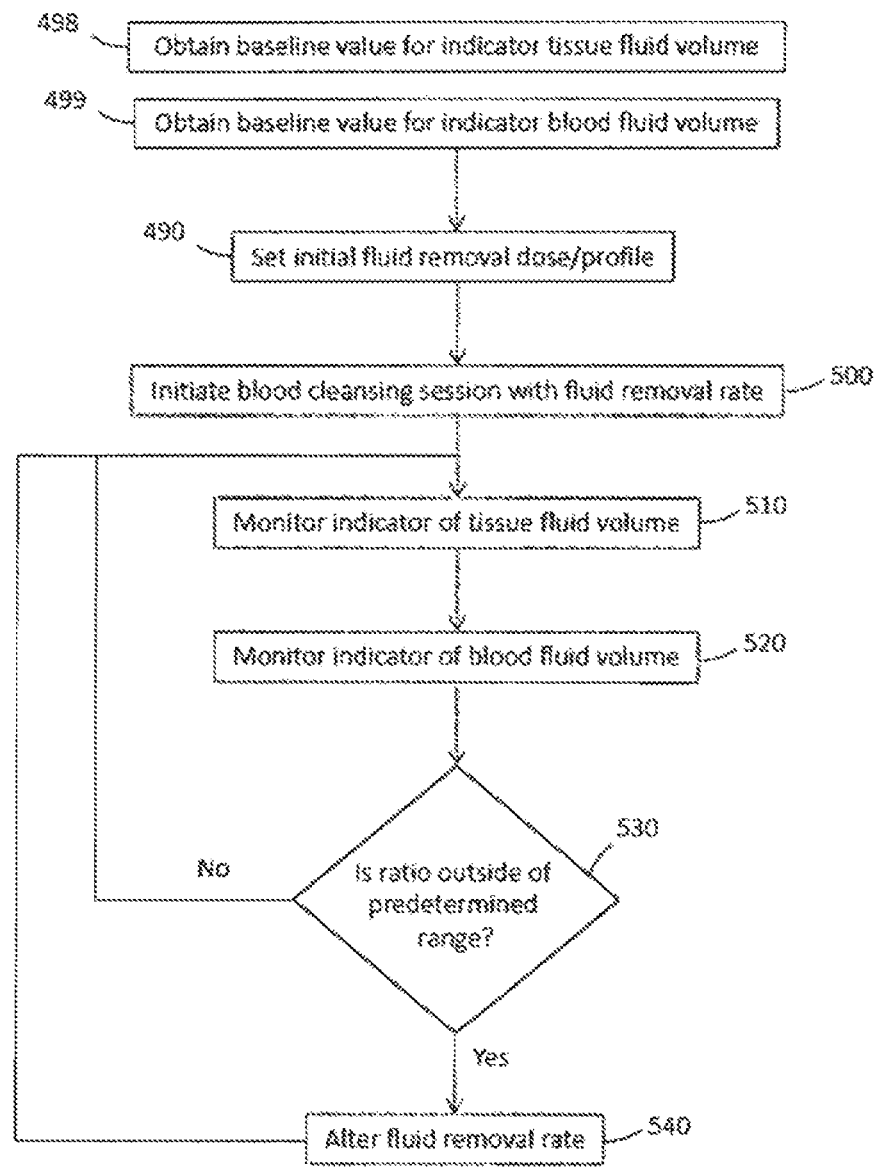

Referring to FIG. 20, a method having similarities to that depicted in FIG. 17 is shown. The method in FIG. 20 includes obtaining a baseline value for an indicator of tissue fluid volume 498 or obtaining a baseline value for an indicator of blood fluid volume 499 prior to initiating a blood fluid removal session 500. One or both of the baseline values may be used to determine the initial dose or prescription for fluid removal for the blood fluid removal session 490. The rate of fluid removal from the blood may be adjusted 540 during the blood fluid removal session based on monitoring 510, 520 that occurs during the session.

Figure 21:
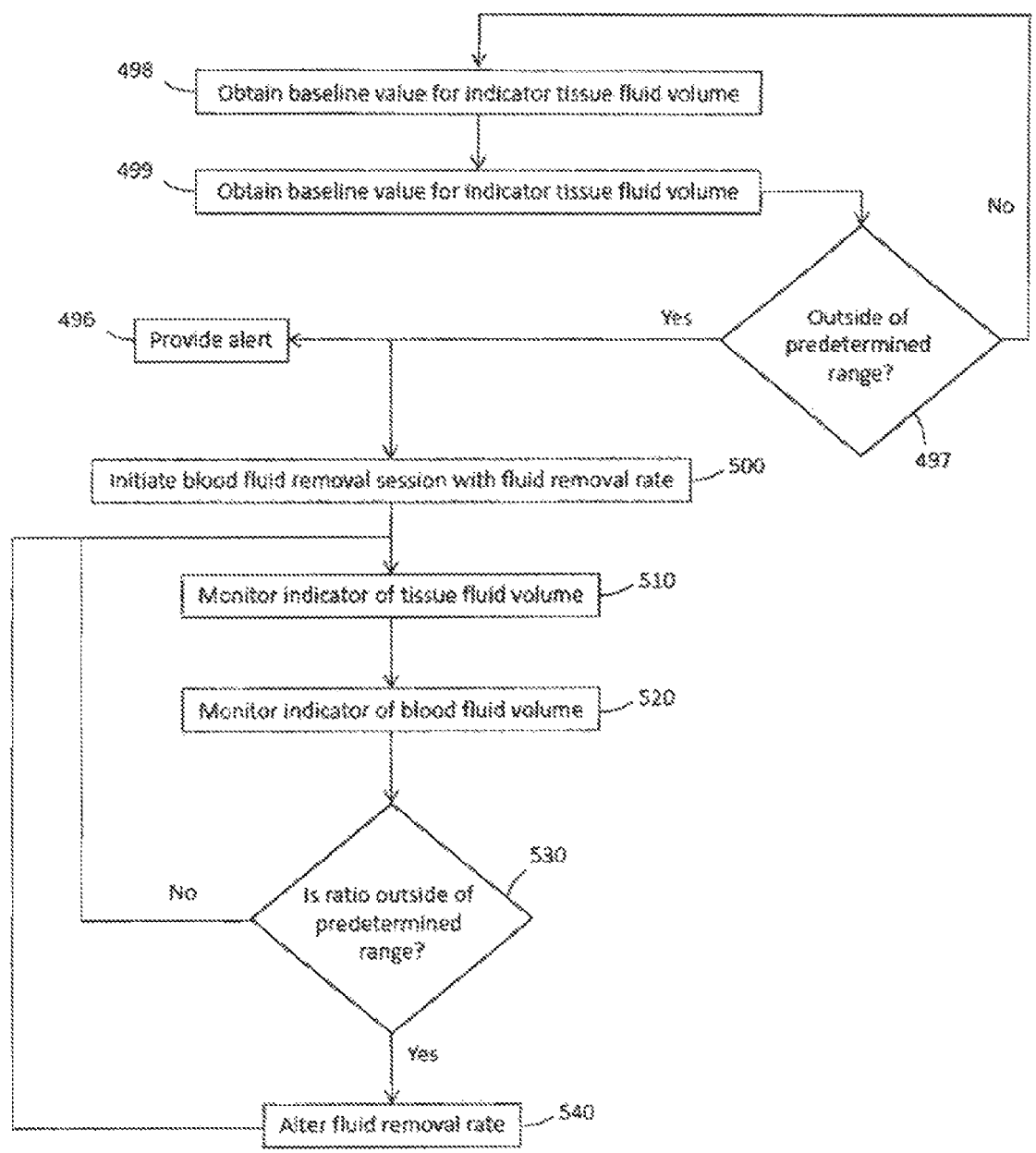

Referring now to FIG. 21, a method having similarities to that depicted in FIG. 17 is shown. The method in FIG. 21, like the method depicted in FIG. 20, includes obtaining a baseline value for an indicator of tissue fluid volume 498 or obtaining a baseline value for an indicator of blood fluid volume 499 prior to initiating a blood fluid removal session 500. If the values are determined to be outside of predetermined acceptable ranges 497, a blood fluid removal session may be initiated 500. Such a method may be advantageously employed in situations where the blood fluid removal device and monitoring sensors are implanted or continuously operating or available to operate, as a blood fluid removal session may be automatically initiated. Alternatively or in addition, the method depicted in FIG. 21 may include providing an alert 496 to the patient or healthcare provider indicating that a blood fluid removal session is advised.

Hypotension is the main complication during dialysis (25-60%). With the methods described herein, which may include real-time blood pressure sensors or other blood volume sensors, imminent blood pressure changes or levels may be predicted, e.g. on a feedforward basis. Accordingly, the rate of fluid removal may be adjusted based on data collected during the fluid removal session to avoid a hypotension situation, as opposed to current standard of care where one starts to adjust the fluid removal rates only when one sees the problems. Dry weight and optimized tissue to blood fluid ratios learned, e.g. as described above, from the therapy course of a patient may help this prediction process to be effective and practical. If necessary or desired, replacement fluid, dialysate or removed fluid may be introduce into the blood circuit 10 to avoid, mitigate or correct a hypotensive event.

Figure 22:
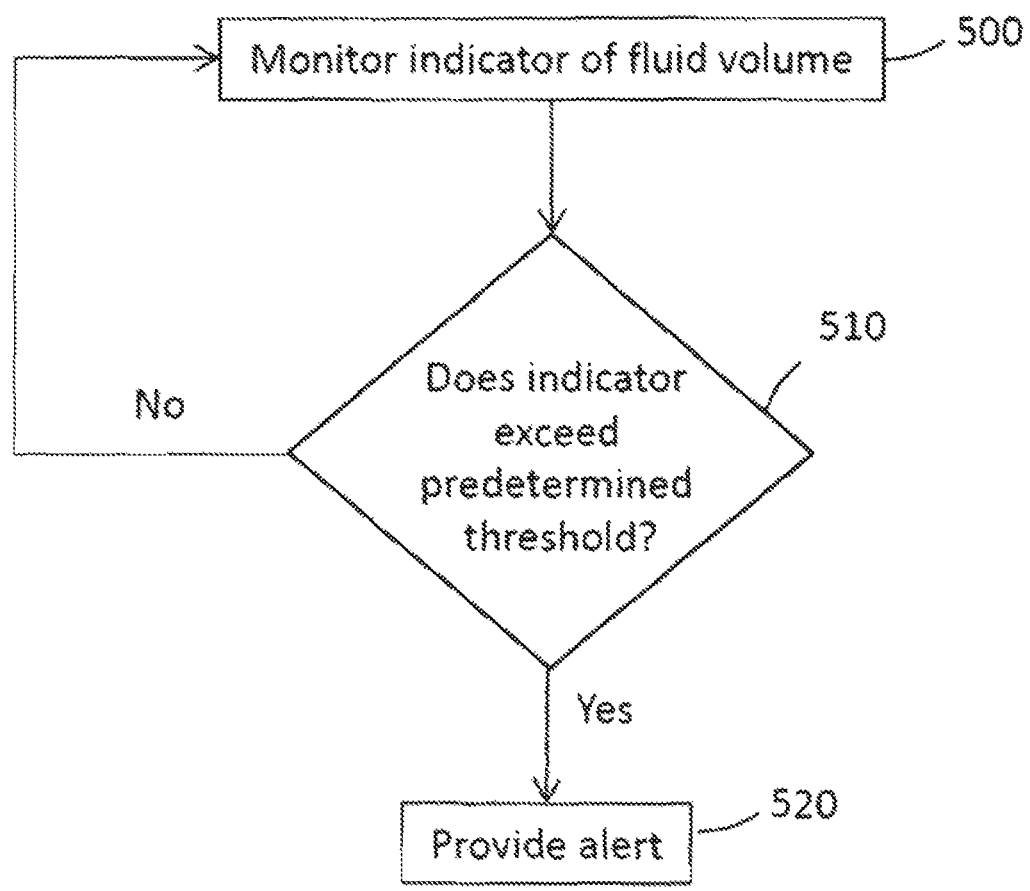
FIGS. 22-24 are flow diagrams depicting overviews of methods in accordance with certain embodiments described herein.
Figure 23:
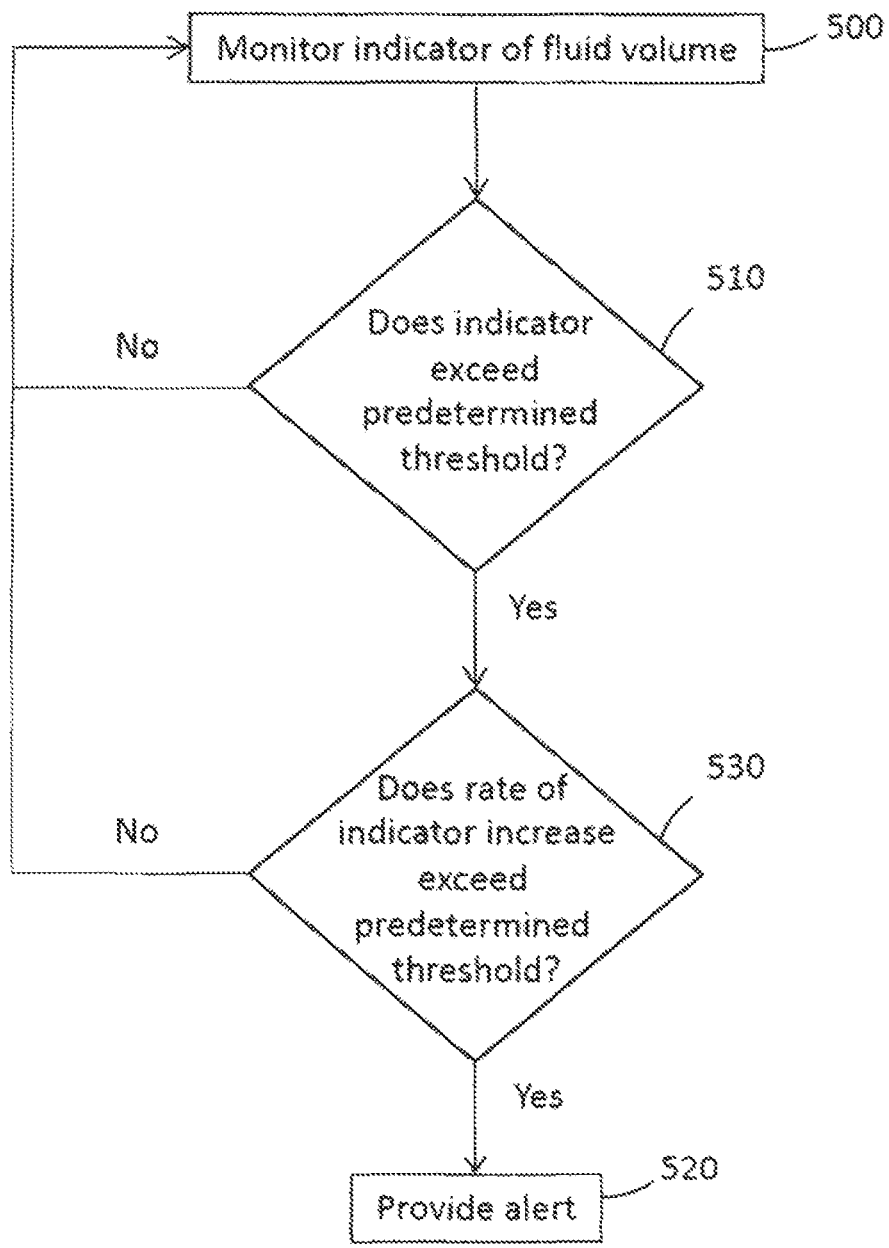
Figure 24:
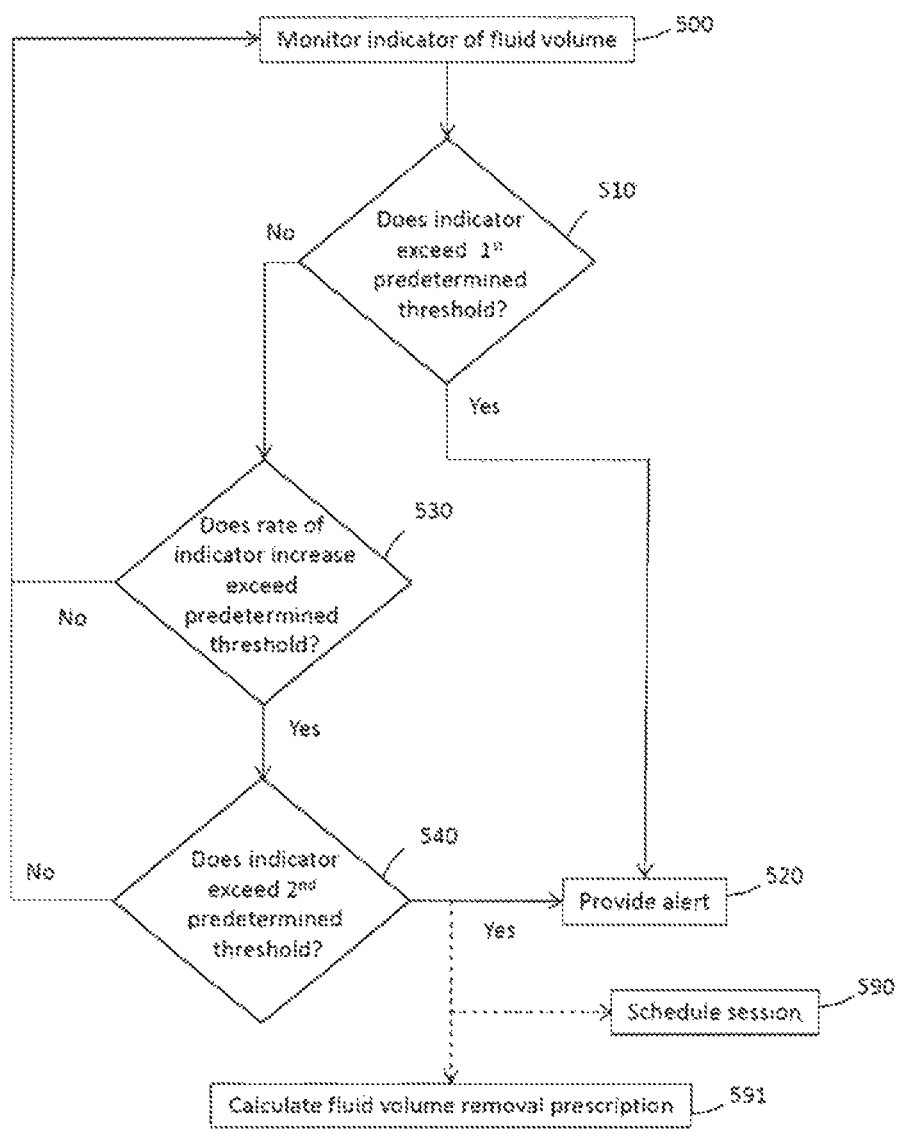

In additional embodiments, a decision to provide an alert or to modify a rate of fluid removal or addition of replacement fluid can be made through the monitoring of only one of the tissue fluid volume or the blood fluid volume. Referring to FIGS. 22-24, overviews of embodiments of methods for monitoring of fluid volume of one of the tissue compartment and the blood compartment are presented. In some embodiments, the methods can be used for purposes of assisting in determining the appropriate timing of a creation of a fistula. For example, an indicator of fluid volume (e.g., as discussed above) can be monitored 500 and a determination may be made as to whether the indicator exceeds a predetermined threshold 510, such as a threshold that is indicative of excess fluid levels that would warrant creation of a fistula. The threshold may be based on empirical data collected over populations of patients based on closely monitored patients in accordance with existing medical practice, may be based on changes from baseline within a given patient, or the like. If the monitored indicator exceeds a threshold indicative of increased fluid, an alert may be provided 520, such as an alert provided by an indicator circuit of a sensor as described above. Data regarding the monitored indicator of fluid volume can be transmitted to a health to a healthcare provider, as described above.

In some embodiments, the methods depicted in FIGS. 22-24 can be used for determining whether a heart failure patient is close to being decompensated. Data regarding fluid levels before or during the patient's prior decompensation events may be marked or evaluated. By way of example, a physician or health care provide may interrogate a fluid monitoring device (e.g. a blood compartment monitor or a tissue compartment monitor) to better understand events that preceded a patient presenting with heart failure decompensation. Thresholds for alerts may be adjusted based on monitored fluid levels, rates, etc. that occurred prior to the patient's decompensated heart failure event. In some embodiments, the monitoring device or system including the monitoring device may receive input regarding the patient's decompensation status, and the device or system may be reviewed data stored in memory to determine whether certain patterns appear in relation to decompensation. Thresholds for issuance of alerts may be adjusted automatically by the device or system.

As shown in FIG. 23, a method may include determining whether the rate of fluid increase, based on the monitored indicator, exceeds a predetermined threshold 530. If the rate of increase of fluid volume is high or exceeds a threshold, the alert (etc.) may be provided. In some embodiments, it may be desirable to determine whether the rate exceeds a threshold 530 prior to determining whether the overall value of the indicator exceeds a threshold 510, because if the rate of increase is high, the overall threshold may be lower than if the rate is low. That is, the threshold 510 may be based on the rate 530.

For example and as shown in FIG. 24, a method may include determining whether the monitored indicator exceeds a first high threshold 510, in which case an alert (etc.) is provided 520. If the indicator does not exceed the first high threshold 510, a determination may be made as to whether the rate of increase of fluid, as indicated by the sensed data, exceeds a threshold 530. If the rate of increase exceeds a threshold, a determination may be made as to whether the value of the monitored indicator (as it is indicative of fluid volume) exceeds a lower second threshold 540. In which case, the alert (etc.) may be provided 520. In this way, a lower threshold may be set if the rate of increase is high. The threshold values may be entered into lookup tables based on prior data from other patients or populations or may be "learned" based on sensed data acquired within the patient.

It will be understood that the methods depicted in, and described with regard to FIGS. 22-24, may be useful for patients that are already undergoing blood fluid removal treatments, and may be used for purposes of automatically scheduling fluid removal session (e.g., 590, FIG. 24), e.g., via telemetry circuit as described above. A sensor monitoring the indicator of fluid volume may also calculate a fluid volume prescription based on the sensed data (e.g., 591, FIG. 24) and transmit data regarding the prescription to a fluid volume removal device or other device that will allow a healthcare provider to enter the appropriate fluid volume removal prescription. Alternatively or in addition, data regarding the monitored indicator may be sent to a fluid volume removal device or other device, which may then calculate an appropriate fluid volume removal prescription (e.g., 591, FIG. 24) based on the transmitted data. The fluid volume prescription data calculated by the sensor device or other device may be based on prior data from other patients or populations or may be "learned" based on sensed data acquired within the patient over time.

Adjustment of Dialysate Composition

As described above, the potassium ion concentrate of a dialysate fluid can be adjusted to adjust potassium ion concentration to obtained better control over the rate of potassium ion removal from the patient, as fully described above. However, additional adjustments to electrolytes contained in a dialysate fluid and/or pH or buffer composition of the dialysate. Accordingly, one goal of hemodialysis, ultrafiltration, and the like is to ensure that the patient's blood pH and electrolyte concentrations are within acceptable ranges. Typical ranges of pH and blood electrolyte concentration that are desired during or following a blood fluid removal session are provided in Table 4 below. Target concentrations of various buffers and electrolytes (or salts or hydrates thereof) are presented on Table 4.

TABLE 4

Typical target ranges for pH and electrolytes
(ref. Medical Surgical Nursing, 7th Ed., 2007)

|  | Target Range |
|---|---|
| pH | 7.35-7.45 |
| Phosphate | 2.8-4.5 mg/dL |
| Bicarbonate | 22-26 mEq/L |
| $Cl^-$ | 96-106 mEq/L |
| $Mg^{2+}$ | 1.5-2.5 mEq/L |
| $Na^+$ | 135-145 mEq/L |
| $K^+$ | 3.5-5.0 mEq/L |
| $Ca^{2+}$ | 4.5-5.5 mEq/L |

Figure 25:
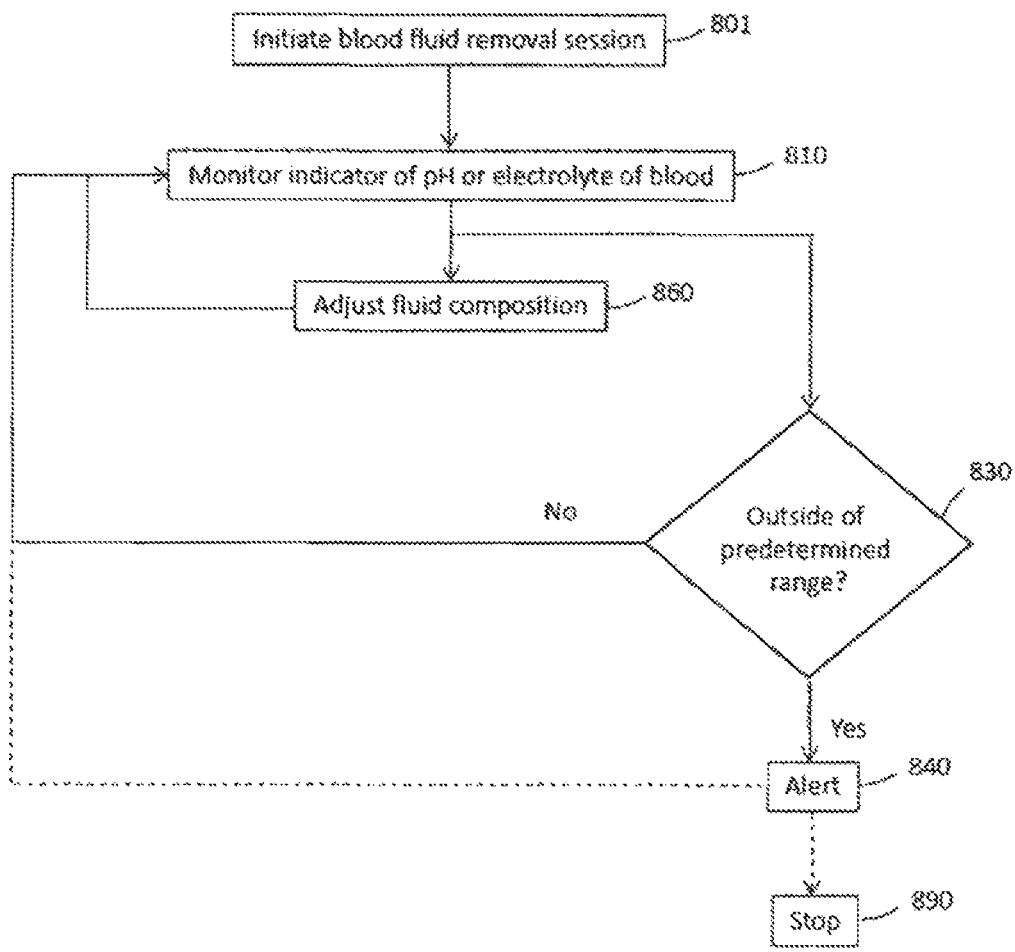
FIGS. 25-27 are flow diagrams depicting overviews of methods in accordance with certain embodiments described herein.

As described above, the composition of the dialysate traveling to the hemodialysis unit 15 can be adjusted by infusion set 35 and monitored by one or more sensors 74, 75, and 76. Further, one or more sensors for detecting electrolytes (e.g. $Ca^{2+}$, $Mg^{2+}$, $Na^+$, $Cl^-$) or monitoring electrolytes in the blood circuit 10. In certain embodiments, such sensor can be placed upstream of the hemodialysis unit 15 to measure the composition of blood under the hemodialysis unit 15 and downstream of the hemodialysis unit 15 to measure blood exiting the hemodialysis unit 15, wherein adjustment to the dialysate fluid can be made based upon a difference in signal between the upstream and downstream sensors. Referring now to FIG. 25, the depicted method includes initiating a blood fluid removal session 801 and monitoring an indicator pH or electrolyte concentration of blood 810; e.g. detecting pH or electrolytes in blood or in fluid from which pH or electrolyte levels in blood can be derived. Based on the monitored indicator of pH or electrolytes, the pH or electrolyte composition or concentration of fluid (e.g., dialysate or replacement fluid) used in the blood fluid removal session can be adjusted 860. For example, based on one or more of the current value of a monitored ionic species or the rate of change in the monitored ionic species, the fluid composition can be adjusted, e.g. as discussed above.

As shown in FIG. 25, continuous, periodic or intermittent determinations can be made as to whether the pH or electrolyte concentration is out of range 830 based on data acquired during the monitoring 810. For example, a determination 830 may be made as to whether pH or electrolyte levels crossed a threshold (e.g., a ceiling or floor). If the pH or electrolytes are determined to be within range, monitoring 810 can continue. If the pH or electrolytes are determined to be out of range (e.g., cross a threshold), an alert 840 can be issued to notify the patient or a healthcare provider of the situation. In some cases, the situation may warrant stopping 890 of the blood fluid removal session; e.g., if the detected pH or electrolytes are too far out of range or cross a heightened threshold. In other cases, it may be suitable to continue with the blood fluid removal session with heightened awareness of a situation for which increased attention may be warranted.

Figure 26:
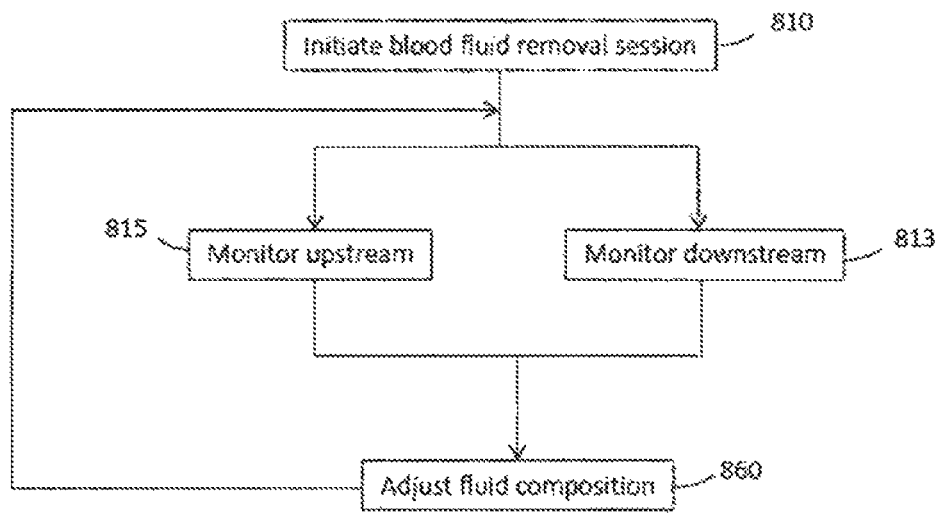

Referring now to FIG. 26, the depicted method includes initiating a blood fluid removal session 801 and monitoring an indicator pH or electrolyte concentration upstream 815 and downstream 813 of the hemodialysis unit 15. Data acquired from upstream and downstream sensors can be compared to determine how to adjust 860 the fluid composition, e.g. as described above.

Figure 27:
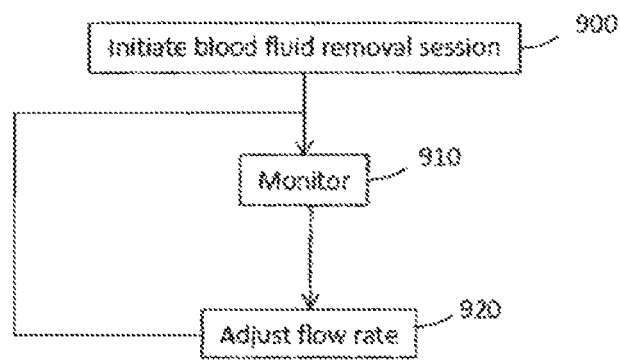

Referring now to FIG. 27, a method where blood electrolyte concentration or pH is adjusted by altering the flow rate of dialysate or blood is shown. The method includes initiating a blood fluid removal session 900, such as a hemodialysis session, and monitoring an indicator of pH or electrolyte 910, which can be in the patient, upstream of the device, downstream of the device, within the device, or the like. Based on the monitored data 910, adjustments to the flow of dialysate or blood may be made 920 to adjust the electrolyte concentration or pH in the blood that gets returned to the patient.

In additional embodiments, the composition of a dialysate can be changed or adjusted based on one or more cardiovascular (CV) parameters that can be monitored during a dialysis treatment session. A suitable external or implantable device can be used to measure certain CV parameters such as blood pressure (BP), heart rate and electrocardiogram (ECG) signals. One suitable implantable sensor device configured to monitor a patient's ECG signals is Medtronic, Inc.'s Reveal® series cardiac monitors. In some embodiments, a sensor device for measuring one or more CV parameters can be a suitably equipped pacemaker or defibrillator implanted in the patient. Monitored cardiac signals from such implanted devices can be transmitted to a dialysis device or other computing device for setting dialysis session parameters using the communication systems described herein. In further embodiments, suitable external ECG monitors, heart monitors and blood pressure sensing devices can be used to measure the one or more CV parameters. For example, a Holter sensor system can be configured to monitor ECG activity of the patient. An example of a suitable external blood pressure monitoring system is the wearable blood pressure monitor described in U.S. Pat. No. 7,674,231, "Wearable Pulse Wave Velocity Blood Pressure Sensor and Methods of Calibration Thereof", issued Mar. 9, 2010.

In certain embodiments, the one or more CV parameters can be selected from one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

One or more of the monitored CV parameters may be employed to set an appropriate prescription, such as dialysate composition, for the patient's next dialysis session or to adjust during a dialysis session. By way of example, if the patient's blood pressure is high or higher than typical for the patient, the rate of fluid removal can be increased. If the blood pressure is low or lower than typical for the patient, the rate of fluid removal can be decreased. If the patient's heart rate is high (e.g., higher than a predetermined threshold), the dialysate potassium concentration may be increased. A determination that potassium concentration requires adjustment based on a CV parameters can be performed regardless of any mass transfer of potassium that may be determined by the system.

Table 5 below provides some general examples of how an initial prescription or adjustments during a blood fluid removal session can be altered based on a monitored cardiovascular condition or parameter.

TABLE 5

Example alterations that may be taken based on cardiovascular monitoring

| Monitored Parameter | Status | Fluid Removal Rate | $K^+$ conc. | $Na^+$ conc. |
|---|---|---|---|---|
| Blood pressure | High | Increase | | Decrease |
| | Low | Decrease | | Increase |
| Heart rate | High | | Increase | |
| | Low | | Decrease | |
| Q-T interval | High | | Increase | |
| | Low | | Decrease | |

Monitoring of the one or more cardiovascular parameters can occur before, during or after a dialysis session where a dialysis treatment parameter, such as dialysate composition, is changed. If the patient's cardiovascular conditions continue to worsen following an adjustment, the dialysis session change cam be reversed or a different change can be made. If the patient's cardiovascular condition improves following the dialysis session parameter change, the parameter change can remain in effect for a period of time or other changes can be made to determine whether further improvements are achievable. The blood fluid removal parameters can be changed one at a time, or more than one at a time can be changed based on patient safety concerns or patient history. For example, if the patient has previously presented with a particular status of a particular condition or combination of conditions and has previously responded favorably to certain combinations of dialysis session parameter adjustments, it be desirable to simultaneously implement such adjustments. Systems and methods for basing parameters on patient history before, during or after a dialysis session are described in Provisional Patent Application No. 61/480,539, and U.S. patent application Ser. No. 13/424,533, filed Mar. 20, 2012, now U.S. 2012/0277722A1 published on Nov. 1, 2012, both entitled ADAPTIVE SYSTEM FOR BLOOD FLUID REMOVAL, filed Apr. 29, 2011, which applications are hereby incorporated herein by reference in their entirety.

Figure 28:
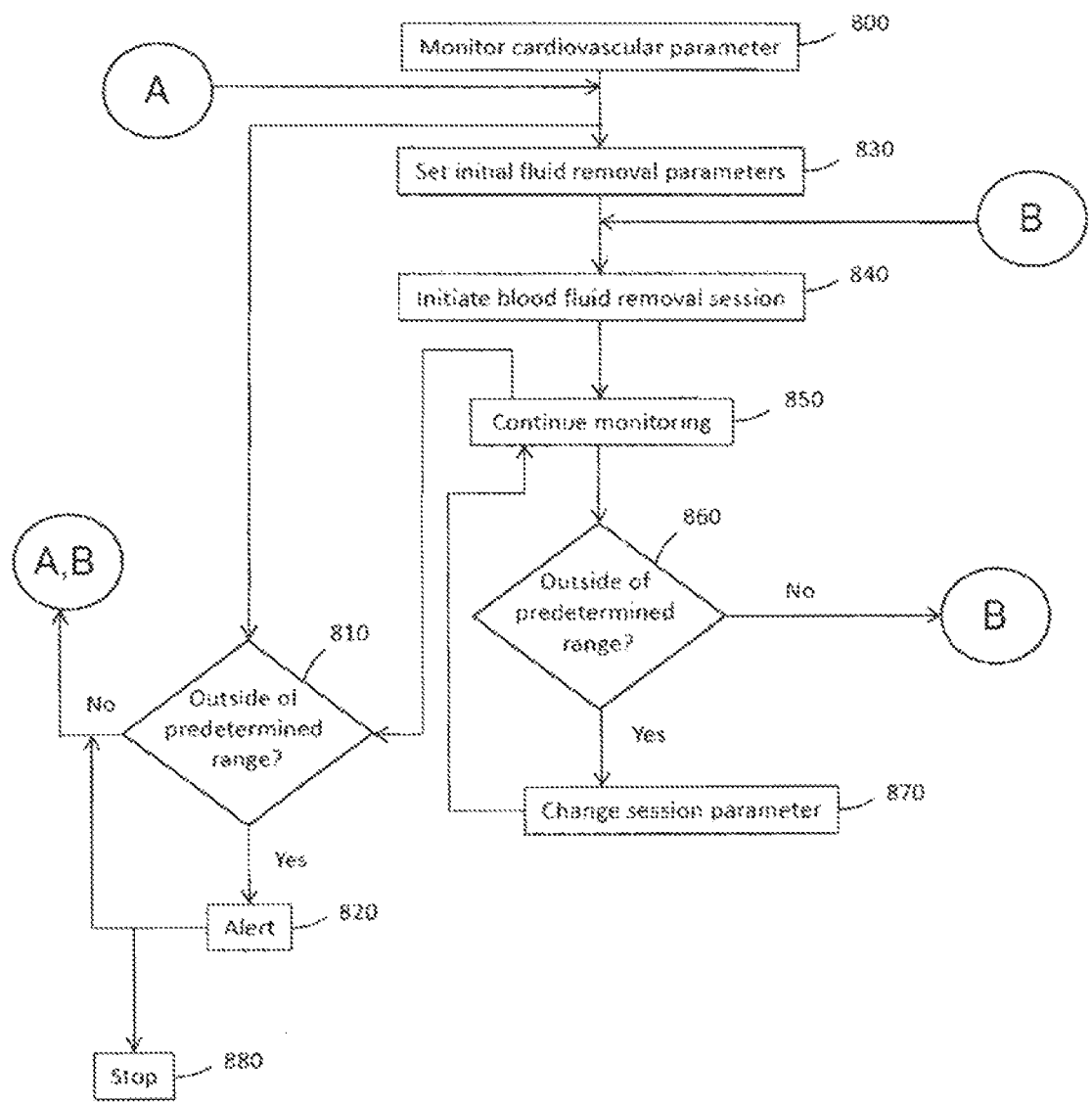
FIGS. 28-29 are flow diagrams depicting overviews of methods in accordance with certain embodiments described herein.

Referring now to FIG. 28, the depicted method includes monitoring a cardiovascular parameter of the patient 800, as discussed above. The monitoring 800 can be chronic or periodic and can employ one or more implantable or wearable sensors. The method further includes determining whether the monitored cardiovascular parameter is outside of a predetermined range 810. If the parameter is determined to be outside of the predetermined range, an alert may be issued 820. The alert can be an alert to the patient, such as a vibration or audible alarm emitted from the sensor or a device in communication with the sensor. The alert can be to a healthcare provider communicated through any of the communication systems described herein.

If the monitored cardiovascular parameter is determined not to be outside the range, data acquired during monitoring 800 is used to set initial parameters of a blood fluid removal session are set 830. The initial parameters of the session can include blood fluid removal rate, profile, or amount, the composition and concentration of components of fluid used during the session, such as dialysate or replacement fluid, and the like. As described above, the ability to chronically cardiac parameters of the patient provides the ability to tailor the parameters of a blood fluid session prior to each session, as opposed to current standard practice in which the fluid composition is adjusted on a monthly basis (or thereabout). As multiple blood fluid removal sessions (e.g., two to three a week) may occur with a month, setting the session parameters on a monthly basis may result in the patient undergoing several blood fluid removal sessions with session parameters that may no longer be well suited for the patient.

Still referring to FIG. 28, once the initial session parameters are set 830, the blood fluid removal session an be initiated 840 and monitoring of the cardiovascular parameters continued 850. A determination may be made as to whether the monitored cardiovascular parameter is outside of a first, higher threshold range 810 or a second, lower threshold range 860. If the parameter is outside of the first range 810, an alert 820 may be provided (e.g., as discussed above) and, in some cases, the blood fluid removal session may be stopped 880. If the cardiovascular parameter is not outside of the first range 810 but is outside the second range (860), a parameter of the dialysis session may be changed 870 based on the monitored cardiovascular parameter (e.g., as discussed above). Further changes may be made in a similar manner as needed.

If the cardiovascular parameter is not outside of the first range 810 or the second range 860, the blood fluid session may continue with the initially set parameters.

Figure 29:
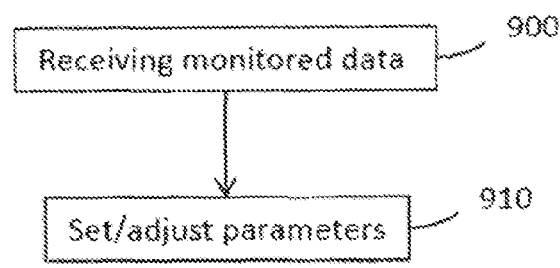

Referring now to FIG. 29 a method carried out by a blood fluid removal or dialysis system or device is shown. The method includes receiving data regarding a monitored cardiovascular parameter 900 and setting or adjusting a parameter of a blood fluid removal session based on the received data. The system or device has control electronics configured to set or adjust the session parameter based on the received data regarding the cardiovascular parameter.

Detection of Membrane Fouling

In certain embodiments, a controlled compliance dialysate circuit 20 is a controlled compliance dialysis circuit as discussed above. In such a dialysate circuit, the flow of fluid between the blood circuit 10 and the dialysate circuit 20 can be controlled through the adjustment of pump rates since the amount of dialysate fluid in the dialysate circuit 20 is a limited or known volume. As such, a change in pressure measured by any of the pressure sensors described above can provide an indication of fouling of a membrane within the hemodialysis unit 15. That is, a fouled membrane will cause excessive high or low pressure in parts of the system during ultrafiltration if the membrane is fouled in a manner that impedes fluid flow across the membrane. However, in some embodiments, a controlled compliance dialysate circuit may not be employed, where the amount of fluid within the dialysate circuit can fluctuate during operation. In such embodiments, the system can nevertheless still be monitored to evaluate the performance of the membrane within the hemodialysis unit 15.

In additional embodiments, the membrane within the hemodialysis unit 15 can be monitored for efficiency in passing dissolved solutes (e.g., urea, electrolytes, etc.) regardless of whether the membrane is further used for ultrafiltration and bulk fluid passage. Such monitoring can be employed for a dialysate circuit 20 that is a controlled compliance circuit.

In certain embodiments, a sensor is configured to monitor an indicator of fluid flow rate. The sensor can employ any suitable flow meter, such as an acoustic Doppler velocimeter, an optical flow meter, a thermal flow meter, a Venturi meter, in-fluid paddle type meter, or the like. In some embodiments, a pressure sensor is used and the flow is calculated based on the pressure and the known diameter of the tubing through which the fluid flows. Such flow meters and components thereof are known in the art and can be readily adapted for use herein.

In certain embodiments, one or more pressure sensors are used to measure differential pressure across a dialysis membrane for purposes of monitoring membrane performance. For example, an increased relative pressure upstream of membrane (e.g., fluid entering the hemodialysis unit 15), or portion thereof, can indicate decreased performance of the membrane (e.g., fouling). By way of further example, a decreased relative upstream pressure can be indicative of a rip or tear in, for example, a membrane.

In certain embodiments, a sensor is configured to monitor an indicator of a compound in blood or in fluid removed from the blood. The sensors can be configured to monitor components of blood that are configured to be removed during hemodialysis. Examples of such compounds include urea, creatinine, sulfate, phosphate, β-2-microglobulin, or the like. Sensors capable of measuring such compounds are known in the art and can be readily adapted for used herein. For example, Nova Biomedical manufactures a variety of sensors capable of detecting components in blood such as creatinine, phosphate, urea and the like, which sensors can be employed or adapted for use herein. Other urea sensor detection technology that may be employed or adapted for used herein is described by Zhong et al., Clin. J. Biotechnol. 1992; 8(1):57-65. β-2-microglobulin sensor detection technology that may be employed or adapted for used herein is described by Brynda et al., Biosens Bioelectron. 1999; 14(4):363-8 and by Nedelkov et al., Proteomics. 2002; 2(4):441-6. Any suitable sensor technology can be employed and the sensor can be placed at any point on the dialysate circuit 20 between the hemodialysis unit 15 and the control pump 102 or other point where fluid is removed or added to the dialysate circuit 20.

In some embodiments, multiple redundant sensors on the same upstream or downstream position relative to the hemodialysis unit 15 can be present on the dialysis circuit 20 to improve accuracy and reliability. In some embodiments, a sensor can have more than one transducer or sensing mechanism to detect more than one compound in blood or to detect a compound in blood and flow rate. In some embodiments, sensors for the same compound may be configured to accurately detect different ranges of concentrations of the compound. In embodiments, more than one transducer is present in a single unit. This allows for convenient data collection and circuitry, as all the data may be collected in one place at the same time.

Figure 30:
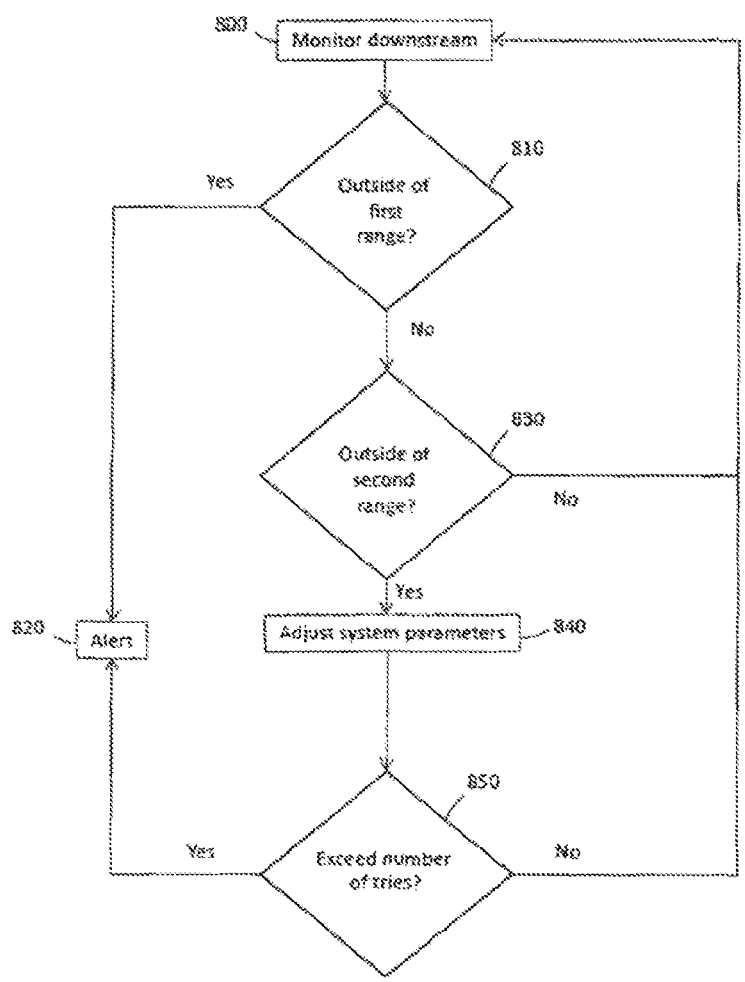
FIGS. 30-34 are flow diagrams depicting overviews of methods in accordance with certain embodiments described herein.

Referring now to FIG. 30 an example of a method for monitoring the performance of a dialysis membrane for ultrafiltration or hemodialysis unit (i.e. medium) is shown. The method includes monitoring a condition downstream of the membrane 800. The condition can be, for example, flow rate of fluid exiting the hemodialysis unit 15, the concentration of a compound (e.g., waste product) in fluid or blood exiting the hemodialysis unit 15, or the like. The depicted method includes determining whether a value of the monitored condition is outside of a first heightened range. If the value of the monitored parameter is outside of the first range (e.g. upper limit), an alert may be issued 820. If the value is not outside of the first heightened range, a determination as to whether the value of the monitored condition is outside of a second less heightened range 830. If the value is not outside of the second range, monitoring 800 may continue. If the value is determined to be outside the second range (e.g., lower limit), one or more system parameters, such as blood flow rate, dialysate flow rate, negative pressure application, or the like, can be adjusted 840 and monitoring 800 can continue. In some cases, it may be desirable to limit the number of attempts to adjust system parameters 840 to bring the medium performance within a desired range. If a predetermined number of tries is exceeded 850 or set amount of time passes without bring the medium performance within a desired range (i.e., within the second range, 830), an alert can be issued 820.

Figure 31:
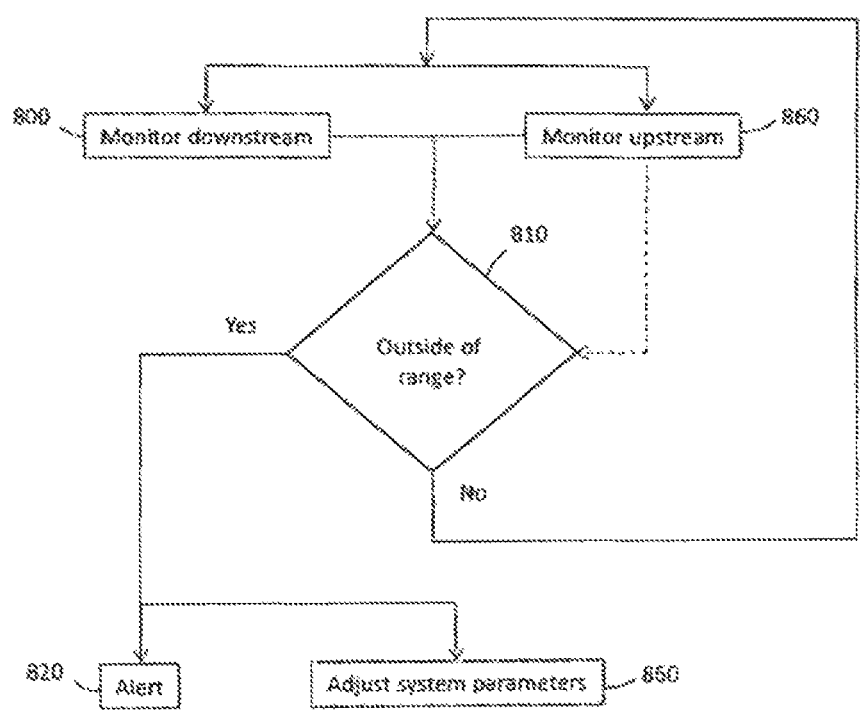

Referring now to FIG. 31 a method for monitoring the performance of a dialysis membrane employing monitoring downstream 800 and upstream 860 of the hemodialysis unit 15 is shown. The upstream monitoring 860 can include monitoring flow rate of blood, pressure, or concentration of a compound, such as a waste product, in blood before the blood enters the medium. A value of the upstream monitoring can be used in determining what constitutes and appropriate range of medium performance 810. In the depicted embodiment, values associated with the upstream 860 and downstream 800 monitoring are compared and a determination is made as to whether the compared values are indicative of the medium performance being out of range 810. If the values are determined not to be indicative of membrane performance being out of range (e.g., fouled, inefficient removal of waste product or fluid, etc.), monitoring 800, 860 can continue (e.g., as discussed above with regard to FIG. 31). If the values are determined to be indicative of medium performance being out of range, an alert can be issued 820.

Figure 32:
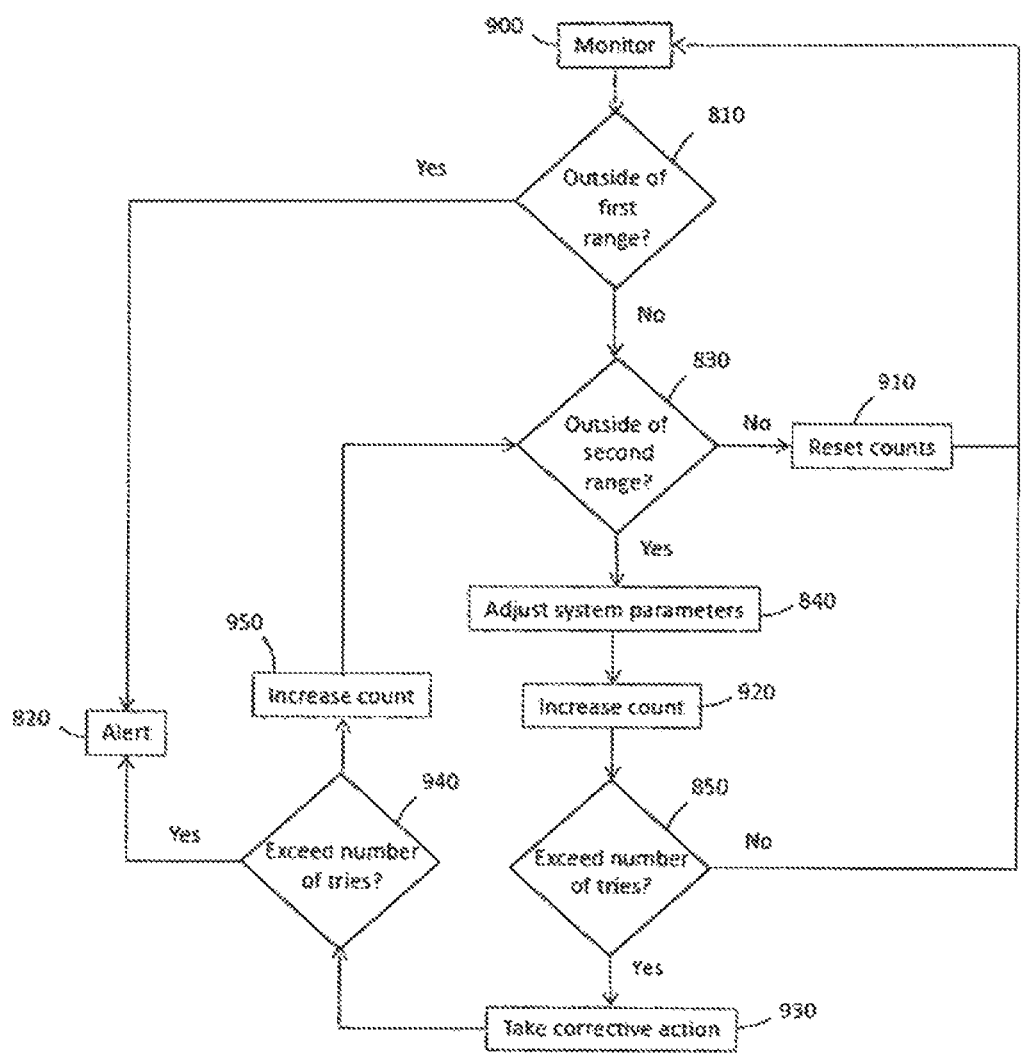

Referring now to FIG. 32, a method is shown that includes maintaining or returning system parameter values to values within a desired range and taking corrective action if the values do not return to the desired range. Aspects of these methods may be performed independently if desired. In the depicted embodiment, a system parameter is monitored 900. The monitoring can be upstream of the hemodialysis unit 15, downstream of the hemodialysis unit 15, or within the hemodialysis unit 15. If a value of the monitored parameter is outside of a first range 810, which may be indicative of more serious system inefficiency or malfunction, an alert 820 can be issued. If the value of the system parameter is determined not to be outside of the first range 810, a determination can be made as to whether the parameter is outside of a second range 830, which may be indicative of a less serious inefficiency or malfunction. If the value is not outside of the second range (i.e., the system is performing as expected), counts 910 can be reset, and monitoring 900 can continue. Additional detail regarding resetting counts 910, which refers to adjustment to system parameters so that monitored values will fall within desired ranges and correcting a cause or source of system inefficiencies or malfunctions, will be discussed below.

If the monitored value is determined to be outside of the second range 830, a modification or adjustment system parameters 840 may be made to return system performance to desired levels (e.g., monitored values fall within second range), e.g., as discussed above with regard to FIG. 30. Before or after adjusting the system parameters 840, a count of the number of corrective attempts or adjustment made can be increased 920. Alternatively or in addition, a timer can be started. A determination can then be made as to whether the number of attempts or time has been exceeded 850. If the number of tries has been exceeded, corrective action can be taken 930 in an attempt to address a cause or source of the malfunction. By way of example, actions may be taken to de-foul or clean a membrane. Examples of how this may be done are presented below with regard to FIG. 32. A determination can be made as to whether a preset number of tries (or time) to address a cause or source of the system inefficiency or malfunction has been attempted 940. If the number of tries has been exceeded, an alert may be issued 820. The count of the number of tries 950 can be increased at any point after taking corrective action 930. If the count or time does not exceed the preset count or time, a determination can be made as to whether the corrective action resulted in the monitored values returning to within the second range 900. If yes, the counts (i.e., counts 920 and 950) can be reset.

Figure 33:
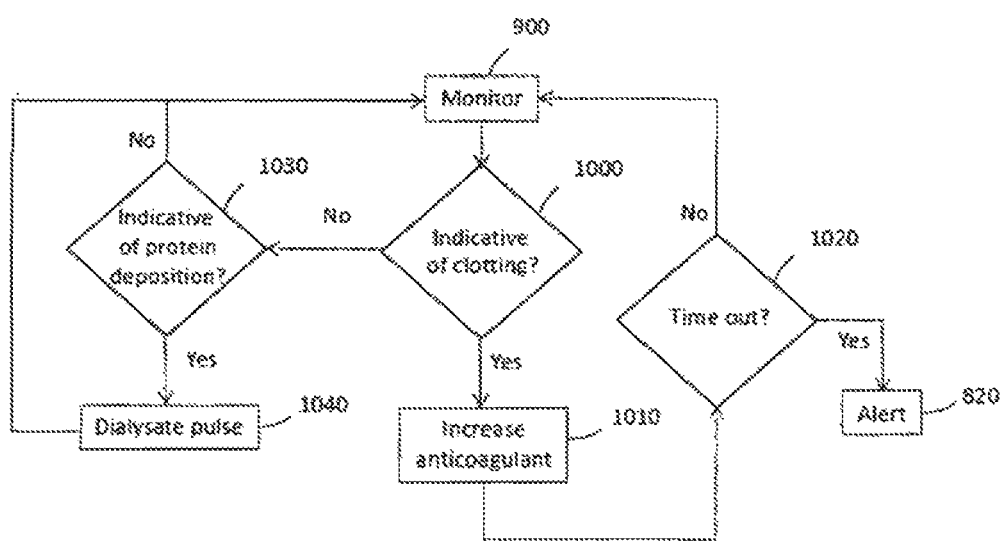

Referring now to FIG. 33 an example of a method for detecting an under-performing membrane and for cleaning or de-fouling the membrane or medium is shown. Severity of fouling of a membrane or medium in contact with blood is most often due to depositing of proteins or clotting factors on the medium, which can lead to blood clotting on medium. During initial protein deposition, medium performance should not be significantly compromised. However, as more protein deposits or initial clotting develops, the performance of the medium will further deteriorate until significant clotting or protein deposition renders the medium ineffective.

FIG. 33 depicts a method in which the medium includes a membrane and the system employs dialysate, such as with a hemodialysis system. However, it will be understood that similar methods may be employed in other types of systems and other types of media; e.g. sorbents. As indicated in FIG. 33, membrane performance can be monitored 900; e.g. as discussed above with regard to pressure differential, flow rates, concentration of chemical species, etc. A determination may be made as to whether a monitored value is indicative of clotting 1000; e.g., a high level of membrane inefficiency. If yes, an increase in anticoagulant agent can be added to the blood or dialysate 1010 in an attempt to prevent further clot formation or a thrombolytic agent may be added to dissolve the clot. A pump or other suitable means for adding an anticoagulant can be placed at any appropriate location on the blood circuit 10 between the blood access point 5 and the hemodialysis unit 15. As discussed above, it may be desirable to stop blood flow or divert blood flow during times thrombolytic agents are being employed. If the monitored value remains indicative of clotting after a predetermined amount of time 1020 after administration of increased concentrations of anticoagulant or thrombolytic agent (or after sequential increases in anticoagulant reach a predetermined upper limit), an alert may be issued 820. If, however, the monitored value is not indicative of clotting, a determination may be made as to whether the monitored value is indicative of a predetermined degree of protein deposition 1030, and a pulse of dialysate 1040, sustained increased dialysate flow or the like, may be delivered in an attempt to clear the deposited proteins from the membrane, and the process repeated.

It will be understood that the order of the steps in FIG. 33 are shown only for purposes of illustration and that the method may be performed in any other suitable order (e.g., step 1030 may be performed before step 1000). Media, such as membranes, or systems may be readily calibrated by one of skill in the art such that changes in monitored values can be attributed to certain degrees of fouling.

Figure 34:
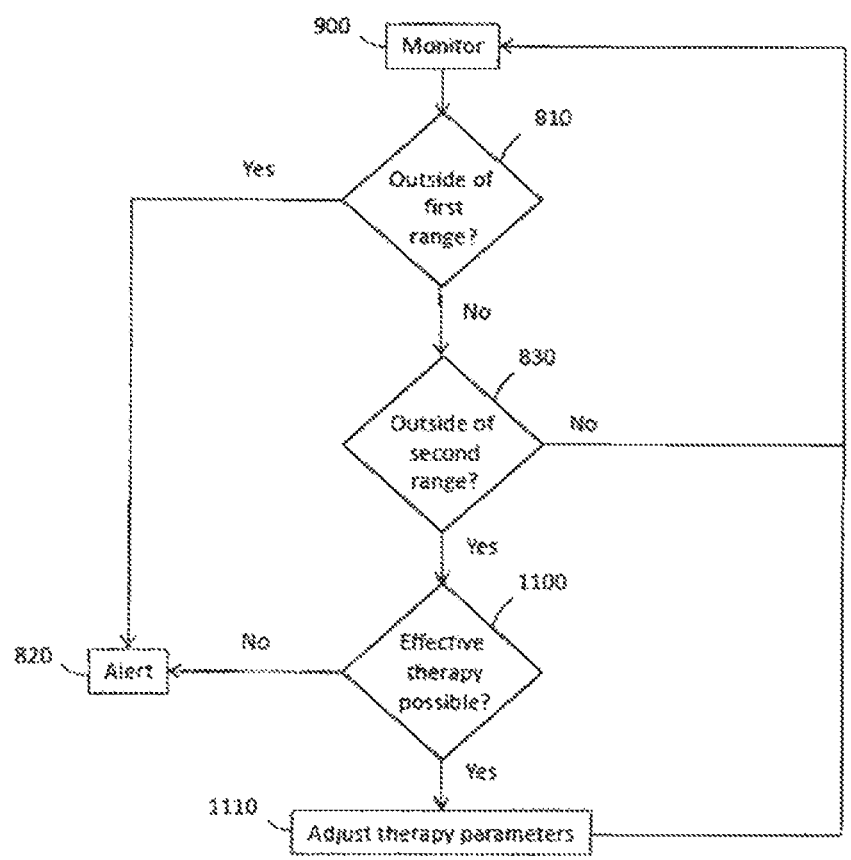

Referring now to FIG. 34 a method is depicted in which therapy proceeds despite monitored parameters indicating poor system performance. In the depicted embodiment, a system parameter is monitored 900. The monitoring may be upstream of the medium, downstream of the medium, or within the medium or medium chamber. If a value of the monitored parameter is outside of a first range 810, which may be indicative of more serious system inefficiency or malfunction, an alert 820 may be issued. If the value of the system parameter is determined not to be outside of the first range 810, a determination may be made as to whether the parameter is outside of a second range 830, which may be indicative of a less serious inefficiency or malfunction. If the value is not outside of the second range (i.e., the system is performing as expected) monitoring 900 and therapy may continue. If, however, the value is outside of the second range 830, a determination may be made as to whether effective therapy may be delivered 1100 despite the poor system performance (as measured by the monitored parameter). For example, it may be determined that the medium is not performing efficiently (e.g., slow rate of waste product or fluid removal from blood), but that an extended session time may be acceptable for achieving therapeutic goals. The therapy parameters may be adjusted 1110; e.g., extend session time, and the process continued.

Automated Updating of Dialysis Parameters

In various embodiments described herein, a method includes (i) initiating a blood fluid removal or dialysis session, which may herein be referred to as a blood fluid removal session, with initial system parameters; (ii) acquiring a first set of data regarding one or more patient physiological parameters; (iii) storing the first data set in a "best" or "most effective to date" data set memory; (iv) associating the initial system parameters in an increased effectiveness lookup table with the first data set; (v) adjusting at least one parameter of the blood fluid removal session to arrive at adjusted system parameters; (vi) acquiring a second set of data regarding the one or more patient physiological parameters after the at least one parameter of the blood fluid removal session has been adjusted; and (vii) if at least one value of the second data set is closer to the target value than a corresponding value of at least one value of the first data set: replacing the first data set in the most effective to date data set memory with the second data set; storing in the increased effectiveness lookup table data regarding the second data set; and associating data regarding the adjusted system parameters with the second data set.

Figure 35:
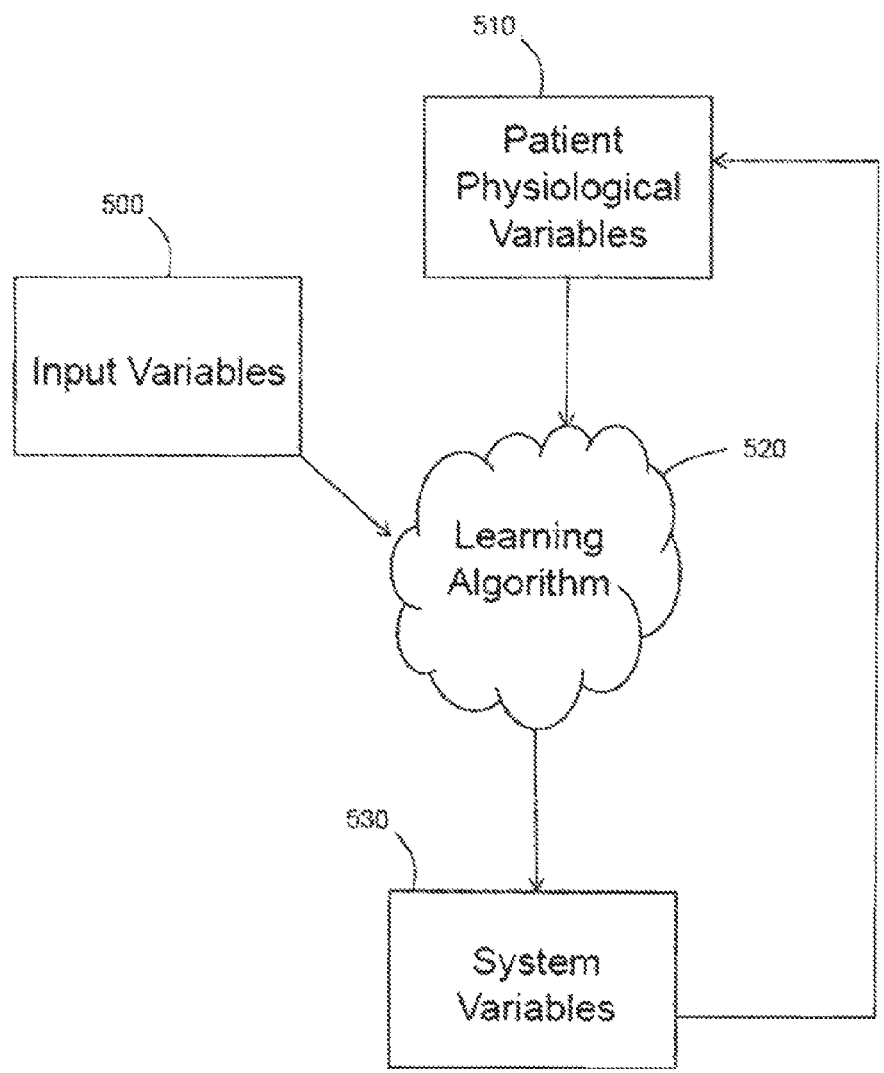
FIGS. 35-41 are flow diagrams illustrating methods in accordance with various embodiments described herein.

As shown in FIG. 35 a algorithm 520, based on input variables 500, and patient physiological variables 510 can determine appropriate system variables 530 to employ based on the patient's history with blood fluid sessions under the algorithm. During a blood fluid session, system variables 530 may be changed and the patient physiological response may be monitored in response to the changed system variables. If one or more of the patient's physiological variables 510 improve or become "more effective", the algorithm 530 can associate the changed system variables 530 with the increased effectiveness patient outcome so that the changed system variables 530 may be used later in the session or in a future session when the patient has a similar set of physiological variables 510. If one or more of the patient's physiological variables 510 become less effective, the algorithm 530 can associate the changed system variables 530 with a less effective patient outcome so that the changed system variables 530 may be avoided later in the session or in a future session when the patient has a similar set of physiological variables 510.

In embodiments, the physiological variables 510 are monitored by sensors that feed data regarding the variables directly into the algorithm 520 or electronics running the algorithm. The sensors may monitor fluid volume in the patient's blood; fluid volume in the patient's tissue; concentrations of electrolytes in the patient's blood; pH of the patient's blood; one or more cardiovascular parameter of the patient, such as blood pressure, heart rhythm, heart rate; or combinations or indicators thereof. The sensors may monitor the patient physiological parameters before, during or after a blood fluid removal session.

Any suitable sensor may be employed. Examples of sensors and systems that may be employed with regard to blood fluid volumes and tissue fluid volumes are discussed in U.S. Provisional Patent Application No. 61/480,528, filed on Apr. 29, 2011, now expired, and U.S. patent application Ser. No. 13/424,454 filed Mar. 20, 2012, now U.S. 2012/0277655A1 published on Nov. 1, 2012, both entitled FLUID VOLUME MONITORING FOR PATIENTS WITH RENAL DISEASE; and U.S. Provisional Patent Application No. 61/480,530, filed on Apr. 29, 2011, now expired, and U.S. patent application Ser. No. 13/424,467 filed Mar. 20, 2012, now U.S. 2012/0277604A1 published on Nov. 1, 2012, both entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well-studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

Examples of sensors and systems for monitoring pH and electrolyte concentration are disclosed in U.S. Provisional Patent Application No. 61/480,532, filed on Apr. 29, 2011, now expired, and U.S. patent application Ser. No. 13/424,479 filed Mar. 20, 2012, now U.S. 2012/0273420A1 published on Nov. 1, 2012, both entitled ELECTROLYTE AND pH MONITORING FOR FLUID REMOVAL PROCESSES, which applications are hereby incorporated herein by reference in their entirety to the extent that they do not conflict with the present disclosure. Of course, any suitable sensor or systems for monitoring pH and electrolyte concentration may be used. For example, a transducer may be employed to detect pH or electrolytes. Suitable transducers may include an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein. One or more sensors may be employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components. A sensor (or transducer) for detecting pH, electrolyte concentration, or the like may be placed at any suitable location for purposes of monitoring electrolytes or pH. For example, the sensor may be implanted in the patient, located external to the patient an upstream of a blood fluid removal device, located external to the patient and downstream of the blood fluid removal device, or the like.

Examples of sensors and systems for monitoring cardiovascular parameters are disclosed in U.S. Provisional Patent Application No. 61/480,535, filed on Apr. 29, 2011, and U.S. patent application Ser. No. 13/424,490 filed Mar. 20, 2012, both entitled CARDIOVASCULAR MONITORING FOR FLUID REMOVAL PROCESSES, which applications are hereby incorporated herein by reference in their entirety to the extent that they do not conflict with the present disclosure. Of course, any suitable sensor for monitoring cardiovascular parameters may be used. In embodiments, pH or electrolyte sensors; e.g., as described above, may be used to monitor cardiovascular parameters. Sensors for monitoring heart rate or heart rhythm may be used. One suitable implantable sensor device that is configured to monitor a patient's ECG signals is a Medtronic, Inc.'s Reveal® series insertable cardiac monitor. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session. Blood pressure monitors, which may be external or implantable (such as Medtronic Inc.'s active leadless pressure sensor (ALPS), which generally takes the form of a stent to anchor the device within a vessel, may be employed. Such a device may be placed in any suitable blood vessel location, such as in a femoral artery or pulmonary artery. A wearable sensor system, such as a Holter sensor system, may be used to monitor ECG activity of the patient. Regardless of whether the sensor or sensor system employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

As indicated above, sensors for monitoring patient physiological parameters may be, or may have components that are, implantable or wearable. In embodiments, multiple sensors may be connected via telemetry, body bus, or the like. The connected sensors may be of the same or different type (e.g., pH or impedance). Such connected sensors may be placed (e.g., internal or external) for purposes of monitoring at various locations of the patient's body.

Monitoring may alternatively or additionally include receiving patient or physician feedback regarding the patient's state. For example, the patient may indicate a point in time when cramping begins, which often happens when too much fluid is removed. The blood fluid monitoring device may include an input, such as a keyboard or touch screen display for entering such data. Alternatively, a separate device such as a patient programmer, laptop computer, tablet computer, personal data assistance, smart phone or the like may be used to input the data; or the like.

Figure 36:
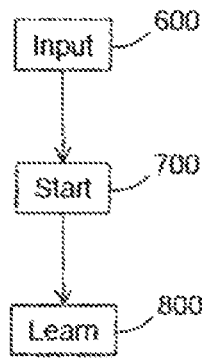

Referring now to FIG. 36 a high level flow diagram of a method is described. The method includes providing input 600, such as input variables discussed above with regard to FIG. 35 to a blood fluid removal system. The method also includes initiating or starting 700 a blood fluid removal session, and learning 800 from the session. The learning 800 may be as discussed above with regard to FIG. 35 with system parameters being varied and patient physiological parameters being monitored to determine which system parameter adjustments result in desirable patient physiologic outcomes.

Figure 37:
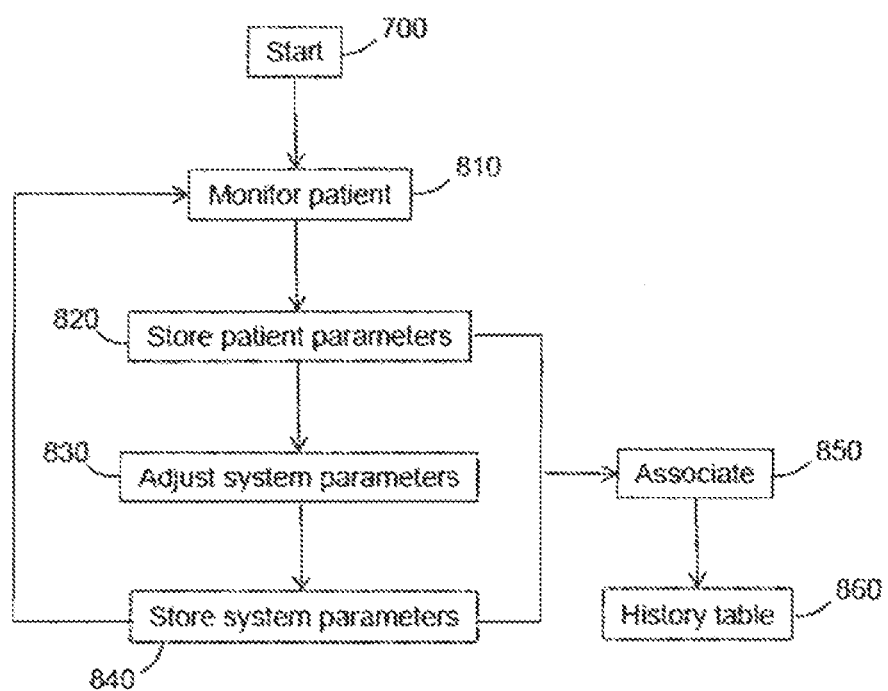

For example and with reference to FIG. 37, additional detail regarding an embodiment of a learning process that may occur during a blood fluid removal session is shown. The blood fluid removal session is started 700 and the patient is monitored 810. Monitored patient parameters, such as patient physiological variables as discussed above, are stored 820; e.g., in memory of the blood fluid removal system. The system parameters, such as system variables described above, which may include rate of fluid removal from the blood or electrolyte concentration of a dialysate or replacement fluid, are adjusted 830 and the system parameters are stored 840; e.g., in memory of the blood fluid removal system, dialysis system or monitoring system, and patient monitoring 810 continues. The set of stored patient parameters 820 are associated 850 with a set of stored system parameters 840 so that the system may recall particular system parameters that were employed at the time the patient had a given set of parameters. The data regarding the stored patient parameters (820) and the stored system parameters 840 may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to changing system parameters (860).

Figure 38:
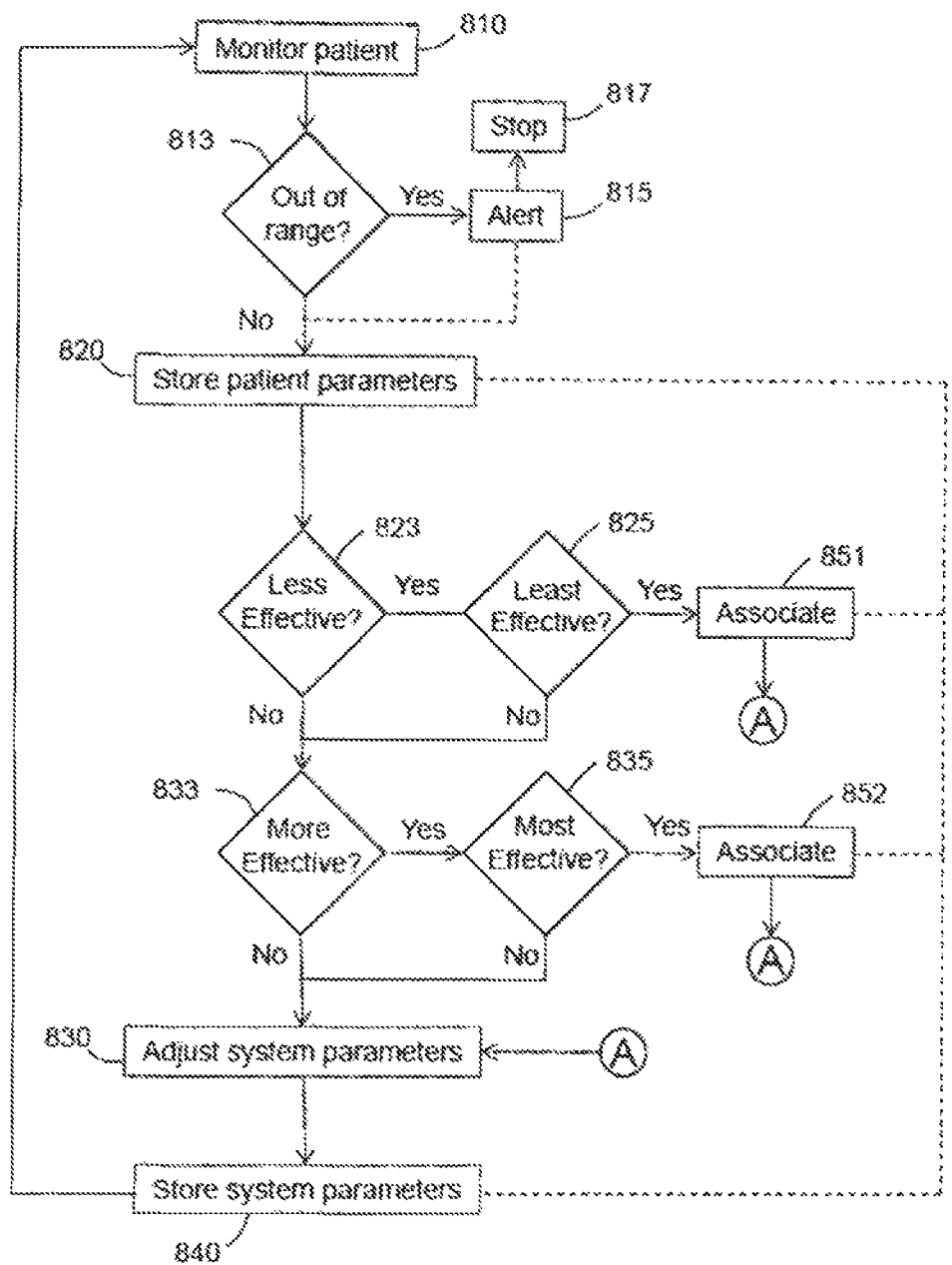

A more detailed embodiment is presented in FIG. 38. In the embodiment depicted in FIG. 38, patient is monitored 810 during a blood fluid removal session. It may be desirable to determine whether data acquired from patient monitoring is out of range 813. As used herein, "out of range" means that a value of a monitored parameter exceeds (i.e., is above or below) a predetermined range of values. The predetermined range of values may be indicative of a patient safety concern. If the data is out of range, an alert may be issued 815 or the session may be stopped 817. In some cases, it may be desirable to continue with the session, even if the monitored data or some aspect thereof is out of range. In the depicted embodiment, if the session is continued, (e.g., due to choice or to the monitored data not being out of range), data regarding the monitored patient parameters is stored 820 and is compared to stored patient data previously obtained (e.g., in a prior session or earlier in the session). A determination may be made as to whether the present patient parameter data is less effective 823 than stored patient parameter data resulting from system parameter adjustments 830 that occurred just prior to the current set of system parameters. If the data is determined to be less effective 823, the stored current patient parameters 820 may be associated 851 with stored current system parameters 840; e.g., as discussed above. In some cases, it may be desirable to determine whether the current patient parameter data, or a portion or aspect thereof, is the least effective that has been detected in the patient in a current or previous blood fluid removal session 825; e.g. by comparing the current patient data to a history of collected patient data. If the current patient data is the least effective observed 825 to date, the stored current patient parameters 820 may be associated 851 with stored current system parameters 840. In this way, only the "least effective" patient conditions are tracked, as opposed to all patient conditions, which can save on memory and processing power. In any case, once the patient and system parameter data is associated 851, the system parameters may be adjusted 830 and the process repeated.

If the present patient parameter data is determined to not be less effective than stored patient parameter data resulting from system parameter adjustments that occurred just prior to the current set of system parameters, a determination may be made as to whether the present patient parameter data is more effective 833 than stored patient parameter data resulting from system parameter adjustments 830 that occurred just prior to the current set of system parameters. If the data is determined to be more effective 833, the stored current patient parameters 820 may be associated 852 with stored current system parameters 840; e.g., as discussed above. In some cases, it may be desirable to determine whether the current patient parameter data, or a portion or aspect thereof, is the most effective that has been detected in the patient in a current or previous blood fluid removal session (835); e.g. by comparing the current patient data to a history of collected patient data (e.g., "history table" in FIG. 37). If the current patient data is the most effective observed 835 to date, the stored current patient parameters 820 may be associated 852 with stored current system parameters 840. In this way, only the "best" or most effective patient conditions are tracked, as opposed to all patient conditions, which can save on memory and processing power. In any case, once the patient and system parameter data is associated 852, the system parameters may be adjusted (830) and the process repeated.

Figure 39:
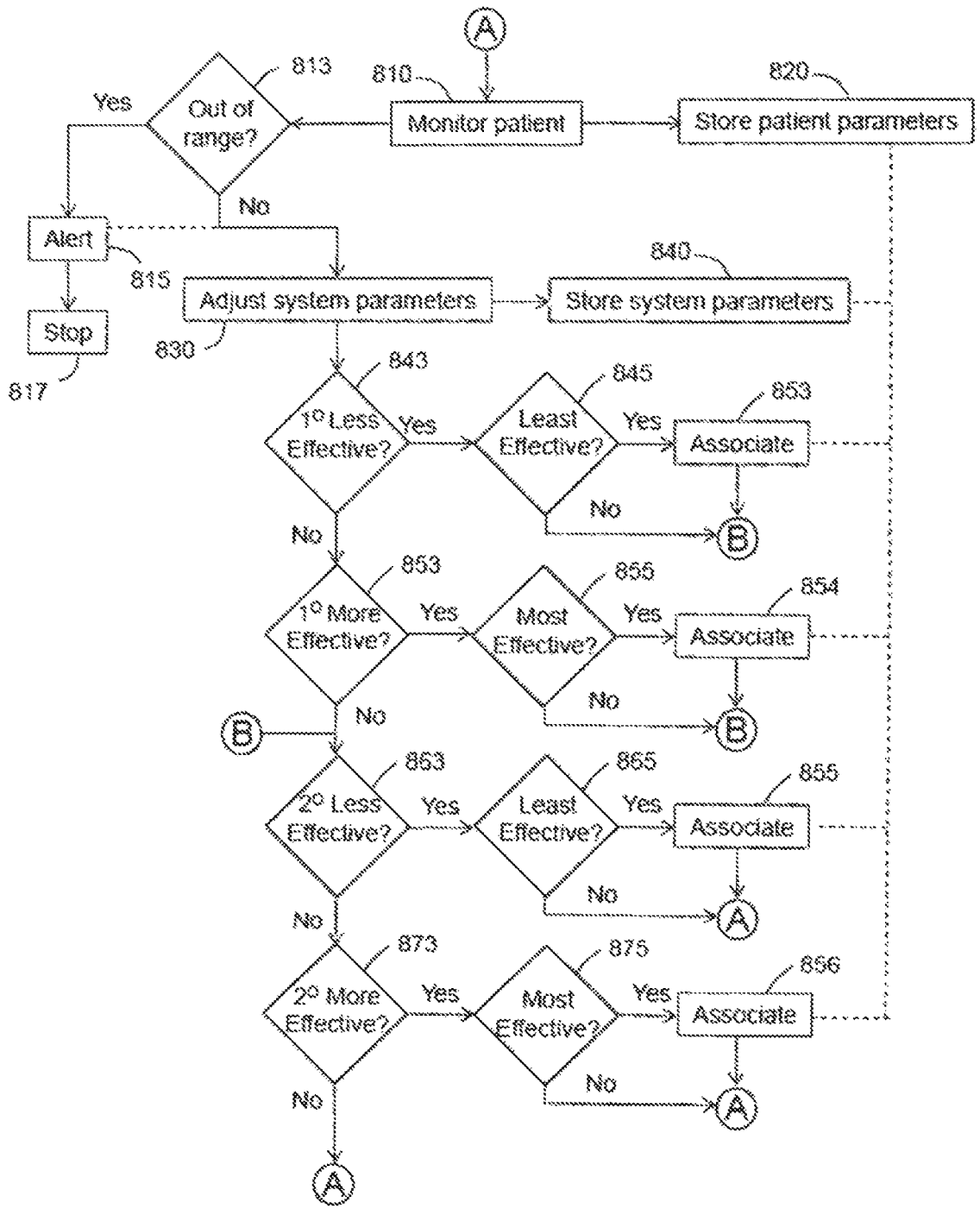
Figure 40:
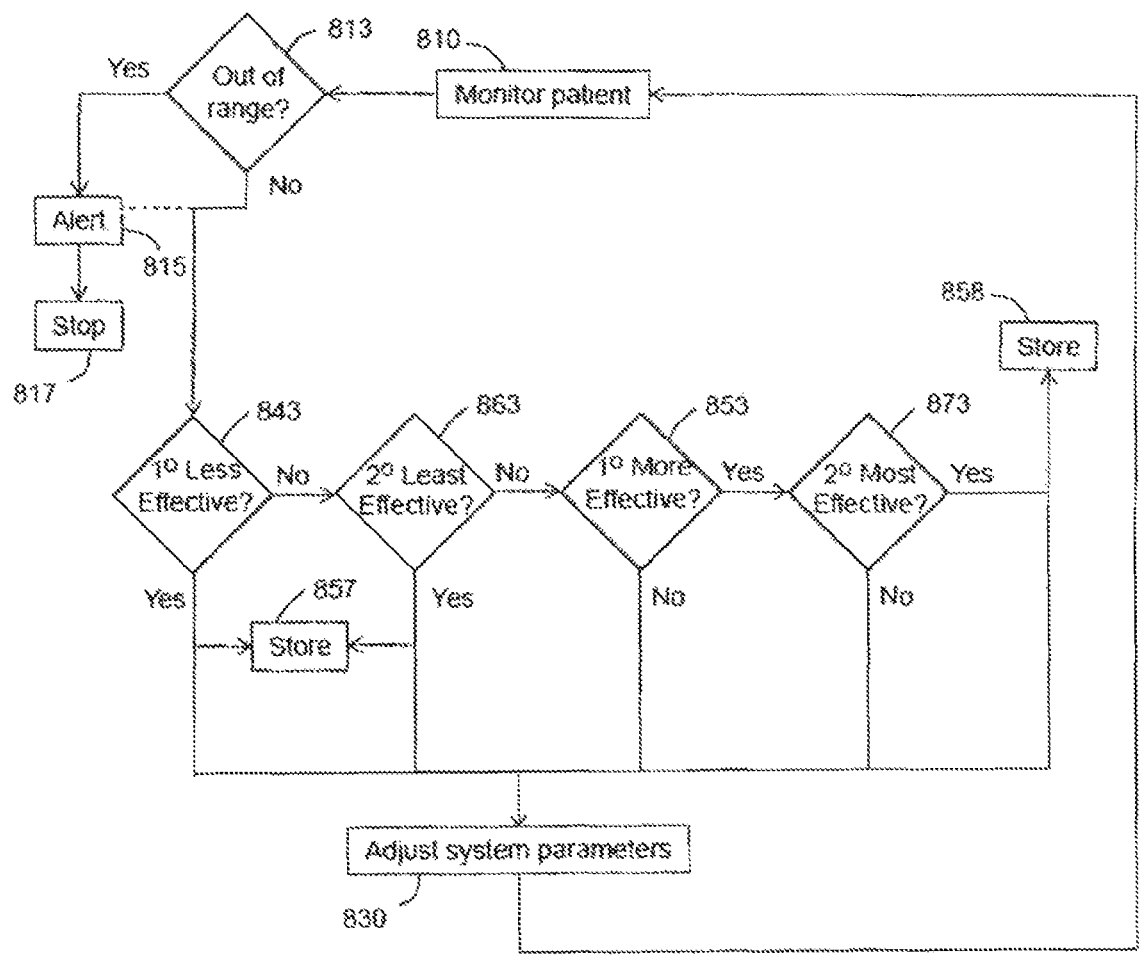

Referring now to FIG. 39, an embodiment of a method where more than one patient parameter variable is evaluated in a manner similar to that described with regard to FIG. 40. In the embodiment depicted in FIG. 39, two patient parameter variables are evaluated. However, it will be understood that any number of patient parameter variables may be evaluated by employing a method as depicted in FIG. 39 or using any other suitable method. In the embodiment depicted in FIG. 39, the variables are labeled "primary" and "secondary", as it may be desirable to prioritize patient parameter variables. For example, in some cases it may be desirable to monitor blood pressure and attempt to achieve a stable blood pressure at or near a target range throughout the session because hypotension is one of the most common side effects of blood fluid removal sessions. That is, as long as other patient parameters are not out of a predetermined range, the system may attempt to keep blood pressure in check and make adjustments to that end. However, in some cases, reducing arrhythmias is the primary goal, as many patients for which a blood fluid removal process is indicated dire from complications due to arrhythmias. If arrhythmias are determined to be the primary patient parameter, the blood fluid removal system may attempt to keep arrhythmias in check and make adjustments to this effect without regard to other patient parameters, e.g., as long as the other patient parameters remain within acceptable limits.

The method depicted in FIG. 39 includes monitoring patient parameters 810 (at least a primary and secondary patient parameter), storing patient parameter data 820, and determining whether a parameter, or aspect thereof, is out of a predetermined range 813. If the parameter is out of range, an alert may be issued 815, the blood fluid removal session may be stopped 817 or the session may continue. If the parameters are determined to not be out of range 813, the system parameters may be adjusted 843 and stored 840. A determination may then be made as to whether the primary patient parameter is less effective 843, e.g. by comparing current patient parameter data to stored patient parameter data resulting from system parameter adjustments that occurred just prior to the current set of system parameters. If the primary patient parameter is determined to be less effective 843, the current stored patient parameter data may be associated 853 with the current stored system parameters. Alternatively or in addition, a determination may be made as to whether the current patient parameter data regarding the primary parameter is the lease effective that has been detected in the patient in a current or previous blood fluid removal session 845; e.g., as discussed above with regard to FIG. 39. If it is the least effective, the current stored patient parameter data may be associated 853 with the current stored system parameters as described above with regard to FIG. 38. Similarly determinations as to whether the primary patent parameter data is more effective 853 or the most effective to date 855 may be made and stored system and patient parameters may be associated 854. Similar determinations regarding whether the secondary patient parameter, or a value associated therewith, is less effective 863, the least effective 865, more effective 873, the most effective 875 and appropriate associations 855, 856 may be made. In this manner, the system may identify and learn how system parameters may affect individually monitored patient parameters, such as blood pressure, heart rate, fluid volume, and electrolyte concentration. Based on this information, the system may make choices as to which system parameters may be employed to produce results that are likely to be favorable to the patient.

Referring now to FIG. 40 a flow diagram depicting a process where the combined response of two or more patient parameters to changes in system parameters 830 is tracked. For the purposes of convenience some of the steps depicted and described above with regard to FIGS. 39-40 are omitted from FIG. 40. However, it will be understood that the same or similar steps may be employed with regard to the method depicted in FIG. 40. In the depicted embodiment, patient parameters and system parameters are stored (857, 858) only when both the primary and secondary patient parameters are determined to become less effective (843, 863) or more effective (853, 873). In this manner, the system may identify or learn which system parameters result in desirable (or undesirable) changes in multiple patient parameters.

Through the association of patient parameter data and system parameter data as shown in FIGS. 37-40 and discussed above, a history of patient responses to changing system parameters may be obtained. This history, which may be in the form of a lookup table, may be consulted prior to or during a blood fluid removal session to determine which system parameters, given the patient's physiological parameters at a given point in time, are more likely to cause the patient to respond favorably and which system parameters are more likely to cause the patient to respond negatively. Accordingly, the system may respond by adjusting parameters to those that are more likely to cause the patient to respond favorably.

Figure 41:
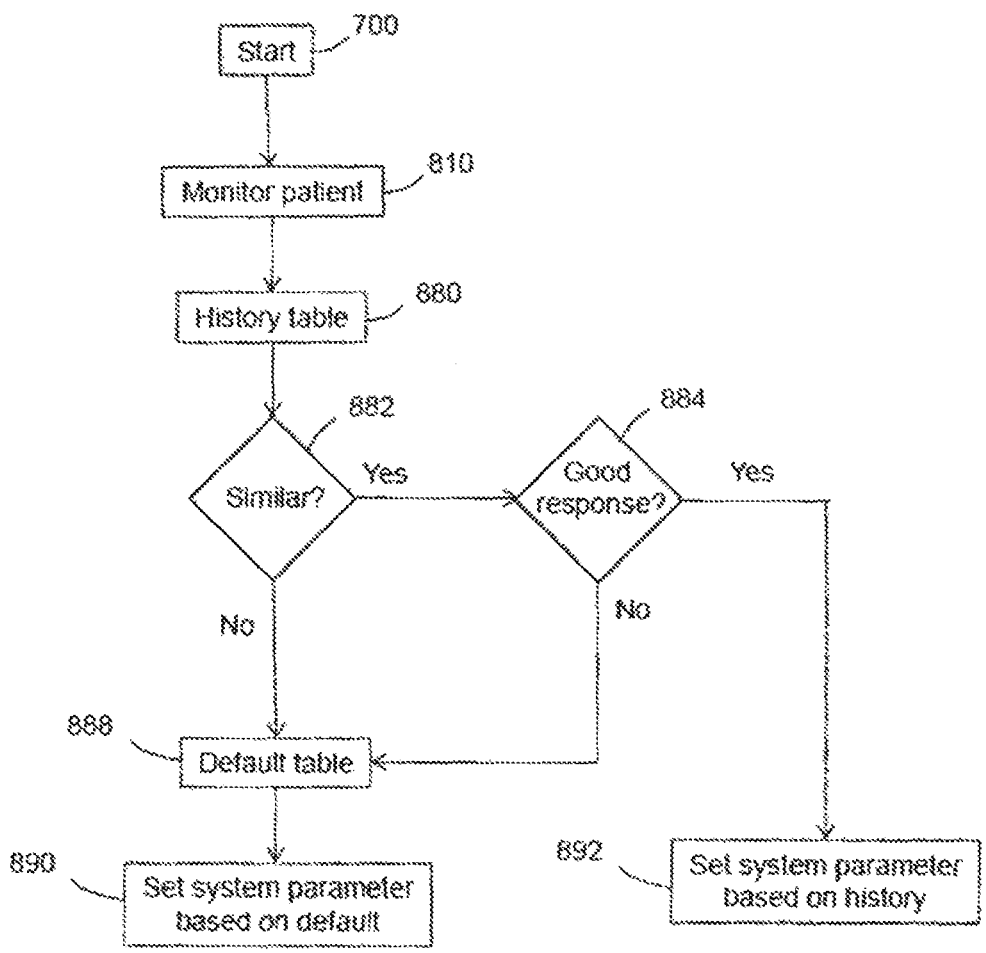

For example and with reference to FIG. 41, a flow diagram is shown that depicts and embodiment of how stored and associated data (e.g., as discussed above with regard to FIGS. 37-40) may be used to determine which system parameters to use at a given time in a blood fluid removal session. The method includes initiating or starting a blood fluid removal session 700, monitoring patient parameters 810, and consulting history lookup table 880, which may be generated by associating system parameters and patient parameters as described above with regard to FIGS. 37-40. A value associated with the current patient parameter data is compared to data regarding a corresponding value in the lookup table, and a determination is made as to whether the current patient parameter is similar to prior patient parameter data stored in the history table 882. By way of example, a value of a current patient parameter data set may be determined to be similar to a corresponding value in the lookup table if the values are within 10%. The system may scroll through the lookup table to identify the closest corresponding value, if more than one corresponding value is within the predetermined cutoff for being considered similar (e.g., within 10%). As used herein, a "corresponding" value is a value of the same parameter obtained at different times. The value may be a magnitude, a rate of change, an average, or the like. The parameter may be blood pressure, heart rate, fluid volume, concentration of electrolyte, or the like.

If more than one parameter or value of a parameter is compared to data in the lookup table, the system may determine whether each value for each parameter is within the predetermined cutoff for being considered similar and identify a prior patient parameter data set as being most similar by prioritizing or weighting parameters or by summing the percent differences between all of the current values and the corresponding values in the lookup table. Regardless of how the system determines whether a current patient parameter data set is similar, or most similar, to a prior patient data set stored in the history table, a determination may be made as to whether the patient's response to the system parameters associated with the stored patient parameter data table was a favorable response 884; e.g., was "better" (or "more effective") or "best" (or "most effective") as discussed above with regard to FIGS. 38-40. If the prior patient response was determined to be a good or "effective" response, the current system parameters may be set according to the parameters stored in the lookup table 892. If the prior patient response was considered to not to be similar 882 or effective 884, a default table may be consulted 888 which contains non-patient specific system parameters that would generally be considered suitable in general circumstances or that would be considered suitable for a patient presenting with the current physiological parameters. The system parameters may then be set according to the parameters stored in the default table 890.

It will be understood that prior patient negative responses (e.g., "less effective", "least effective") may be stored in a lookup table, accessed and used in a similar manner to that described with regard to the "effective" responses in FIG. 41. In some embodiments, separate lookup tables are maintained for "effective" responses (e.g., an "increased effectiveness" data table) and for "ineffective responses" (e.g., a "decreased effectiveness" data table). In some embodiments, the "increased effectiveness" lookup table and the "decreased effectiveness" lookup table are the same data table, which stores patient parameters and associated system parameters that resulted in "more effective", "most effective", "less effective" or "least effective" patient parameters.

Figure 42:
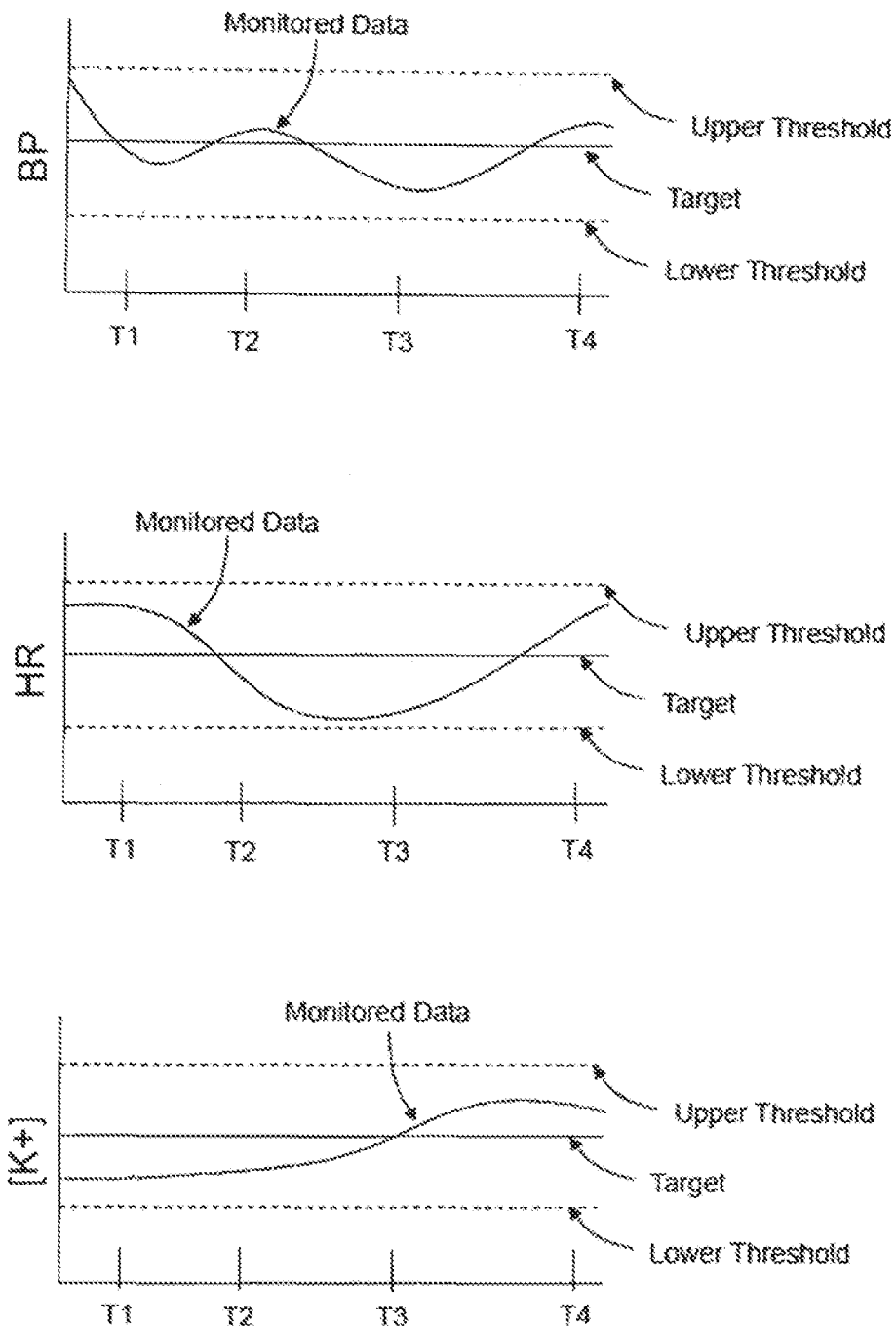
FIG. 42 is a schematic graphical representation of monitored data (not actual data) shown for purposes of illustration.

For purposes of example and to provide some clarity with regard to how one (or a blood fluid removal system) may determine whether patient parameter data is "out of range", "more effective", "less effective", and the like (as discussed above with regard to FIGS. 38-40), graphical schematic data is presented in FIG. 42 showing representations of monitored data (not actual data) for blood pressure (BP), heart rate (HR), and potassium concentration in the patient's blood ($[K^+]$). In the schematic illustration, system parameters are changed at times T1, T2, T3 and T4. The patient parameters (BP, HR, $[K^+]$) are shown as changing in response to the changes in blood fluid removal system parameters. As shown, not all patient parameters will respond similarly (e.g., more effective or less effective) in response to a system parameter change. In the depicted schematic illustrations, a desired target value is shown for each patient parameter. If the monitored data value achieves or approaches the target, a determination may be made that the change in system parameter resulted in an improvement or "more effective" state for that parameter. If the monitored data value deviates from the target, a determination may be made that the change in system parameter resulted in a worsening or "less effective" state for that parameter. It will be understood that the timing of the patient parameter response to a change in system parameters may vary greatly from patient parameter to patient parameter. In some cases, changes in a patient parameter may be observed within seconds or minutes of a change in a system parameter. In other cases, a change in a patient parameter in response to a change in a system parameter may take hours or more to be fully appreciated or observed.

Figure 43:
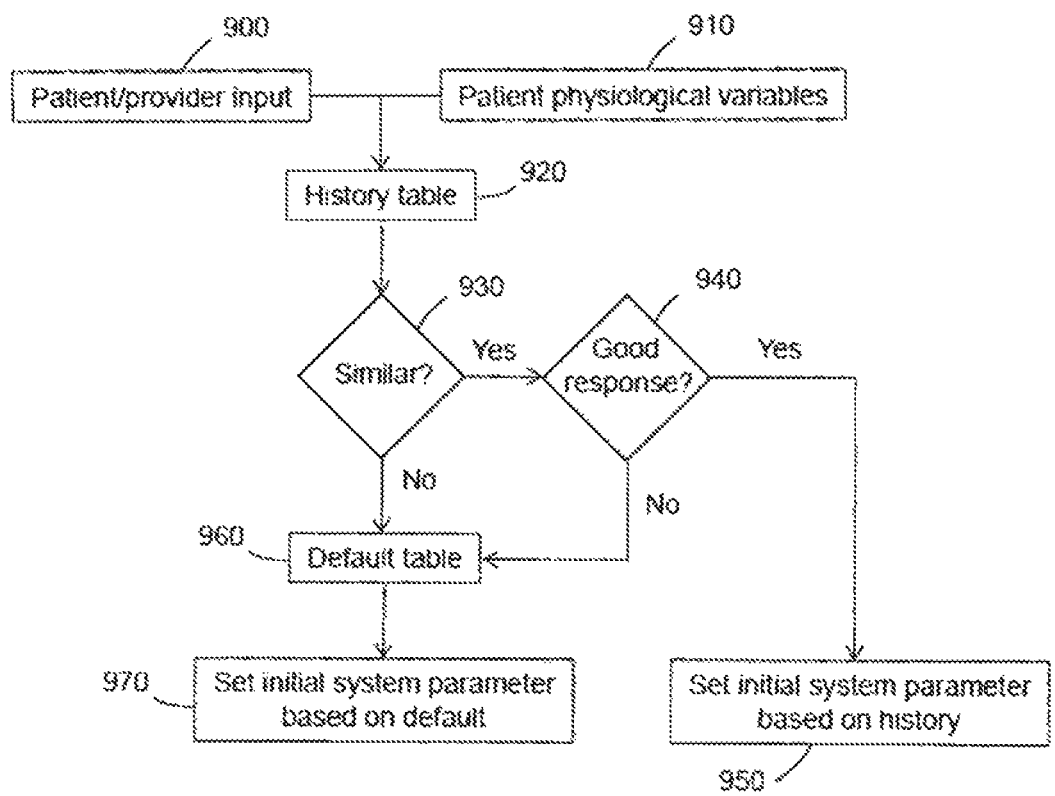
FIG. 43 is a flow diagram illustrating an embodiment of a method described herein.

In the graphical depictions of the represented monitored data presented in FIG. 43, a lower threshold value and an upper threshold value are depicted by horizontal dashed lines. If the monitored data for a patient parameter exceeds the upper threshold value or crosses below the lower threshold value, a determination may be made that the value for that parameter is "out of range."

It will be understood that the condition of a patient may deteriorate with time, which is typical of patients having chronic kidney disease. Accordingly, the targets and upper and lower thresholds may vary with time. These targets and thresholds may be modified by input from, for example, a healthcare provider from time to time based on, e.g., the patient's health or status of patient parameters. Alternatively, the system may automatically adjust target or threshold values over time based on population data or based on data of a particular patient indicative of a generally deteriorating condition. If the target or thresholds are adjusted to or near predetermined cutoff values, an alert may be issued to that effect.

Further, target and threshold values for one or more parameters may be modified on a session-by-session basis. For example, if the patient is excessively fluid overloaded prior to a given session, the target or threshold tissue fluid levels may be adjusted upward for the next or current session. The negative consequences of too much fluid removal in one session or at too fast of a rate may outweigh the negative consequences of higher fluid levels remaining in the patient. Additional or more frequent fluid removal sessions may be employed to return the patient to more desirable fluid levels.

As shown in the examples presented in FIG. 23, the patient parameters change over time. In embodiments, values of one or more patient parameters are averaged over a period of time to account for fluctuations that may occur. The averaged value may be compared to the target and thresholds for determining whether a patient is improving. By averaging values over time, the effect of an anomalous value that may deviate significantly from the target value or may be out of bounds may be diminished. Of course, thresholds may be set for single occurrences, for example if the values of those occurrences may present an imminent health concern to the patient. In embodiments, the presence a single occurrence that deviates significantly from other recent occurrences may result in activation of a subroutine or monitoring method for detecting similar subsequent deviations. In embodiments, consecutive significant deviations, a percent of significant deviations within a given number of samples, or the like, may result in activation or an alert or alarm.

In embodiments, patient parameters are measured or monitored within discrete windows of time rather than continuously. Such time sampling may be valuable for implantable systems or systems having implantable components as the power and processing requirements may be reduced relative to continuous monitoring.

The discussion with regard to FIGS. 37-42 has been primarily directed to blood fluid removal systems and processes that may occur during a blood fluid removal session for associating system parameter data and patient parameter data to enhance the blood fluid removal session or to tailor the blood fluid removal treatments to render the treatment patient-specific. It will be understood that any suitable method or process may be employed to achieve such results, and such methods or processes are contemplated for use herein. It will be further understood that similar methods or processes may be employed to enhance or tailor system parameters prior to initiating a blood fluid removal session so that patient-specific parameters may be set at the beginning of a session.

For example and with reference to FIG. 43 a flow diagram depicting a method that may be employed to determine which system parameters to select at the beginning of a blood fluid removal session is shown. The depicted method is similar in many respects to the method depicted in FIG. 41. In FIG. 43, the method includes receiving, inputting or obtaining patient or physician input 900 and patient physiological parameters 910. As discussed above with regard to FIG. 35, physician or patient input may include how long since the patient's last blood fluid removal session, how long does the patient have for the given blood fluid removal session and the like. In some embodiments, system generated input is provided based on data collected during the last session. Patient physiological parameters can be similar to those described above. A history lookup table may be consulted 920, and a determination can be made as to whether the patient has previously come to a blood fluid removal session in a similar state 930 based on the patient or physician input, the patient's physiological parameters, or other input. If a determination is made that the patient has come to previous blood fluid removal session in a similar state 930, which decision may be made generally as described above with regard to FIG. 41, a determination can be made as to whether system parameters were used in such a previous session to which the patient responded to favorably or had an "effective" response 940. If the patient is determined to have had an effective response, then the initial system parameters may be set in accordance with the parameters stored in the history table 950. If the patient is determined to not have come to a blood fluid removal session in a similar state 930 or to not have had an effective response 940, then a default table (e.g., similar to as described above with regard to FIG. 41) may be consulted 960 and the initial system parameters can be set according to the parameters in the default table 970.

Additional examples of systems and teachings useful in practicing the above embodiments can be found in, for example, U.S. Provisional Patent Application No. 61/480,541, filed on Apr. 29, 2011, now expired, and U.S. patent application Ser. No. 13/424,517 filed Mar. 20, 2012, now U.S. 2012/0273415A1 published on Nov. 1, 2012, both entitled BLOOD FLUID REMOVAL SYSTEM PERFORMANCE MONITORING, U.S. Provisional Patent Application No. 61/480,539, filed on Apr. 29, 2011, now expired, and U.S. patent application Ser. No. 13/424,533 filed Mar. 20, 2012, now U.S. 2012/0277722A1 published on Nov. 1, 2012, both entitled ADAPTIVE SYSTEM FOR BLOOD FLUID REMOVAL, which applications are hereby incorporated herein by reference in their entirety to the extent that they do not conflict with the present disclosure.

EXAMPLES

Example 1

Figure 44:
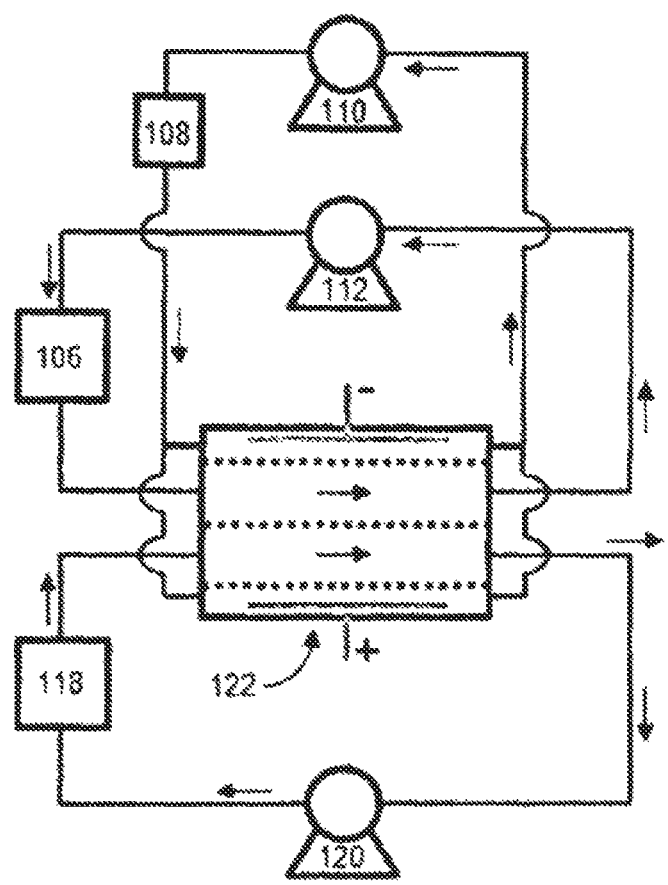
FIG. 44 shows an experimental set-up for electrolytic purification of a spent dialysate.

A lab-scale electrodialysis experiment was performed to establish the feasibility of purifying spent dialysate using an electrodialysis unit 122. The experimental set-up is shown in FIG. 44. The experiment was run in recirculation set-up with a concentrate reservoir 106, diluate reservoir 118 and electrode rinse reservoir 108. Peristaltic pumps 110, 112 and 120 were used for recirculation and the flow rates were set at 500 mL/min. The electrodialysis unit 122 used was model ED64004 (PCCell (Germany)). The unit consisted of 10 cell pairs with 11 Neosepta CMX cation exchange membranes and 9 Neosepta AMX anion exchange membranes, purchased from ASTOM Corporation (Japan). Each membrane has an active area of 64 $cm^2$ resulting in a total active area of 1280 $cm^2$. The electrodes were titanium with a platinum/iridium coating. Spent dialysate was prepared with the composition listed in Table 6, below. The spent dialysate was titrated to a pH of 6.5 with 37 wt % hydrochloric acid. The concentrate solution was prepared by mixing 0.56 volume parts of spent dialysate with 0.44 volume parts of deionized water. The electrode rinse solution consisted of 100 mM sodium sulfate titrated to a pH of 3 with sulfuric acid.

TABLE 6

| Composition of Spent Dialysate | |
|---|---|
| Component | Concentration |
| Na+ | 140 mM |
| Ca++ | 1.5 mM |
| K+ | 3 mM |
| Mg++ | 0.375 mM |
| Cl- | 171 mM |
| Acetate | 4 mM |
| Bicarbonate | 33 mM |
| Glucose | 200 mg/dL |
| Ammonium | 65 mM |
| Phosphate | 2.6 mM |

3000 ml of spent dialysate was added to the diluate reservoir 118. The concentrate reservoir 106 contained 600 mL of concentrate solution, described above. The electrode rinse reservoir contained 2000 mL of the electrode rinse solution described above. The experiment was started by applying 8V DC across the electrodialysis unit and starting the re-circulating pumps at a flow rate of 500 mL/min. The concentrate 106 and diluate 118 reservoirs were placed on stir-plates with magnetic stir-bars to ensure good mixing. At various time points, 1 ml samples were removed from each reservoir and analyzed for sodium, potassium, calcium, magnesium, chloride, ammonium, phosphate, bicarbonate and pH using a CCX analyzer and a BioProfile 300 analyzer, both manufactured by NovaBiomedical. Also, the current was monitored using a Fluke 179 True RMS multimeter.

Figure 45:
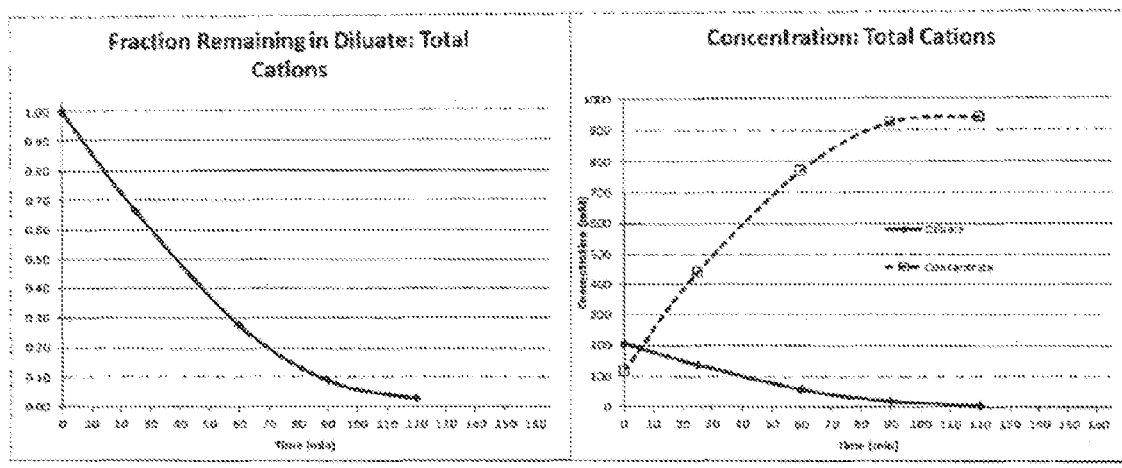
FIG. 45 shows data obtained from an experiment for the electrolytic purification of a spent dialysate.

FIG. 45 shows the fractional reduction in total cation concentration (left) and the total cation concentrations in the diluate and concentrate reservoirs (right). After 90 minutes, the total cation concentration was reduced by 90%. The current during the run decreased slowly from 1450 mA down to 220 mA after two hours.

Figure 46:
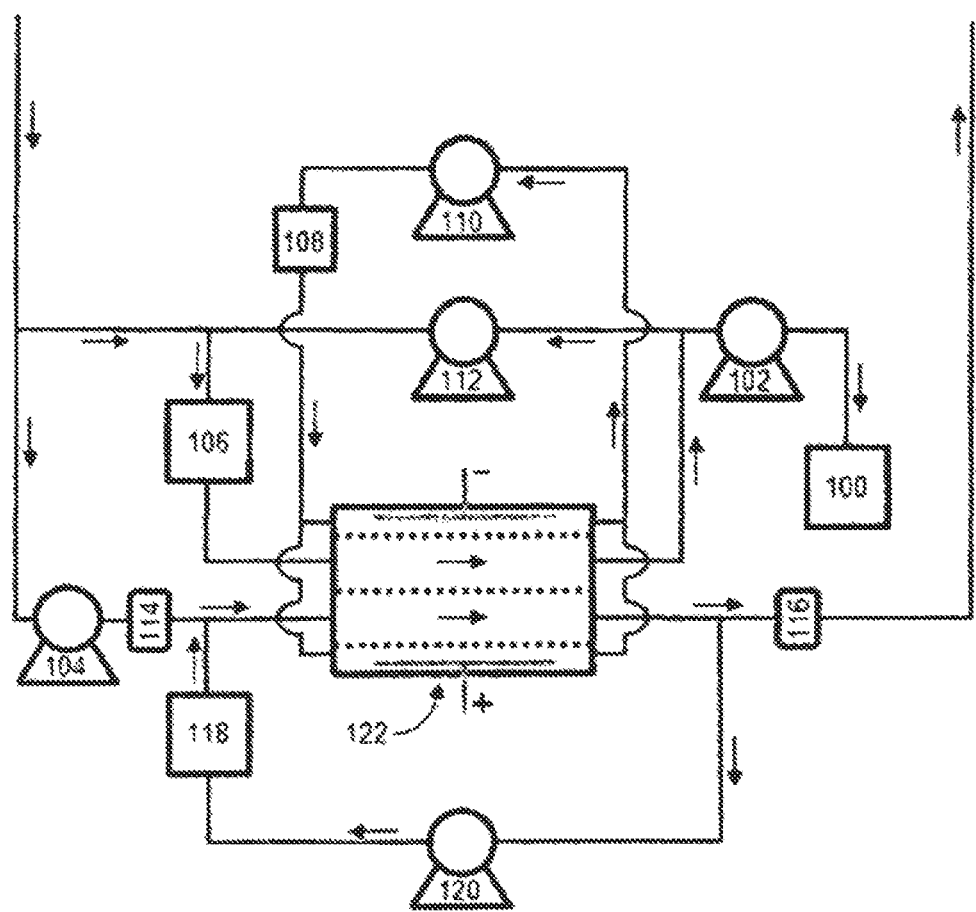
FIG. 46 shows a schematic for an embodiment of a purification module in accordance with some embodiments.

Using the experiment presented above, the operation of a scaled-up configuration shown in FIG. 46 can be demonstrated. For a portable dialysis system, the dialysate recirculation pump 104 can flow at 129 ml/min and the control pump 102 can flow at a flow rate of 14 ml/min (8 ml/min from ultrafiltration and 6 ml/min from the concentrate infusion set 35). The concentrate 112, diluate 120 and electrode rinse 110 re-circulating pumps can flow at 500 mL/min or higher. Based on the experiment above, the diluate 118, concentrate 106 and electrode rinse 108 reservoirs can have volumes of 500 mL, 2000 mL, and 2000 mL, respectively. The lab-scale experimental data indicates 90% removal of total cations in 90 minutes for the 3000 mL diluate reservoir, which is equivalent to a feedflow rate of 33.33 mL/min. Therefore, in order to remove 90% of total cations from a dialysate flow rate of 129 mL/min, the electrodialysis unit 122 can have a total active membrane area increased by a factor of 3.9 compared to the example, which would result in a total active membrane area of 0.5 $m^2$. The membrane area could be increased by adding more cell pairs to the stack or by increasing the area of each membrane, or a combination of both.

Example 2

Objective

This example is carried out in an effort to illustrate changes in skeletal muscle potential in response to variations in serum potassium concentration. The changes in skeletal muscle potential are effected via electrical excitation externally applied to the animal. The electrical excitation in this example is provided via a pulse stimulator coupled to an amplifier. Animal is infused with an externally applied potassium load and serum potassium concentrations are measured from the blood samples taken periodically. If this can be done, the procedure may be useful and significant in providing a method of monitoring potassium concentration without the subject having to go through the inconvenience and sometimes painful experiences associated with periodic blood sampling.

Experimental Setup

An exemplified pulsing schedule is generated for stimulating the skeletal muscle at varying rates. Briefly, the pulsing schedule generates a set of pulse stimulation every two seconds. Each set of pulse consists of a train of five pulses and the each pulse within this train lasts only 10 milli-seconds, which is referred to as ON-time. The OFF-time between the five pulses is altered to change the effective frequency of the pulse train. Stimulation starts at a frequency of f=5 Hz (period=1/freq=200 milli-seconds) and the frequency of stimulation is increased by one Hertz at each pulse, giving a series of frequencies, 5 Hz, 6, Hz, 7 Hz and so on. Stimulation is turned off for two second after the delivery of the last pulse train at f=40 Hz. Afterwards, the process is repeated using an infinite loop.—

The timing diagram for the pulse stimulation includes five pulses delivered starting at f=5 Hz and the frequency of stimulation is increased by 1 Hz every two seconds, until the frequency of stimulation has reached to f=40 Hz, while the serum potassium concentration is kept relatively constant.

Figure 50:
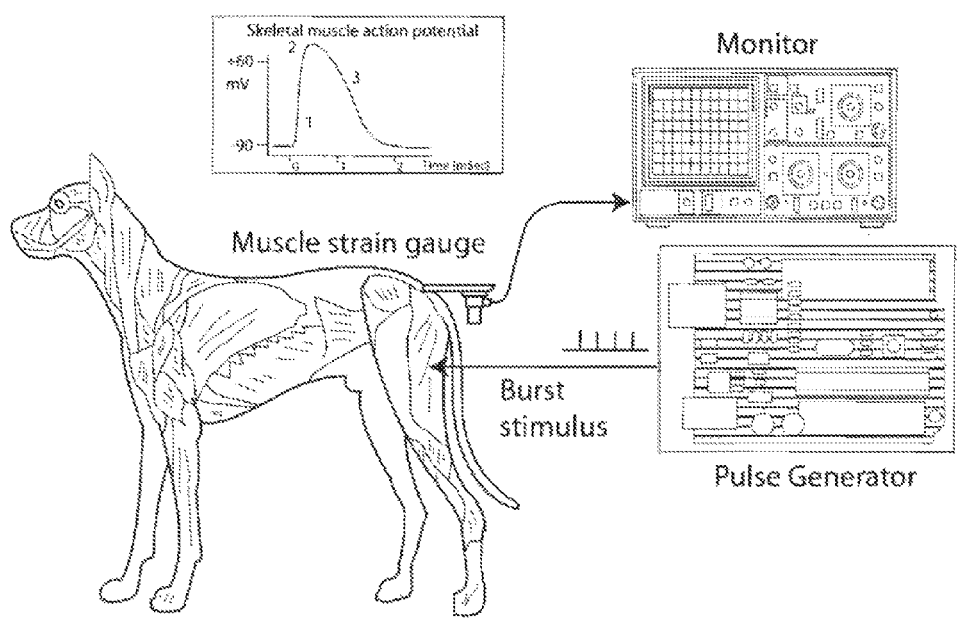
FIG. 50 depicts an exemplified experimental setup.

FIG. 50 depicts an exemplified experimental setup. Briefly, a pulse generator in the form of a stimulator is connected to an amplifier, which in turn is connected to the muscle in the hind leg of an anesthetized canine using skin penetrating electrodes. At the same time, an optical strain gauge placed on a cantilever beam is used to measure the bulking of the muscle as it contracts under isometric conditions. Animal is infused with 0.4 mM potassium chloride solution at a rate of 100 to 200 mL/hour for 5 hours to induce hyperkalemia. Serum potassium concentrations are measured from the blood samples taken every 15 minutes. Stimulation is applied soon after the collection of the blood samples to assure close correlation to measured potassium values. The serum potassium concentration increases quite steadily as a function of time (not shown).

Responses from the strain gauge sensor recorded (not shown) each at blood potassium concentrations of [K+]=5.6 mM and [K+]=13.2 mM, respectively. At [K+] of 5.6 mM, time (in milli-seconds) versus force (in arbitrary units) trace of the skeletal muscle while pulse stimulation containing five pulses are delivered starting at f=5 Hz to f=14 Hz. At [K+] of 13.2 mM, time (in milli-seconds) versus force (arbitrary units) trace of the skeletal muscle while pulse stimulation containing five pulses are delivered starting at f=5 Hz to f=14 Hz while the serum potassium concentration [$K^+$] is at 13.2 mM. It appears that relatively greater responses as recorded by the strain gauge sensor are observed with higher potassium concentration [K+] of 13.2 mM as compared to lower potassium concentration of [K+] of 5.6 mM. In both cases, the first mechanical response shown during the time indices t=1 sec and t=2 sec are believed to be due to the application of a pulse stimulation at f=5 Hz, the second mechanical response shown during the time indices t=3 sec and t=4 sec are believed to be due to the application of a pulse stimulation at f=6 Hz., and so on.

Figure 51:
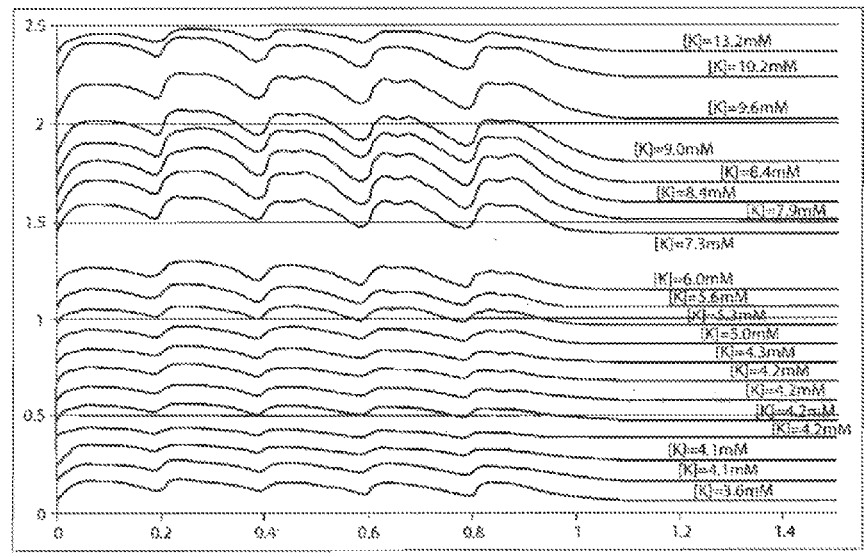
FIG. 51 demonstrates time (in milli-seconds) versus force (arbitrary units) trace of the skeletal muscle while pulse stimulation according to the Example(s).

FIG. 51 demonstrates time (in milli-seconds) versus force (arbitrary units) trace of the skeletal muscle while pulse stimulation containing five pulses are delivered at f=5 Hz while the serum potassium concentration [$K^+$] is changed from 3.6 mM to 13.2 mM. In particular, FIG. 51 demonstrates that the mechanical response obtained with the application of the stimulation at f=5 Hz while the serum potassium concentrations are changed from [K+]=3.6 mM to [K+]=13.2 mM. In that diagram, vertical scale of each trace is the same, but the vertical offset is increased to separate the traces for ease of visualization. As can be viewed from FIG. 51, the amplitude of the mechanical response of the skeletal muscle, as measured by the strain-gauge sensing the bulking of the muscle, increase as the serum potassium concentration increases.

Figure 52:
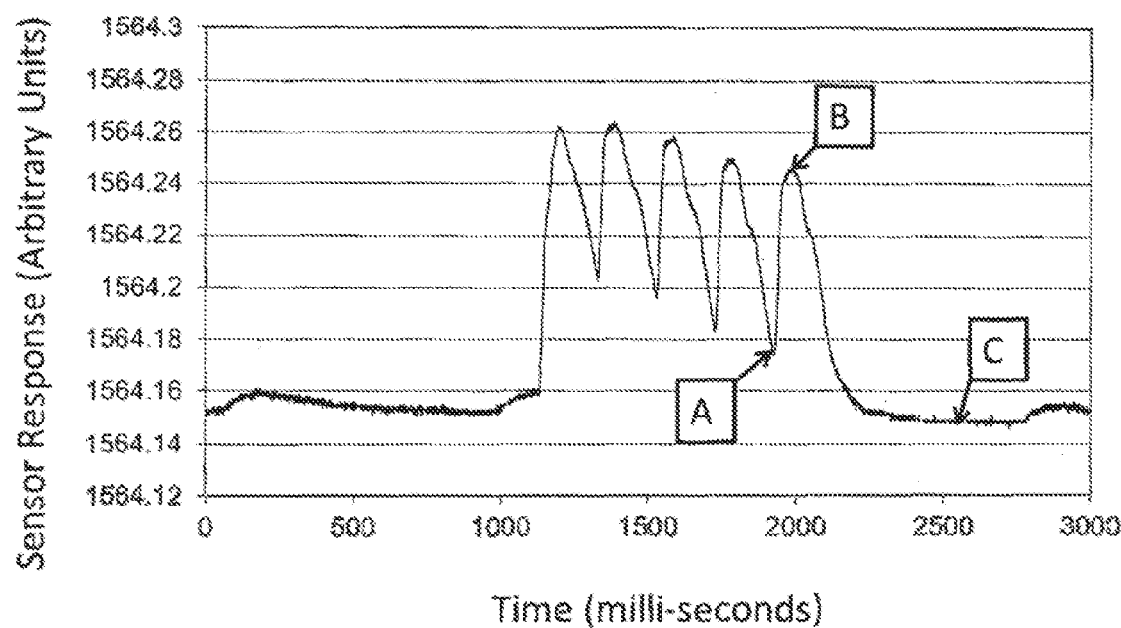
FIG. 52 demonstrates selection of data points computing mechanical responses from a pressure strain gauge.

In order to quantify the mechanical response of the stimulated muscle as recorded by the strain gauge, a number of points along the response line are selected and are depicted in FIG. 52. In particular, FIG. 52 demonstrates the selection of data points A and B for the computation of the response, wherein the computed response is the difference in the amplitudes of the signal at times labeled as A and B. Point A represents the minimum of the mechanical response trace prior to the $5^{th}$ peak, and point B represents the maximum of the mechanical response trace during the $5^{th}$ peak. Point C: Baseline value of mechanical response trace following the $5^{th}$ peak. The following two equations are used to compute the responses:

$$CR1=MB-MC$$

$$CR2=MB-MA$$

In the equations shown immediately above, CR1 and CR2 represent the computed responses, and MA, MB and MC each represent the mechanical response at points A, B and C.

Figure 53:
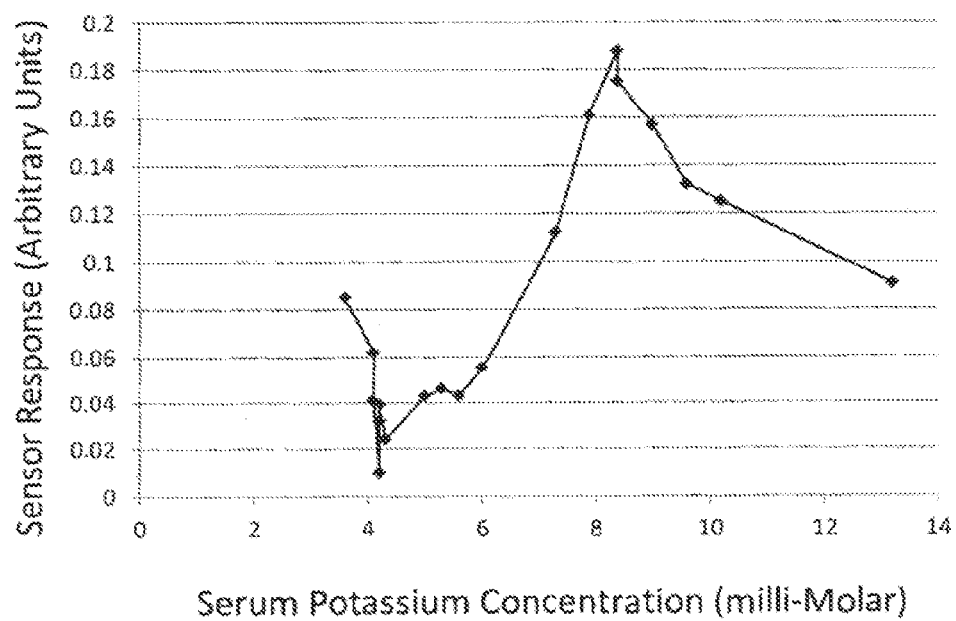
FIG. 53 shows the computed response CR1 as a function of the serum potassium concentration.

FIG. 53 shows the computed response CR1 as a function of the serum potassium concentration. It should be noted that the response is fairly linear in the clinically significant range of hyperkalemia, i.e. [K+]=5 mM to [K+]=9 mM. Furthermore, the anomalies in the behavior of the computed response CR1 at the low serum concentrations of [K+]=3 mM to [K+]=5 mM are believed to be due to experimental artifacts as the body initially struggles to compensate for the sudden infusion of bolus amount of potassium, until the hyperkalemia is established.

Alternative methods to determine the computed response can be used. For example, one can detect the changes in the power of the sensor signal at the stimulation frequency. This can be achieved using a tuned analog filter, such as an passive RLC circuit or an active circuit, including an operational amplifier. A digital filter implemented using a logic circuit or running as a computer program, such as a Fast Fourier Transform (FFT), would also be able to extract the power of the sensor signal at the stimulation frequency. In either case, the changes in the amplitude of the sensor signal at the stimulation frequency, instead of the equations for CR1 and CR2, could be used to estimate the serum potassium concentration. Individuals skilled in the art would recognize other methods of detecting the signs of fusion formation as a result of burst stimulation, and all such techniques are within the scope of the present invention.

Muscle response can be sensed using an external transducer. In this case, the bulging of the muscle in its mid-section during a contraction can be detected using a pressure sensor. Such a pressure sensor may be pressed onto the muscle through the skin, or be sensing the bulging via a secondary linkage system. In this example, a strain gauge is mounted onto a cantilever beam where the bulging of the contracted muscle changes the strain on the beam, which in turn is detected by the strain gauge. Alternatively, a blood pressure cuff can be used to detect the bulging of the muscle. In this case, the blood pressure cuff is inflated to a pressure that is sufficient to make good contact with the skin, such as 50 mm Hg. Afterwards, the pulse stimulation at the frequency of f=5 Hz is applied and the resulting pressure waveform is analyzed as described above. This system has the advantage of measuring the blood pressure along with the changes in the serum potassium concentrations.

Conclusion

This example as described herein demonstrates that changes in skeletal muscle potential can be response indicators for variations in serum potassium concentration. This is useful and significant at least in that potassium concentration monitoring can be made possible without the subject having to go through the inconvenience and sometimes painful experiences associated with periodic blood sampling; instead, potassium concentration monitoring can be conducted via a procedurally more convenient route such as external pressure sensor and blood pressure cuff.

Example 3

Objective

This Example is conducted to determine if changes in the serum potassium concentration during dialysis can be detected by changes in the features of the ECG (electrocardiography), using data from the PODS (Potassium Observation in Dialysis Subjects Study). As detailed herein below, dialysis subjects are recruited and monitored in an effort to optimize their dialysis regimen and reduce their mortality and morbidity. Particularly various ECG features are reviewed in response to the potassium concentration changes and the ECG features that represent the most significant and/or consistent changes are identified for this subject population based on the data from the PODS. The data may then be used for the design of a detection algorithm for abnormality hypokalemia in heart failure subjects.

Experimental Setup

The PODS study is a single center, acute, non-randomized feasibility study in which data from 23 hemodialysis subjects are obtained via an external DR-180+ holter monitor and AUDICOR heart sounds holter. A 12-lead ECG is recorded continuously during a dialysis session using the DR-180+ recorder. Blood samples for electrolyte measurements are collected 15 minutes prior to dialysis, at 1 hour and 3 hours after the onset of dialysis, and 15 minutes after completion of dialysis.

The ECG signal(s) analyzed from the DR-180 holter are leads II, V2, V3, and V4. The primary analysis is done using the best signal available amongst the selected leads in order to maximize detection of P-waves, which can be very small for some subjects, and visually observable on maybe only one lead. A duplicate run is conducted using lead II only for obtaining a direct comparison to the run conducted on the best lead.

The following ECG features are measured: P-R interval, R-wave amplitude, QRS duration, T-wave amplitude, T-wave flatness, T-wave asymmetry, QT interval, QTc interval, TR amplitude ratio, T-slope and T-slope over amplitude.

Figure 54:
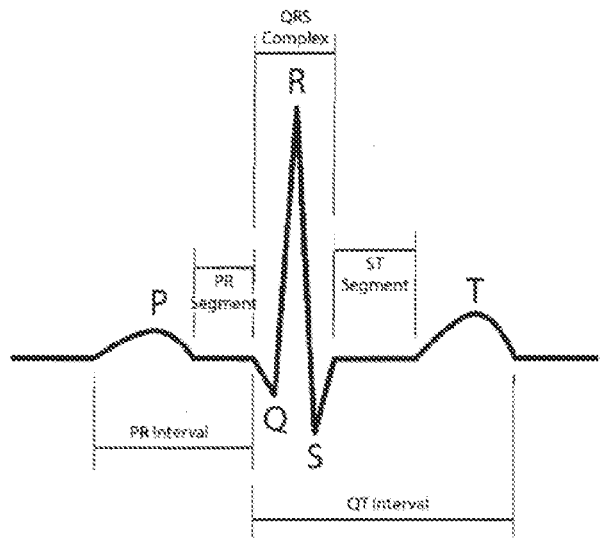
FIG. 54 shows the ECG markers.

Most of the ECG markers are evident from the diagram in FIG. 54. Amplitude measurements are made in the arbitrary units recorded in the file. QTc is the QT interval corrected for heart rate.

The T-wave flatness metric is based on kurtosis which describes the peakedness of a probability distribution. In this case, calculation of flatness characterizes the distribution of samples taken during the T-wave. The amplitude of the signal samples during the T-wave window are normalized to obtain a unit area and flatness is calculated as an inverse function of the fourth central moment, or kurtosis.

The formulas for the central moments used are given below:

$$M_1 = \sum_{n=0}^{N-1} n \cdot V(n)$$

$$M_k = \left[ \sum_{n=0}^{N-1} (n - M_1)^k \cdot V(n) \right]$$

As referenced in the formula shown above, $M_k$ is the k'th central moment, $V(n)$ is the T-wave, and n is the sample number. To find the point to use for Ton (start of the T-wave) given different baseline points, the minimum samples between the end of R-wave and the peak of the T-wave, and then between the peak of the T-wave and the end of the T-wave are found. The maximum of these two points is used as the baseline for finding the area of the T-wave. The points closest to the T-wave peak, both before and afterwards, which have signal amplitudes equal to this baseline are used to define the start and end of the T-wave window.

T-wave asymmetry evaluates differences in slope and duration of the ascending and descending parts of the T-wave. The time derivative of the T-wave is calculated and divided into two segments at the peak of the T-wave. Both segments are normalized with the maximum derivative within that segment. The descending T-wave is then flipped across the y-axis and x-axis and matched against the ascending segment. The segments are compared sample by sample, and the asymmetry score is calculated as the residual between the two segments. The point 50 ms after the end of the R wave is used for the start of the T-wave. Andersen, et al. preprocesses the data by calculating median beats, constructing XYZ vectors (a linear combination of leads I-II and V1-V6 which creates 3 orthogonal leads), and performing Principal Component Analysis to optimize for ST-T segment information and improve stability and repeatability of measurements. Principal Component Analysis is a technique which converts a set of observations of possibly correlated variables into a set of values of linearly uncorrelated variables called principal components. These preprocessing steps are not done with this data other than calculating median beats.

Figure 55:
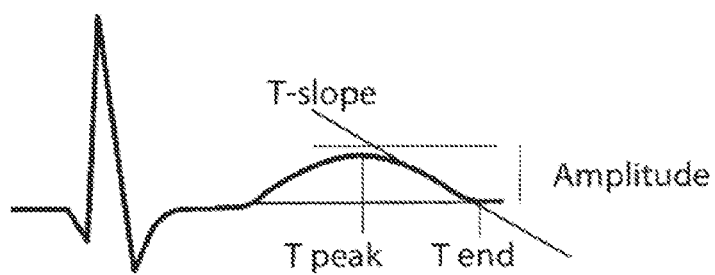
FIG. 55 shows an exemplified calculation of T-slope.

T-slope is the slope of the line drawn between the peak of the T-wave and the end of the T-wave, as shown in FIG. 55. T-slope over amplitude is the reciprocal of the time from the peak of the T-wave to the end of the T-wave, as shown below.

$$T\text{-slope over amplitude} = \frac{\frac{Amplitude}{(T\text{end} - T\text{peak})}}{Amplitude} = (T\text{end} - T\text{peak})$$

Plots are made to show the trend of each parameter throughout the course of dialysis, against the potassium values. Histogram plots are also made of the difference in each ECG parameter between the final blood draw and the initial blood draw. The plots in the PODS study report show the potassium axis on a scale from largest to smallest as dialysis removes potassium from the body.

Results—ECG Changes Seen on Leads II, V2, V3 and V4

The serum potassium concentrations of subjects decrease during the first hour of dialysis for all the subjects examined in the PODS. Most subjects continue to experience decreases in potassium levels through the end of dialysis, although some experience increases after 1 hour or 3 hours.

The ECG markers are measured from 60-second sections of data measured within 5 minutes of the blood draw times using the "best" of leads II, V2, V3, and V4 for each subject.

The ECG features showing the most consistent changes during dialysis are T/R amplitude ratio, T-slope, T-wave amplitude, and R-wave amplitude. As can be observed from the following figures, and as serum potassium concentration decreases, the T-wave amplitude decreases in general, the R-wave amplitude increases in general, the T-wave flatness increases in general, and T-slope decreases in general. More particularly, and as shown in the following Figures, the mean change in R-wave amplitude is 24.2%, with a range of change of from −8.9% to 90.2%, the mean change in T-wave amplitude is 25.5% with a range of change of from −93.1% to 59.7%, the mean change in T-wave flatness is 7.3% with a range of change of from −3.0% to 38.2%, and the mean change in T-slope is −31.2% with a range of change of from −94. % to 42.5%.

Figure 56:
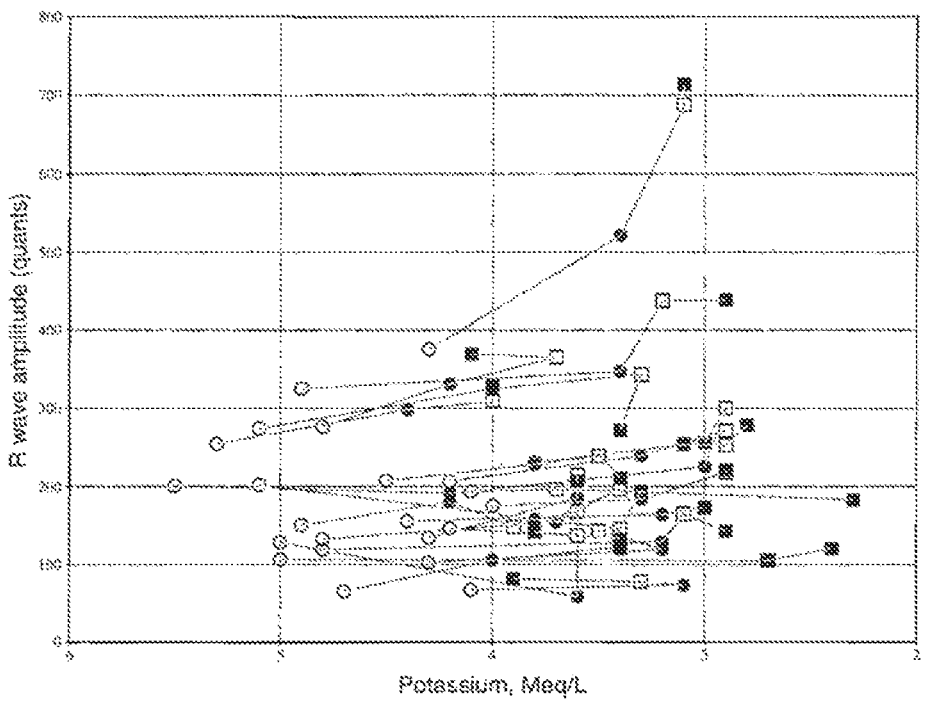
FIG. 56 shows changes in R-wave amplitude (in arbitrary units) during dialysis on best lead.
Figure 57:
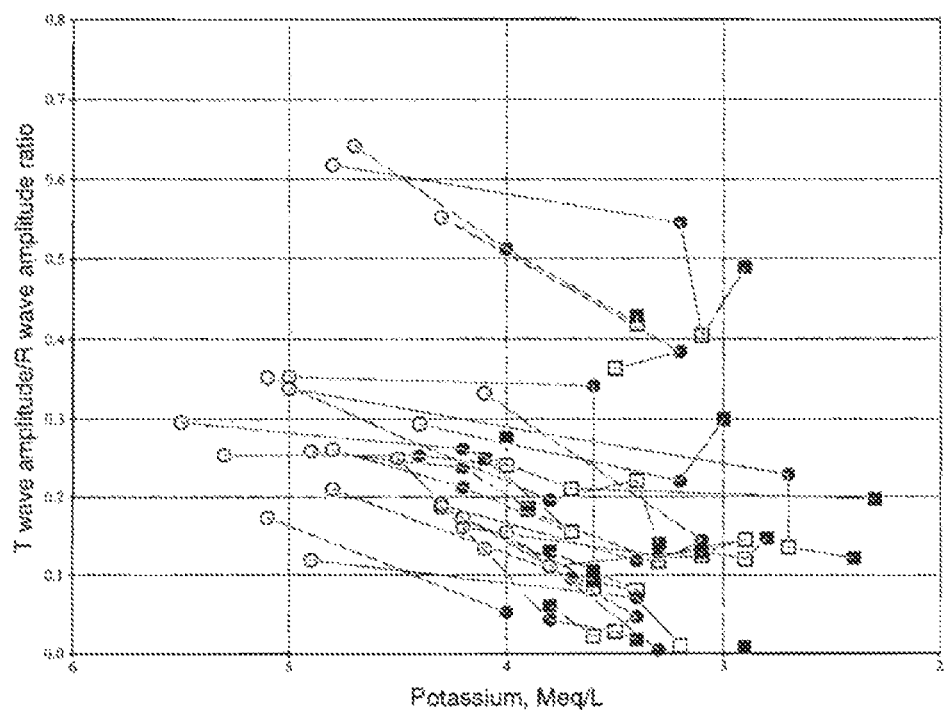
FIG. 57 shows change in T/R amplitude ratio during dialysis on best lead.
Figure 58:
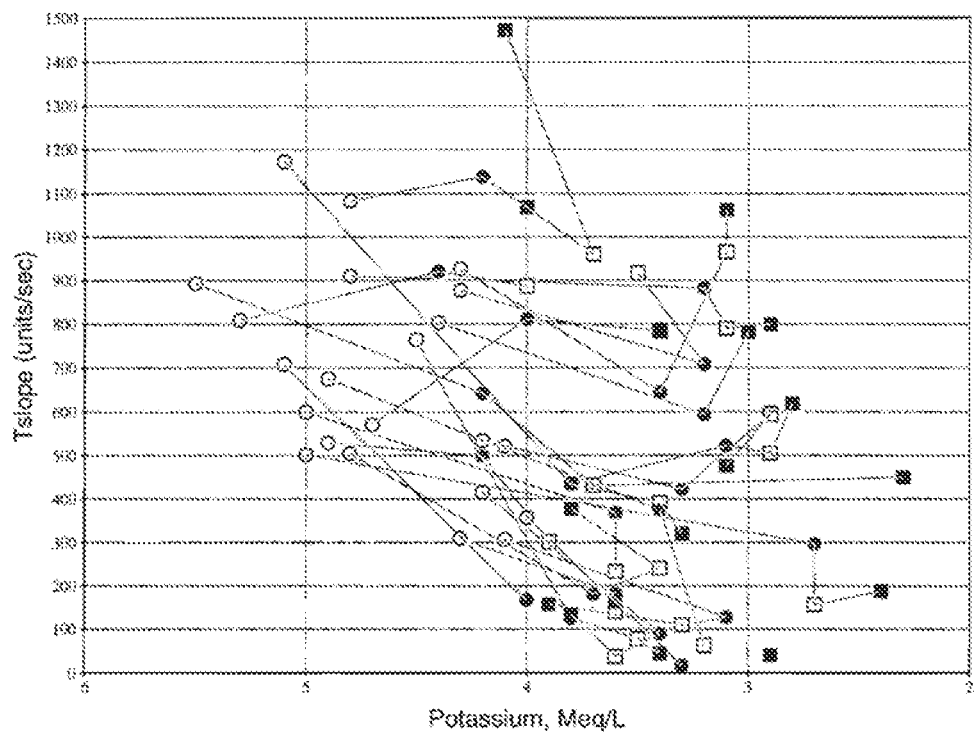
FIG. 58 shows change in T-slope during dialysis on best lead.

The following figures including FIG. 56 to FIG. 58, open circles represent data obtained prior to dialysis, filled circles represent data 1 hour into dialysis, open squares represent data 3 hours into dialysis, and filled squares represent data after dialysis. These figures are plotted against corresponding serum potassium concentration values. The X-axis scale on the dot plots is reversed to show progression during dialysis from left to right as potassium concentration is marked from greater at the left to smaller at the right.

From the results obtained according to this Example, the following ECG features (values not shown) either do not change significantly or do not change consistently for the period of dialysis as examined: the P-R interval, the QRS duration, the QT interval, the QTc interval, the T-wave asymmetry, and T-slope over amplitude.

However, several ECG features do change significantly and/or consistently for the period of dialysis as examined. For instance, and as demonstrated in FIG. 58, R-wave amplitudes increase significantly and/or consistently during dialysis, with the majority of the examined subjects exhibiting a mean increase of 24.2%.

Results—On the Lead II Only

The results using lead II only for all subjects are also analyzed to see whether similar changes can be observed on the most Reveal-like vector. In this part of the Example, the best leads analysis detailed above is believed to provide a relatively higher likelihood of detecting the P-waves and the T-waves with dependable measures, as the leads are selected to have larger P- and T-waves with less noise. The lead II only analysis is included to give an estimate of the loss of sensitivity in the metrics of a less-than-optimal lead.

The following ECG features continue to elicit significant and/or consistent changes during dialysis that are comparable to those elicited in the best lead analysis: the R-wave amplitude, the T-wave amplitude and the T/R amplitude ratio. However, the changes seen with the T-wave amplitude and the T/R amplitude referenced in the lead II only analysis are not as substantially as those seen with the best lead analysis.

The other ECG markers have very similar changes using only lead II for analysis as compared to using the best lead. For instance, the following ECG features continue to elicit insignificant and/or inconsistent changes during dialysis for the period examined: the P-R interval, the QRS duration, the QT interval, the T-wave asymmetry, and the QTc measurement.

Figure 59:
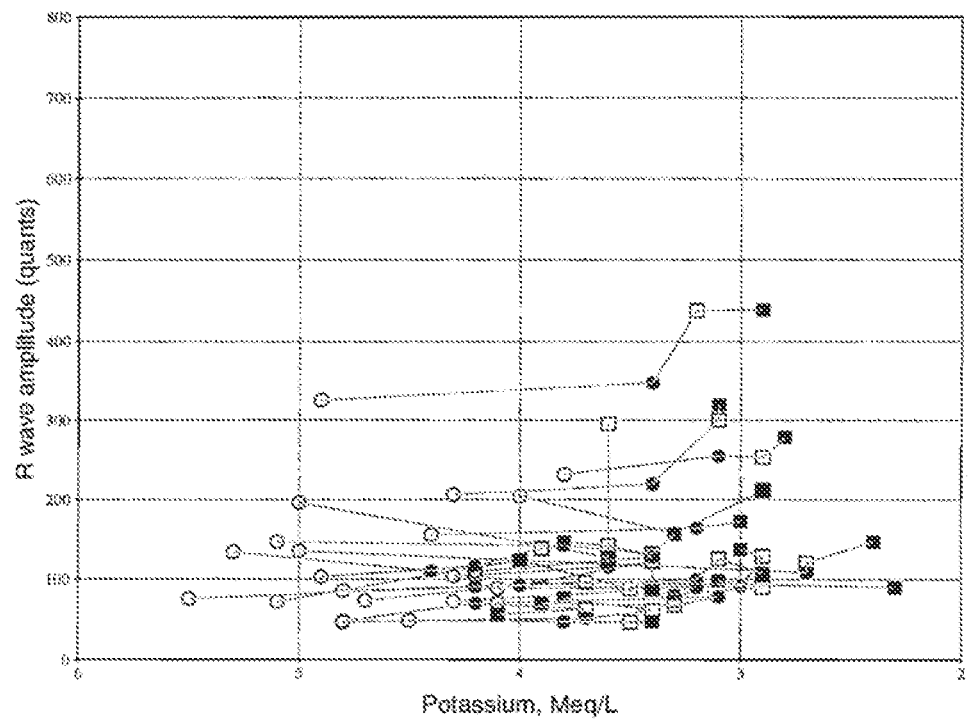
FIG. 59 shows R-wave amplitude (in arbitrary units) during dialysis on lead II.

FIG. 59 demonstrates that R-wave amplitudes increase significantly, with the majority of the examined subjects exhibiting an increase of up to 66.2% in the R-wave amplitude.

Figure 60:
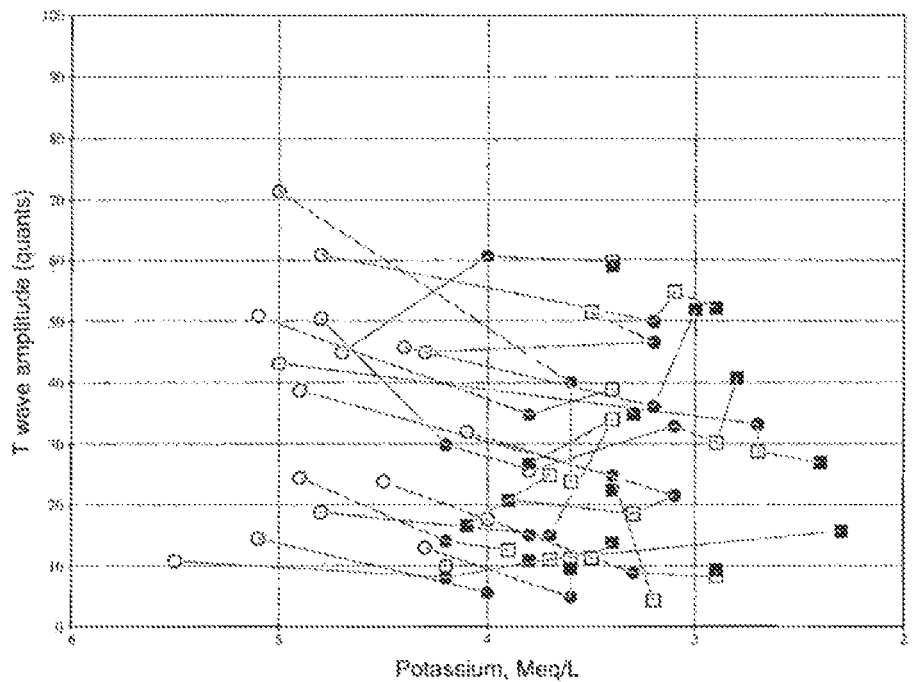
FIG. 60 shows change in T-wave amplitude (in arbitrary units) during dialysis on lead II.

FIG. 60 demonstrates that T-wave amplitudes change inconsistently and/or insignificantly among the subjects examined. This suggests that the precordial leads may exhibit relatively greater sensitivity to T-wave changes due to potassium. In certain instances, however, changes to R-wave amplitude may be more stably maintained in response to serum potassium concentration variation in comparison to T-wave amplitude. Without wanting to be limited to any particular theory, it is believed that most ECG leads give a good representation of the R-wave, so changes in depolarization are likely to be seen on all vectors. R-wave amplitude may also be more sensitive to filtering. Changes in repolarization as reflected in T-waves may be more sensitive to vector, but may be seen at lower potassium levels, so may be an earlier indicator of hyperkalemia, and better indicator of potassium abnormality. Both R-wave amplitude and T-wave metrics are of interest as markers.

Figure 61:
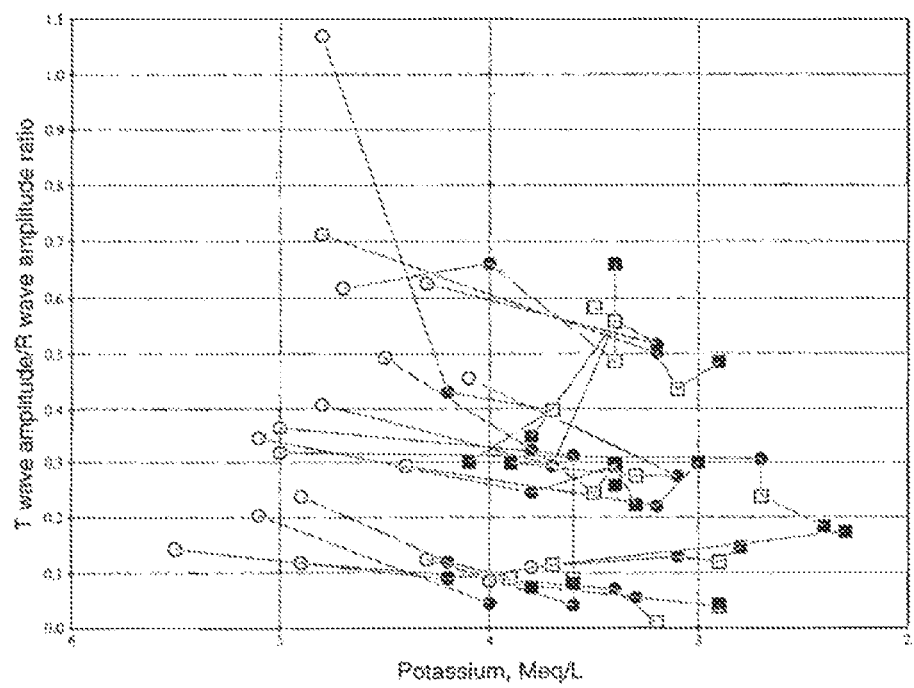
FIG. 61 shows T/R amplitude ratio during dialysis on lead II.
Figure 62:
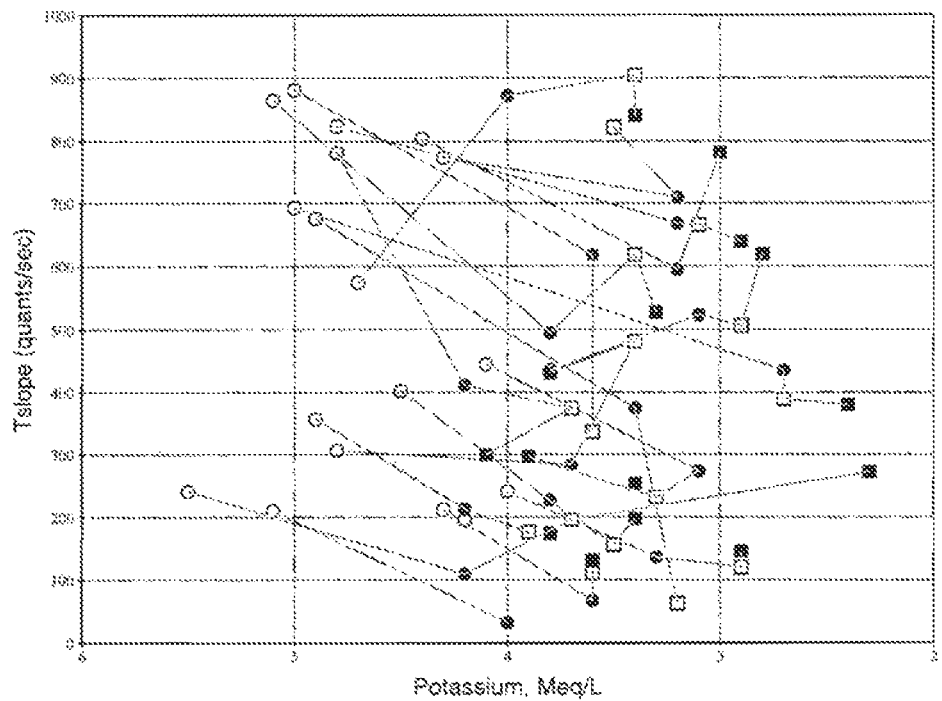
FIG. 62 shows change in T-slope during dialysis on lead II.

FIG. 61 demonstrates that the T/R ratios decrease significantly, with the majority of the examined subjects exhibiting a decrease of up to −91.6%. FIG. 62 demonstrates that T-slope measurements decrease significantly, with the majority of the examined subjects exhibiting a decrease as much as −90.8%. This appears to suggest that when lead of different sensitivity is used, at least three of the four ECG features, the T-wave amplitude, the R-wave amplitude, the T/R amplitude ratio and the T-slope, may each be used as markers or indicators for serum potassium concentration changes.

Figure 63:
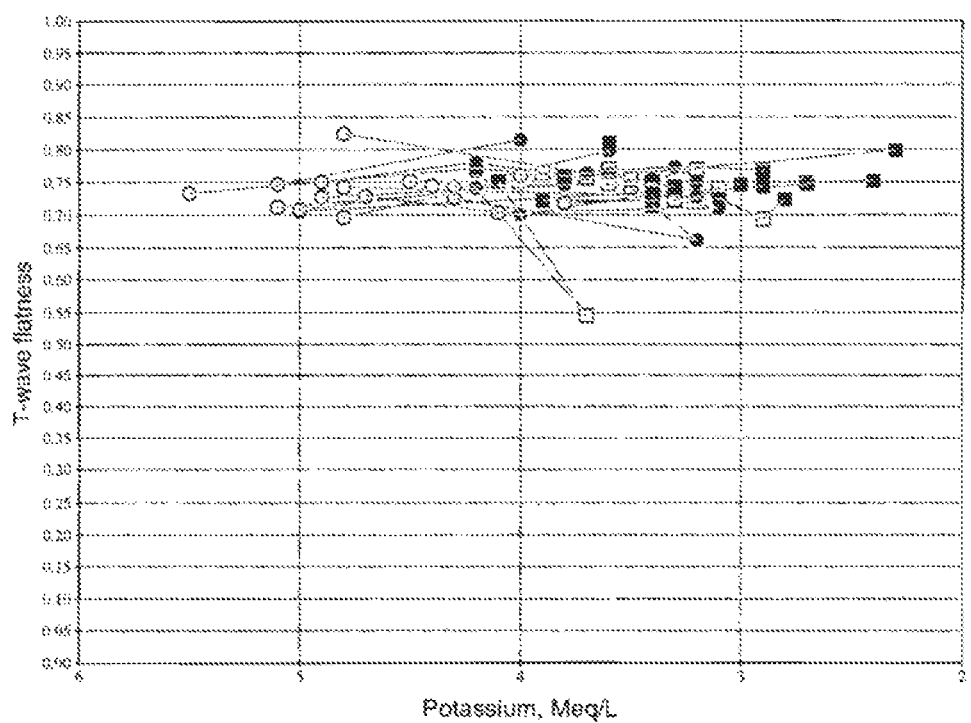
FIG. 63 shows T-wave flatness during dialysis on lead II.

In comparison to above-mentioned data seen with the best lead analysis, changes in T-wave flatness, T-slope over amplitude are not as substantial. This again may suggest that these two ECG features may be vector dependent to some extent. FIG. 63 demonstrates performance of the T-wave flatness.

Repeatability Analysis

Of the subjects examined, three are enrolled twice for this reproducibility or repeatability analysis. The following four ECG features are measured and the measured values (not shown) are consistently similar and comparable to those seen with the first session run: the R-wave amplitude, the T-wave amplitude, the T/R amplitude ratio and the T-slope.

Conclusions

In the PODS described herein above, certain ECG markers are measured at times corresponding to various blood draws throughout a dialysis session. The ECG changes during dialysis are described and quantified. The analysis is done using the "best lead" with largest P and T waves at baseline, and repeated using only lead II, which most closely resembles the Reveal electrogram. The best lead is usually V4 or V2. The serum potassium levels in the subjects range from 2.3 to 5.5 mM, so some subjects start the dialysis session with a potassium level slightly above normal levels and some conclude the session at sub-normal levels, but no subject have potassium levels in a dangerous range. The ECG metrics showing the largest and most consistent changes with change in potassium are T/R amplitude ratio, T-slope, T-wave amplitude, and R-wave amplitude.

The particular embodiments disclosed above are illustrative only, as the invention may be modified and practiced in different but equivalent manners apparent to those skilled in the art having the benefit of the teachings provided herein. Furthermore, no limitations are intended with respect to the details of construction or the design shown herein, other than as described in the claims below. It is therefore evident that the particular embodiments disclose above may be altered or modified and that all such variations are considered to be within the scope and spirit of the present invention.

We claim:

1. A multimodal dialysis apparatus, comprising:
an extracorporeal flow path for transporting blood of a subject to a hemodialysis unit;
at least one of an electrocardiogram sensor and an electromyogram sensor configured to detect a change in muscle activity or nerve activity of the subject and configured to produce at least one electrical signal based on the change in muscle activity or nerve as detected, the electrical signal being indicative of a serum potassium concentration;
a dialysate flow path configured to transport a dialysate fluid to the hemodialysis unit; and
an infusate pump comprising a potassium solution in fluid communication with the dialysate flow path such that the infusate pump configured to adjust a potassium concentration in the dialysate flow path based at least in part on the serum potassium concentration obtained via the at least one of the electromyogram sensor and the electrocardiogram sensor.

2. The multimodal dialysis apparatus of claim 1, further comprising one or more detectors including at least one of a nerve electrogram amplifier, an accelerometer, a strain gauge, and a pressure gauge for detecting the change in muscle activity.

3. The multimodal dialysis apparatus of claim 1, wherein the medical device is externally applicable to or implantable in the subject.

4. The multimodal dialysis apparatus of claim 1, wherein the electromyogram sensor is a skeletal muscle strain sensor.

5. The multimodal dialysis apparatus of claim 1, wherein the electromyogram sensor is a blood pressure sensor.

6. The multimodal dialysis apparatus of claim 1, wherein the electrocardiogram sensor includes one or more electrocardiogram electrodes for receiving one or more electrocardiogram features from the subject, the one or more electrocardiogram features including T-wave amplitude, R-wave amplitude, T-slope, ratio of T-wave amplitude to R-wave amplitude (T/R ratio), and T-wave flatness.

7. The multimodal dialysis apparatus of claim 6, further comprising an electrocardiogram algorithm for producing an output on serum potassium concentration in the subject based on a value of the one or more electrocardiogram features, wherein the electrocardiogram algorithm includes one or more of the following operational rules: i) the output on the serum potassium concentration being a function of the R-wave amplitude; ii) the output on the serum potassium concentration being a function of the T-wave amplitude; iii) the output on the serum potassium concentration being a function of the T/R ratio; and iv) the output on the serum potassium concentration being a function of the T-wave flatness.

8. The multimodal dialysis apparatus of claim 7, wherein the output on the serum potassium concentration is a difference between a serum potassium concentration at time $t_1$ of the subject and a baseline potassium concentration at time $t_0$ of the subject, time $t_1$ being at least 10 minutes apart from $t_0$.

9. The multimodal dialysis apparatus of claim 8, wherein the baseline serum potassium concentration is a value selected from the group consisting of a baseline serum potassium concentration of the subject obtained at a periodic blood draw, a baseline serum potassium concentration of the subject obtained at the onset of a dialysis session, and a baseline serum potassium concentration of the subject at the end of a dialysis session.

10. The multimodal dialysis apparatus of claim 1, wherein the electromyogram sensor is a nerve electrogram sensor.

11. The multimodal dialysis apparatus of claim 9, wherein the R-wave amplitude of operational rule i) is a difference between an R-wave amplitude at time $t_1$ of the subject and a baseline R-wave amplitude at time $t_0$ of the subject, the T-wave amplitude of operational rule ii) is a difference between a T-wave amplitude at time $t_1$ of the subject and a baseline T-wave amplitude at time $t_0$ of the subject, the T/R ratio of operational rule iii) is a difference between a T/R ratio at time $t_1$ of the subject and a baseline T/R ratio at time $t_0$ of the subject, and the T-wave flatness of operational rule iv) is a difference between an T-wave flatness at time $t_1$ of the subject and a baseline T-wave flatness at time $t_0$ of the subject.

12. The multimodal dialysis apparatus of claim 10, wherein the baseline potassium concentration of the subject is 3.0 to 5.5 mM at time $t_0$.

13. The multimodal dialysis apparatus of claim 6, wherein the one or more electrocardiogram electrodes include one or more of lead II, lead V2, lead V3 and lead V4.

14. The multimodal dialysis apparatus of claim 6, wherein the one or more electrocardiogram electrodes consist of lead II only.

15. The multimodal dialysis apparatus of claim 7, wherein the electrocardiogram algorithm includes one or more of the operational rules i), iii) and iv).

16. The multimodal dialysis apparatus of claim 7, wherein the output on the serum potassium concentration is in positive correlation with the R-wave amplitude.

17. The multimodal dialysis apparatus of claim 7, wherein the output on the serum potassium concentration is in negative correlation with the T-wave amplitude.

18. The multimodal dialysis apparatus of claim 7, wherein the output on the serum potassium concentration is in negative correlation with the T-slope.

19. The multimodal dialysis apparatus of claim 7, wherein the output on the serum potassium concentration is in positive correlation with the T-wave flatness.

20. The multimodal dialysis apparatus of claim 7, wherein the one or more electrocardiogram electrodes includes a first set of electrodes consisting of lead II, lead V2, lead V3 and lead V4, and a second set of electrodes consisting of lead II only, wherein the electrocardiogram algorithm further includes a calibration rule that the multimodal dialysis apparatus is operationally calibrated if one or more of the following is met: v) a difference between the outputs according to rule ii) from the first set of electrodes and the second set of electrodes is no greater than 20%; vi) a difference between the outputs according to rule iii) from the first set of electrodes and the second set of electrodes is no greater than 20%; and vii) a difference between the outputs according to rule iv) from the first set of electrodes and the second set of electrodes is no greater than 20%.

21. The multimodal dialysis apparatus of claim 7, wherein the one or more electrocardiogram electrodes includes a first set of electrodes consisting of lead II, lead V 2, lead V3 and lead V4, and a second set of electrodes consisting of lead II only, wherein the electrocardiogram algorithm further includes a calibration rule that the multimodal dialysis apparatus is operationally calibrated if one or more of the following is met: v) a difference between the outputs according to rule ii) from the first set of electrodes and the second set of electrodes is no greater than 10%; vi) a difference between the outputs according to rule iii) from the first set of electrodes and the second set of electrodes is no greater than 10%; and vii) a difference between the outputs according to rule iv) from the first set of electrodes and the second set of electrodes is no greater than 10%.

22. The multimodal dialysis apparatus of claim 1, further comprising one or more potassium-sensitive electrodes for measuring a potassium ion concentration in the dialysate flow path.

23. A method for conducting a dialysis treatment in a subject, the dialysis treatment being conducted with an extracorporeal flow path for transporting blood of the subject to a hemodialysis unit, a dialysate flow path for transporting a dialysate fluid to the hemodialysis unit, and an infusate pump in potassium communication with the dialysate flow path, the method comprising:
connecting at least one electrocardiogram sensor to a subject to receive one or more electrocardiogram features;
applying an electrocardiogram algorithm to the one or more electrocardiogram features to obtain an indicator for serum potassium concentration of the subject, wherein the electrocardiogram algorithm includes one or more of the following operational rules: i) the output on the serum potassium concentration being a function of an R-wave amplitude; ii) the output on the serum potassium concentration being a function of an T-wave amplitude; iii) the output on the serum potassium concentration being a function of a T/R ratio; and iv) the output on the serum potassium concentration being a function of a T-wave flatness; and
adding an amount of potassium via the infusate pump into the dialysate flow path, wherein the amount of potassium is determined based at least in part on the serum potassium concentration obtained via the at least the electrocardiogram sensor.

* * * * *